(12) United States Patent
Rabiner et al.

(10) Patent No.: US 12,397,071 B2
(45) Date of Patent: Aug. 26, 2025

(54) ANTI-MICROBIAL BLUE LIGHT SYSTEMS AND METHODS

(71) Applicant: ABL Medical Inc., East Providence, RI (US)

(72) Inventors: Robert A. Rabiner, Dortmund (DE); Liane J. Rabiner, Dortmund (DE); Gene P. DiPoto, Upton, MA (US); Anthony W. O'Leary, Walpole, MA (US); Michael P. Mogul, San Diego, CA (US)

(73) Assignee: ABL Medical Inc., East Providence, RI (US)

( * ) Notice: Subject to any disclaimer, the term of this patent is extended or adjusted under 35 U.S.C. 154(b) by 0 days.

(21) Appl. No.: 18/240,984

(22) Filed: Aug. 31, 2023

(65) Prior Publication Data

US 2024/0058483 A1 Feb. 22, 2024

Related U.S. Application Data

(63) Continuation of application No. 17/896,902, filed on Aug. 26, 2022, now Pat. No. 11,813,368.
(Continued)

(51) Int. Cl.
*A61L 2/00* (2006.01)
*A61L 2/08* (2006.01)
*A61L 2/26* (2006.01)

(52) U.S. Cl.
CPC ............. *A61L 2/0052* (2013.01); *A61L 2/084* (2013.01); *A61L 2/26* (2013.01)

(58) Field of Classification Search
CPC ............................... A61L 2/0052; A61L 2/084
See application file for complete search history.

(56) References Cited

U.S. PATENT DOCUMENTS

| 5,443,495 A | 8/1995 | Buscemi et al. |
| 5,445,608 A | 8/1995 | Chen et al. |

(Continued)

FOREIGN PATENT DOCUMENTS

| CA | 3071998 A1 | 2/2019 |
| EP | 3370739 B1 | 1/2021 |

(Continued)

OTHER PUBLICATIONS

International Search Report;PCT/US22/41745; Nov. 22, 2022; By: Authorized Officer Shane Thomas.

*Primary Examiner* — Kevin Joyner
(74) *Attorney, Agent, or Firm* — Greenberg Traurig, LLP; David J. Dykeman; Jaime Burke

(57) ABSTRACT

Systems, devices and methods for controlled intramedullary delivery of light (frequencies from about 380 nm to about 500 nm) to treat tissue or bones disorders, including osteomyelitis, by a flexible fiber are provided, where the light is delivered in a circumferential fashion around the fiber, and where the energy delivered from the fiber is of a similar average intensity at the front end and back end of the fiber, and in between. The methods and systems deliver intramedullary light to the canal over long lengths via a minimally invasive pathway to a bone. The methods and systems deliver and maintain a light delivery system within the canal of the bone to provide single or multiple doses of light to kill, eliminate, remove or reduce bacteria, viruses, fungus and pathogens, without removal of the light fiber system, thereby providing single or multiple treatments.

17 Claims, 76 Drawing Sheets

Related U.S. Application Data

(60) Provisional application No. 63/264,174, filed on Nov. 17, 2021, provisional application No. 63/238,104, filed on Aug. 27, 2021.

(56) References Cited

U.S. PATENT DOCUMENTS

| | | |
|---|---|---|
| 5,607,419 A | 3/1997 | Amplatz et al. |
| 5,620,438 A | 4/1997 | Amplatz et al. |
| 5,730,719 A | 3/1998 | Edwards |
| 5,800,379 A | 9/1998 | Edwards |
| 5,930,424 A | 7/1999 | Heimberger et al. |
| 7,806,900 B2 | 10/2010 | Rabiner |
| 7,811,284 B2 | 10/2010 | Rabiner |
| 7,811,290 B2 | 10/2010 | Rabiner |
| 7,842,040 B2 | 11/2010 | Rabiner et al. |
| 7,843,328 B2 | 11/2010 | Redmond et al. |
| 7,879,041 B2 | 2/2011 | Rabiner et al. |
| 8,012,157 B2 | 9/2011 | Chang et al. |
| 8,210,729 B2 | 7/2012 | O'Leary et al. |
| 8,226,659 B2 | 7/2012 | Rabiner et al. |
| 8,246,628 B2 | 8/2012 | Rabiner |
| 8,308,749 B2 | 11/2012 | Johnson et al. |
| 8,328,402 B2 | 12/2012 | O'Leary et al. |
| 8,348,956 B2 | 1/2013 | Rabiner |
| 8,366,711 B2 | 2/2013 | Rabiner et al. |
| 8,403,968 B2 | 3/2013 | Rabiner et al. |
| 8,431,074 B2 | 4/2013 | Neer |
| 8,475,732 B2 | 7/2013 | Simmons et al. |
| 8,512,338 B2 | 8/2013 | Rabiner et al. |
| 8,523,901 B2 | 9/2013 | Rabiner et al. |
| 8,574,233 B2 | 11/2013 | Rabiner et al. |
| 8,668,701 B2 | 3/2014 | Rabiner et al. |
| 8,672,982 B2 | 3/2014 | Rabiner et al. |
| 8,684,965 B2 | 4/2014 | Rabiner et al. |
| 8,734,460 B2 | 5/2014 | Rabiner et al. |
| 8,777,950 B2 | 7/2014 | Colleran et al. |
| 8,870,965 B2 | 10/2014 | Rabiner et al. |
| 8,906,030 B2 | 12/2014 | Rabiner et al. |
| 8,906,031 B2 | 12/2014 | Rabiner et al. |
| 8,915,966 B2 | 12/2014 | Rabiner et al. |
| 8,936,382 B2 | 1/2015 | O'Leary et al. |
| 8,936,644 B2 | 1/2015 | Rabiner et al. |
| 8,939,977 B2 | 1/2015 | DiPoto et al. |
| 9,005,254 B2 | 4/2015 | Rabiner et al. |
| 9,050,079 B2 | 6/2015 | Rabiner et al. |
| 9,101,419 B2 | 8/2015 | Colleran et al. |
| 9,125,706 B2 | 9/2015 | Rabiner et al. |
| 9,144,442 B2 | 9/2015 | Rabiner et al. |
| 9,179,959 B2 | 11/2015 | Rabiner et al. |
| 9,216,049 B2 | 12/2015 | Rabiner et al. |
| 9,254,156 B2 | 2/2016 | Rabiner |
| 9,254,195 B2 | 2/2016 | Rabiner et al. |
| 9,265,549 B2 | 2/2016 | Rabiner |
| 9,427,289 B2 | 8/2016 | Rabiner et al. |
| 9,433,450 B2 | 9/2016 | Rabiner et al. |
| 9,808,647 B2 | 11/2017 | Rhodes et al. |
| 9,999,456 B2 | 6/2018 | Powell et al. |
| 10,226,642 B2 | 3/2019 | Rabiner et al. |
| 10,238,890 B2 | 3/2019 | Rhodes et al. |
| 10,307,612 B2 | 6/2019 | Barneck et al. |
| 10,471,277 B2 | 11/2019 | Rhodes et al. |
| 10,543,338 B2 | 1/2020 | Barneck et al. |
| 10,729,916 B2 | 8/2020 | Barneck et al. |
| 10,870,015 B2 | 12/2020 | Barneck et al. |
| 10,894,173 B2 | 1/2021 | Barneck et al. |
| 11,154,724 B2 | 10/2021 | Rabiner et al. |
| 11,229,728 B1 | 1/2022 | Barneck et al. |
| 11,229,808 B2 | 1/2022 | Barneck et al. |
| 11,241,585 B2 | 2/2022 | Long et al. |
| 11,259,847 B2 | 3/2022 | Rabiner et al. |
| 2001/0055462 A1 | 12/2001 | Seibel |
| 2002/0091424 A1 | 7/2002 | Biel |
| 2003/0055483 A1 | 3/2003 | Gumm |
| 2003/0093145 A1 | 5/2003 | Lawrence-Brown et al. |
| 2004/0166018 A1 | 8/2004 | Clark et al. |
| 2005/0101854 A1 | 5/2005 | Larson et al. |
| 2006/0004317 A1 | 1/2006 | Mauge et al. |
| 2006/0100547 A1 | 5/2006 | Rabiner et al. |
| 2007/0255287 A1 | 11/2007 | Rabiner |
| 2008/0039770 A1 | 2/2008 | Francis et al. |
| 2008/0039854 A1 | 2/2008 | Rabiner |
| 2008/0125784 A1 | 5/2008 | Rabiner et al. |
| 2009/0048629 A1 | 2/2009 | Rabiner |
| 2009/0054900 A1 | 2/2009 | Rabiner et al. |
| 2009/0112196 A1 | 4/2009 | Rabiner et al. |
| 2009/0171358 A1 | 7/2009 | Chang et al. |
| 2009/0177204 A1 | 7/2009 | Colleran et al. |
| 2009/0187192 A1 | 7/2009 | Rabiner et al. |
| 2010/0160838 A1 | 6/2010 | Krespi |
| 2010/0234925 A1 | 9/2010 | Harris et al. |
| 2010/0256641 A1 | 10/2010 | Rabiner et al. |
| 2010/0262069 A1 | 10/2010 | Rabiner et al. |
| 2010/0262188 A1 | 10/2010 | Rabiner et al. |
| 2010/0265733 A1 | 10/2010 | O'Leary et al. |
| 2010/0268151 A1 | 10/2010 | Mauge et al. |
| 2010/0331850 A1 | 12/2010 | Rabiner |
| 2011/0004213 A1 | 1/2011 | Rabiner et al. |
| 2011/0009871 A1 | 1/2011 | Rabiner |
| 2011/0046746 A1 | 2/2011 | Rabiner et al. |
| 2011/0098713 A1 | 4/2011 | Rabiner et al. |
| 2011/0213339 A1 | 9/2011 | Bak |
| 2011/0313356 A1 | 12/2011 | Rabiner et al. |
| 2012/0065643 A1 | 3/2012 | Rabiner et al. |
| 2012/0100601 A1 | 4/2012 | Simmons et al. |
| 2012/0150190 A1 | 6/2012 | Rabiner |
| 2012/0165941 A1 | 6/2012 | Rabiner et al. |
| 2012/0262939 A1 | 10/2012 | O'Leary et al. |
| 2012/0275180 A1* | 11/2012 | Button .................. G02B 6/001 362/558 |
| 2012/0289968 A1 | 11/2012 | Rabiner |
| 2013/0003406 A1 | 1/2013 | O'Leary et al. |
| 2013/0006304 A1 | 1/2013 | Rabiner et al. |
| 2013/0013008 A1 | 1/2013 | Rabiner et al. |
| 2013/0013009 A1 | 1/2013 | Colleran et al. |
| 2013/0013010 A1 | 1/2013 | Rabiner et al. |
| 2013/0023876 A1 | 1/2013 | Rabiner et al. |
| 2013/0023877 A1 | 1/2013 | Rabiner et al. |
| 2013/0023886 A1 | 1/2013 | Rabiner et al. |
| 2013/0041472 A1 | 2/2013 | Rabiner et al. |
| 2013/0046390 A1 | 2/2013 | Rabiner et al. |
| 2013/0066326 A1 | 3/2013 | Rabiner et al. |
| 2013/0158607 A1 | 6/2013 | Rabiner et al. |
| 2013/0184715 A1 | 7/2013 | Rabiner et al. |
| 2013/0274549 A1 | 10/2013 | Natale et al. |
| 2013/0310875 A1 | 11/2013 | Rabiner et al. |
| 2013/0323120 A1 | 12/2013 | Ma |
| 2014/0018806 A1 | 1/2014 | DiPoto et al. |
| 2014/0135847 A1 | 5/2014 | Rabiner et al. |
| 2014/0142581 A1 | 5/2014 | Rabiner et al. |
| 2014/0148813 A1 | 5/2014 | Rabiner et al. |
| 2014/0163453 A1 | 6/2014 | Rabiner et al. |
| 2014/0180288 A1 | 6/2014 | Rabiner et al. |
| 2014/0235942 A1 | 8/2014 | Hellstrom et al. |
| 2015/0057598 A1 | 2/2015 | Bornstein |
| 2015/0066028 A1 | 3/2015 | Rabiner et al. |
| 2015/0066085 A1 | 3/2015 | Rabiner et al. |
| 2015/0080900 A1 | 3/2015 | Rabiner et al. |
| 2015/0088268 A1 | 3/2015 | Rabiner et al. |
| 2015/0231287 A1 | 8/2015 | Lin et al. |
| 2015/0374498 A1 | 12/2015 | Rabiner et al. |
| 2016/0022333 A1 | 1/2016 | Rabiner et al. |
| 2016/0128750 A1 | 5/2016 | Rabiner et al. |
| 2016/0128836 A1 | 5/2016 | Rabiner et al. |
| 2016/0151639 A1 | 6/2016 | Scharf et al. |
| 2017/0128742 A1 | 5/2017 | Rabiner et al. |
| 2019/0168023 A1 | 6/2019 | Eltorai |
| 2019/0175938 A1* | 6/2019 | Rezaie ................. A61B 1/0638 |
| 2020/0000504 A1* | 1/2020 | Rabiner ............. A61B 17/8833 |
| 2020/0206529 A1 | 7/2020 | Rhodes et al. |
| 2020/0397453 A1 | 12/2020 | McGowan et al. |
| 2022/0000527 A1 | 1/2022 | Rabiner et al. |

(56) References Cited

U.S. PATENT DOCUMENTS

2022/0134129 A1    5/2022   Rabiner et al.
2023/0077399 A1    3/2023   Rabiner et al.

FOREIGN PATENT DOCUMENTS

| WO | WO 2012/148746 A1 | 11/2012 |
| WO | WO 2015/006309 A1 | 1/2015 |
| WO | WO 2016/079365 | 5/2016 |
| WO | WO 2023/028342 | 3/2023 |

* cited by examiner

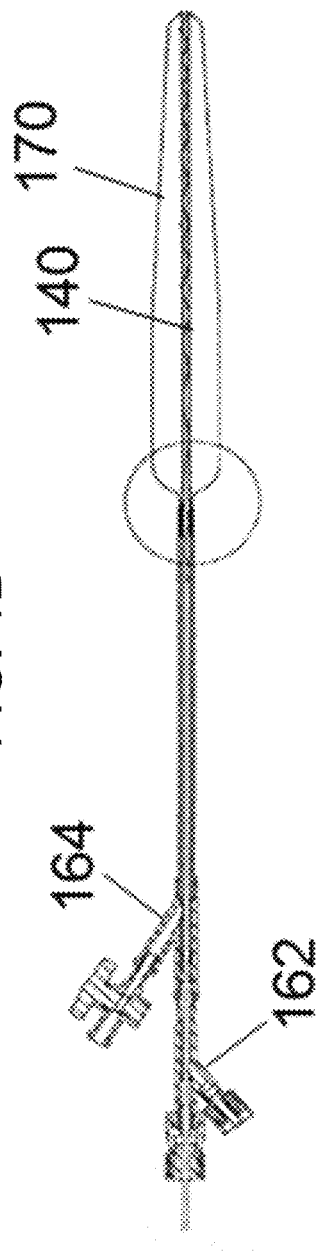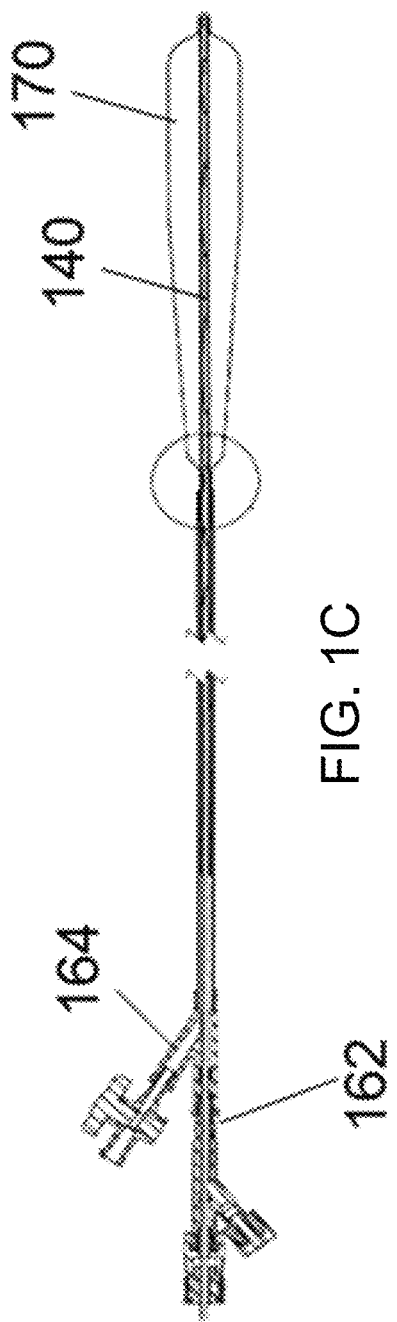

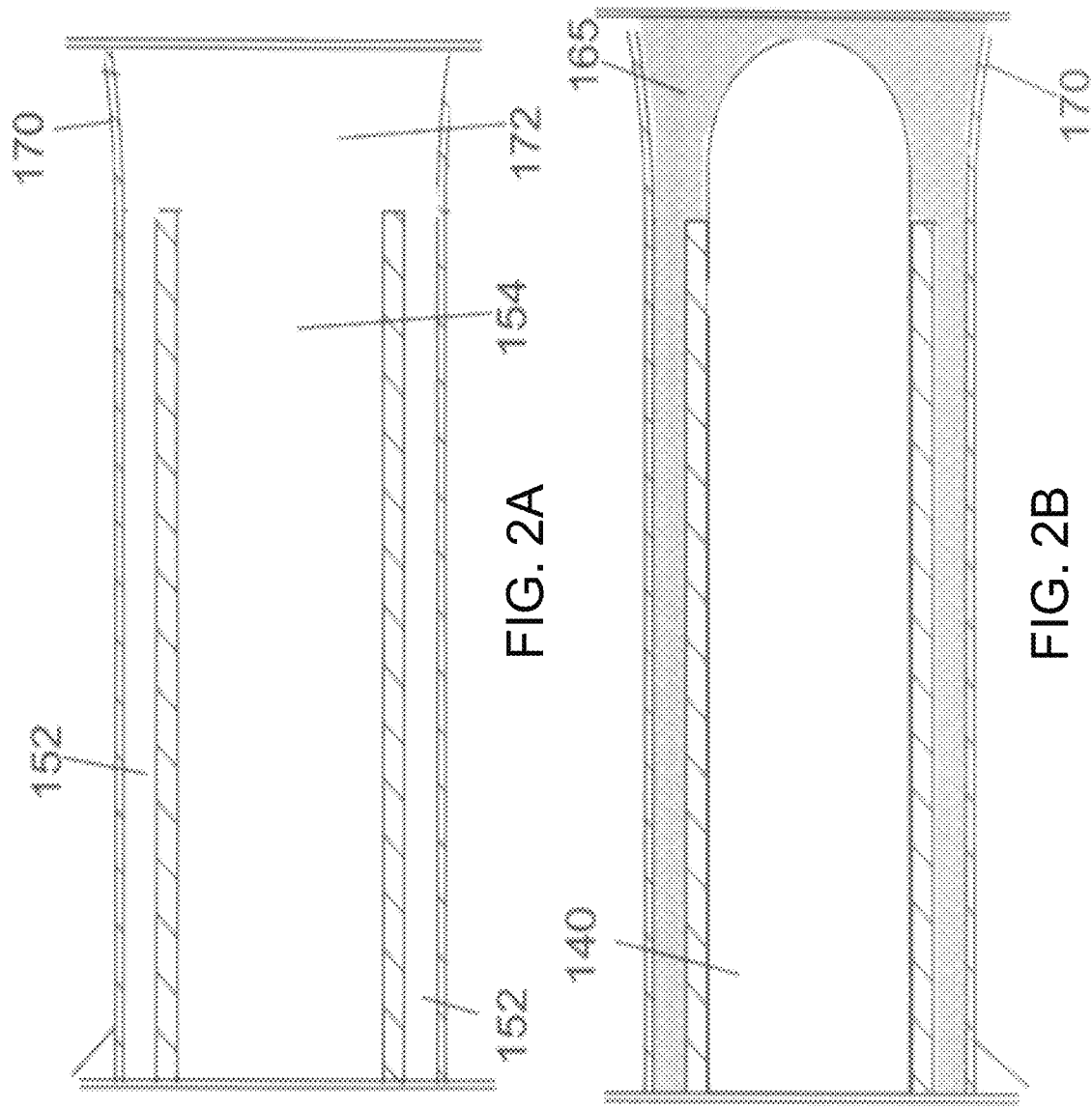

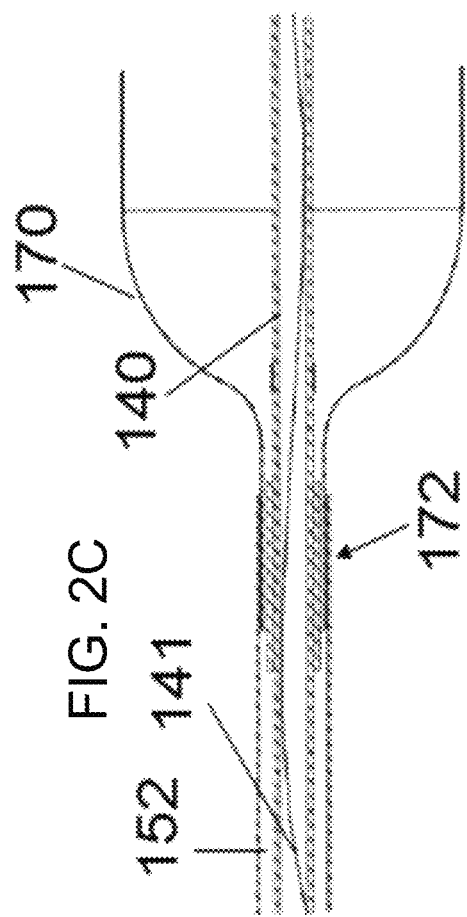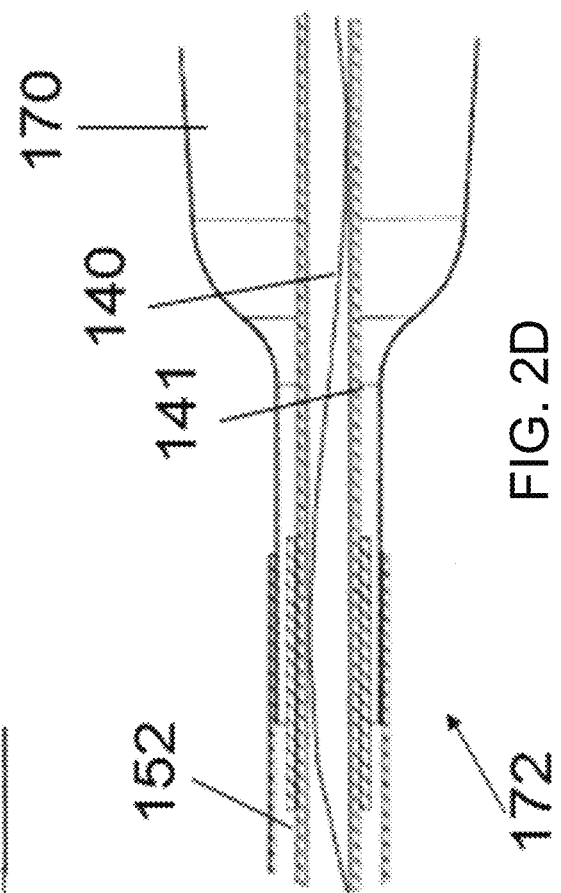

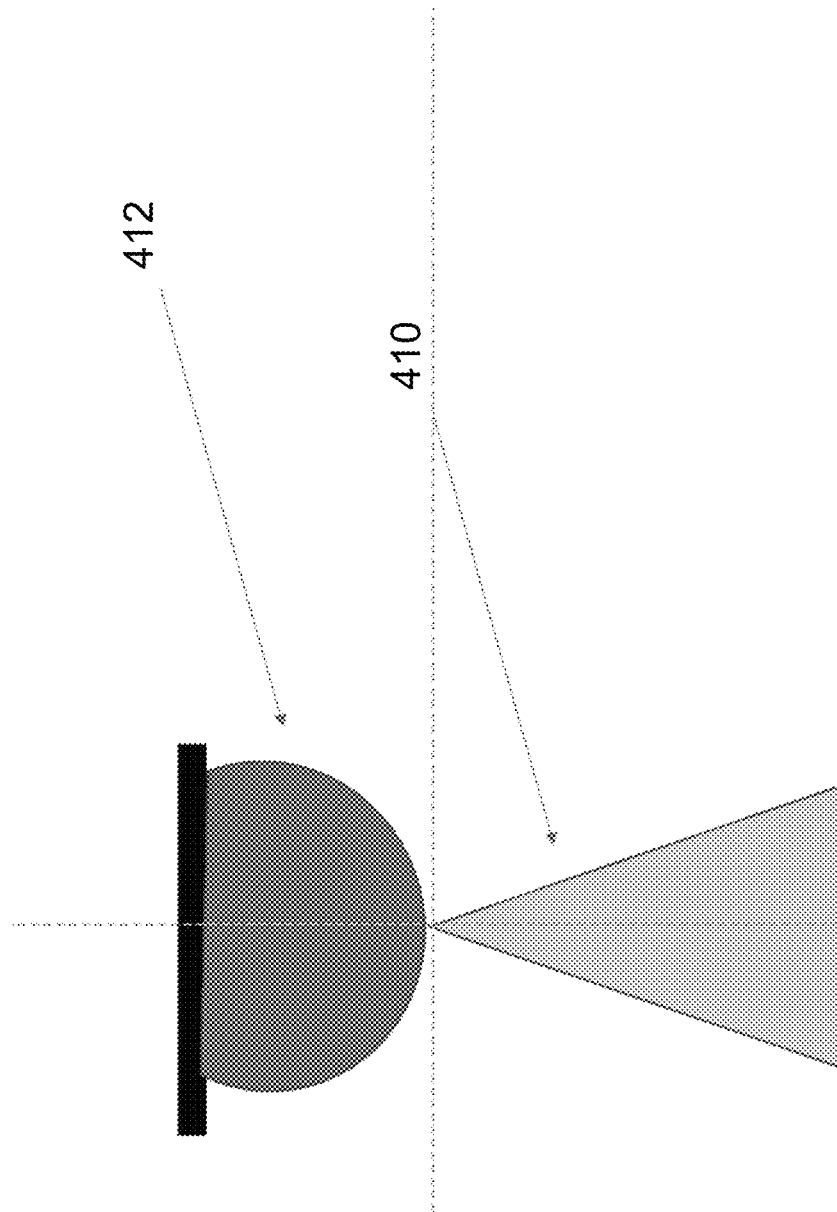

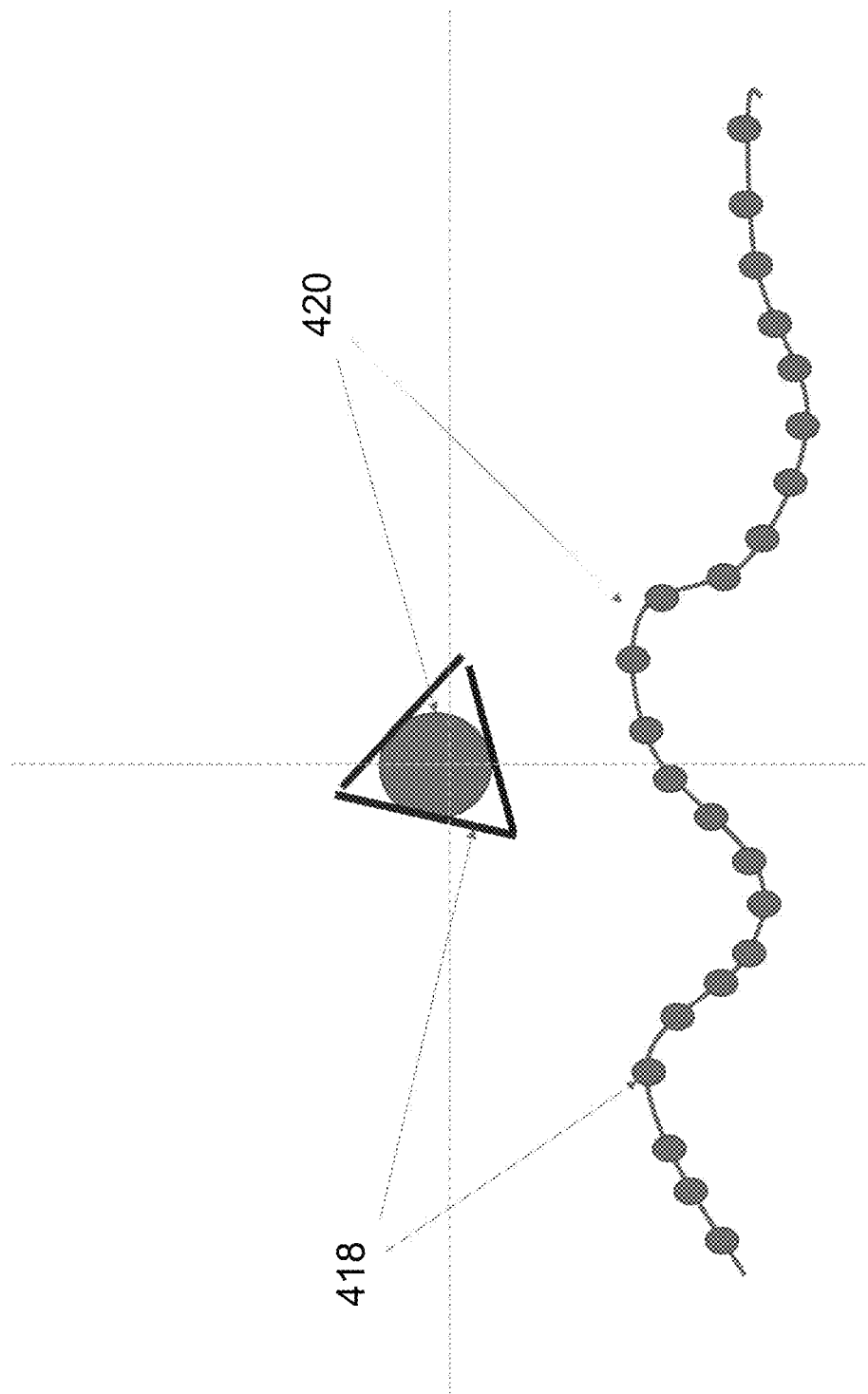

SIDE VIEW OF THE FIBER WITH LIGHT
BOUNCING OFF THE CLADDING ( Snells Law )

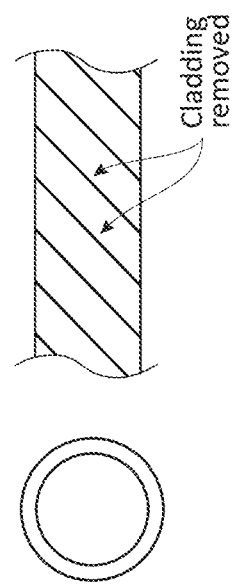
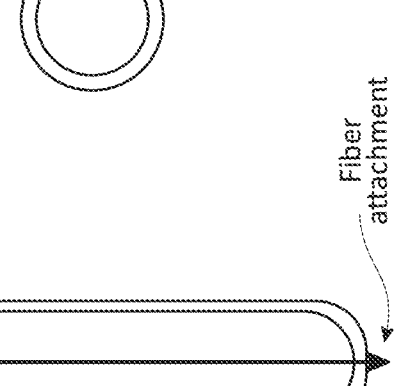
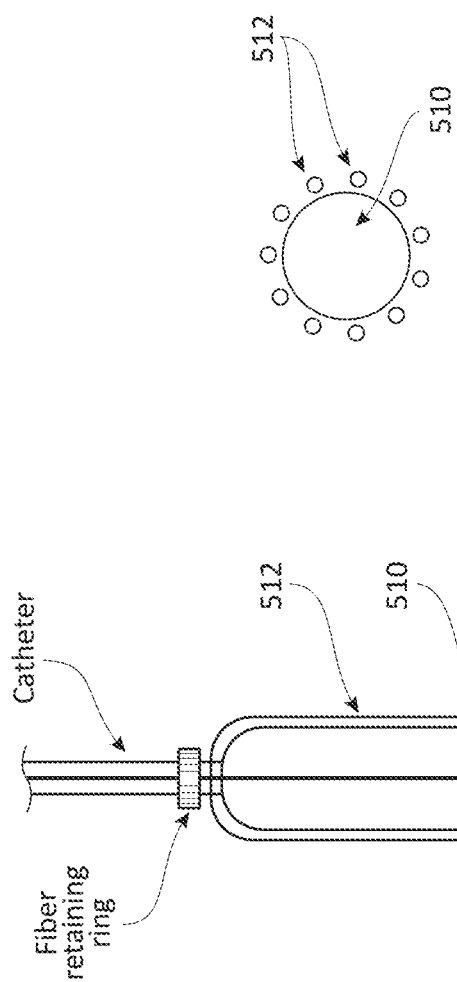

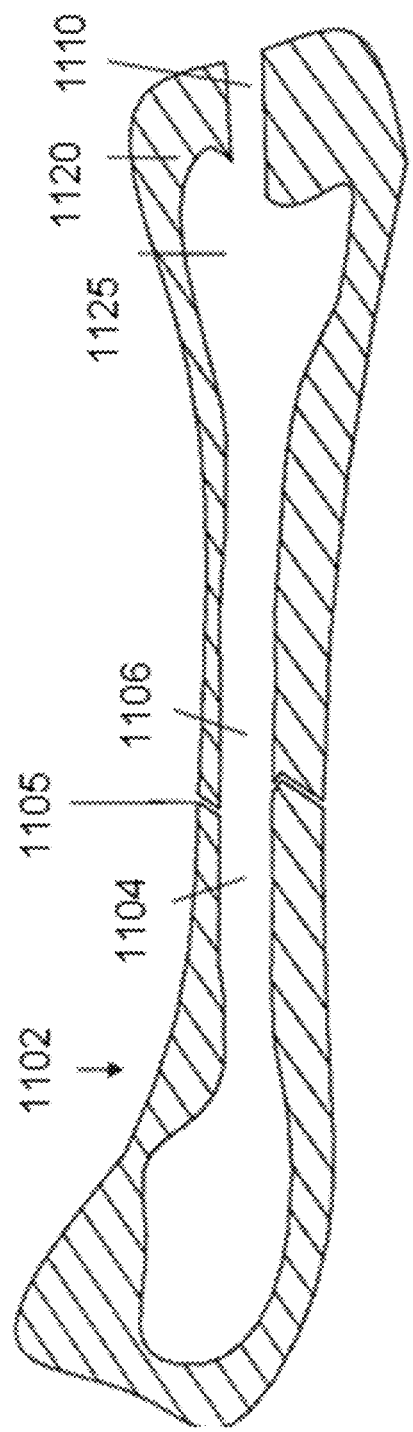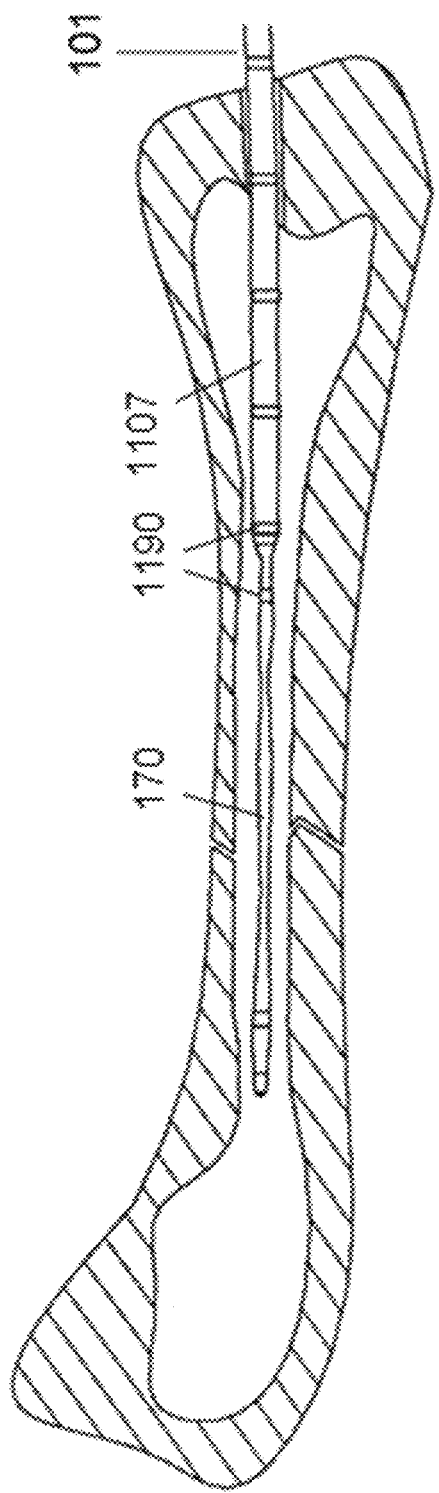
FIG. 34A
FIG. 34B

Studies on the in vitro antimicrobial effect of blue light

| Light Source | Radiant exposure | Bacterial species/strains | Inactivation efficacy | Ref |
|---|---|---|---|---|
| 405 nm diode laser | 20 J/cm$^2$ | H. pylori | >99.9% | 225 |
| 405 nm light-emitting diode | 15 J/cm$^2$ at lamp aperture | P. gingivalis | >75% | 223 |
| 380–520 nm broadband light | 4.2–4.2 J/cm$^2$ | P. gingivalis, P. intermedia, P. nigrescens, P. eikenogenica, S. constellatus | P. intermedia and P. nigrescens: >5 log10 at 4.2 J/cm$^2$, P. melaninogenica: >5 log10 at 21 J/cm$^2$, P. gingivalis 1.83 log10 at 40 J/cm$^2$ | 228 |
| 400–500 nm blue lamps | 260 and 1300 mW/cm$^2$ for up to 3 min | P. gingivalis, F. nucleatum, S. mutans, E. faecalis | The minimal inhibitory dose for P. gingivalis and F. nucleatum was 16–62 J/cm$^2$, for S. mutans and S. faecalis was 159–212 J/cm$^2$ | 229 |
| 405 and 470 nm light | 15 J/cm$^2$ | S. aureus, P. aeruginosa | S. aureus: 90% at 405 nm, 63% at 470 nm, P. aeruginosa 95.1% at 405 nm, 96.5% at 470 nm | 230 |
| 407–420 nm | | five P. acnes strains | decreased by 15.7% immediately and 24.4% at 60 min after the irradiation | 231 |
| 407–420 nm | 75 J/cm$^2$ | P. acnes | less than 2-log10 units (99%) after two illuminations and by 5-log10 units (99.999%) after three illuminations | 281 |

FIG. 39G

ANTI-MICROBIAL BLUE LIGHT SYSTEMS AND METHODS

RELATED APPLICATIONS

This application is a continuation application of U.S. Non-Provisional application Ser. No. 17/896,902, filed on Aug. 26, 2022, now U.S. Pat. No. 11,813,368, which claims the benefit of and priority to U.S. Provisional Application No. 63/264,174, filed on Nov. 17, 2021, and U.S. Provisional Application No. 63/238,104, filed on Aug. 27, 2021, and the contents of each of these applications are hereby incorporated herein by reference in their entireties.

FIELD

The embodiments disclosed herein relate to treatments for bones, and more particularly to anti-microbial blue light systems and methods for providing an anti-microbial, anti-bacterial effect for medical applications.

BACKGROUND

Bones form the skeleton of the body and allow the body to be supported against gravity and to move and function in the world. Bone fractures can occur, for example, from an outside force or from a controlled surgical cut (an osteotomy). A fracture's alignment is described as to whether the fracture fragments are displaced or in their normal anatomic position. In some instances, surgery may be required to re-align and stabilize the fractured bone. A bone infection may occur when bacteria or fungi invade the bone, such as when a bone is fractured or from bone fracture repair. These bacteria commonly appear and if not addressed properly can cause server health problems. It would be desirable to have an improved systems and methods for eliminating bacteria or other pathogens.

SUMMARY

The present disclosure is directed to systems, devices, and methods for providing treatment to tissue. In some embodiments, the system can include a delivery catheter having an elongated shaft and an inner lumen therethrough and one or more optical fibers sized to pass through the inner lumen of the delivery catheter and being configured to directly deliver light energy to provide an antimicrobial effect to the tissue. The one or more optical fibers are configured to disperse the light energy evenly over a length of the one or more optical fibers in both longitudinal and circumferential directions. The antimicrobial effect of the light energy is configured to kill bacteria, viruses, or fungus to treat bone infections. The antimicrobial effect of the light energy is configured to reduce an amount of one or more pathogens in a bone.

In some embodiments, the one or more optical fibers include a cladding covering an outer surface thereof, and at least a portion of the cladding of the one or more optical fibers is removed from an outer surface of the one or more optical fibers to achieve the even dispersion of the light energy. In some embodiments, the at least a portion of the cladding is removed to form a helical spiral along the length of the one or more optical fibers. In some embodiments, the helical spiral becomes increasingly tight as the helical spiral moves from a proximal end of the one or more optical fibers to a distal end of the one or more optical fibers to achieve an even light distribution over the length of the one or more optical fibers. In some embodiments, a depth of the removal of the cladding increases as the helical spiral moves from a proximal end of the one or more optical fibers to a distal end of the one or more optical fibers to achieve an even light distribution over the length of the one or more optical fibers. In some embodiments, the helical spiral allows for dispersion of light energy around 360 degrees of the one or more optical fibers.

In some embodiment, the one or more optical fibers includes a diffusive membrane disposed on an outer surface thereof, the diffusive membrane configured to be applied to the outer surface of the one or more optical fibers to achieve the even light distribution over the length of the one or more optical fibers.

In some embodiments, the light energy has illumination wavelengths from about 400 nm to about 475 nm. In some embodiments, the light energy has illumination wavelengths from about 380 nm to about 500 nm. In some embodiments, the light energy has illumination wavelengths from about 405 nm to about 470 nm.

In some embodiments, a system for providing treatment to tissue is provided and can include a light source configured to provide light energy at a plurality of frequencies, a delivery catheter having an elongated shaft and an inner lumen therethrough, and one or more optical fibers sized to pass through the inner lumen of the delivery catheter and being configured to directly deliver the light energy from the light source to provide an antimicrobial effect to the tissue. The one or more optical fibers are configured to disperse the light energy evenly over a length of the one or more optical fibers in both longitudinal and circumferential directions. The antimicrobial effect of the light energy is configured to reduce an amount of, remove, kill or eliminate one or more pathogens in a bone.

In some embodiments, the plurality of frequencies of the light energy are selected based on the antimicrobial effect on specific microbial targets for each of the plurality of frequencies of light energy. In some embodiments, a subset of the plurality of frequencies of light energy can be used based on the specific microbial targets. In some embodiments, the light energy has illumination wavelengths from about 400 nm to about 475 nm. In some embodiments, the light source is in the form of a chain of a plurality of LEDs such that the chain of the plurality of LEDs can produce even light dispersion over the length of the chain.

In some embodiments, the one or more optical fibers include a cladding covering an outer surface thereof, and wherein at least a portion of the cladding of the one or more optical fibers is removed from an outer surface of the one or more optical fibers to achieve the even dispersion of the light energy. In some embodiments the at least a portion of the cladding is removed to form a helical spiral along the length of the one or more optical fibers.

In some embodiments, a method for treating tissue is provided and can include the steps of delivering a catheter to a tissue, delivering one or more optical fibers through the catheter to the tissue, activating a light source engaging the one or more optical fibers, and delivering light energy from the light source to the one or more optical fibers to provide an antimicrobial effect to the tissue. The one or more optical fibers can disperse the light energy evenly over a length of the one or more optical fibers in both longitudinal and circumferential directions.

In some embodiments the light source includes a plurality of frequencies of the light energy. In some embodiments, the method can further include selecting one or more of the plurality of frequencies of light energy to activate based on the antimicrobial effect on specific microbial targets. In some embodiments the light energy has illumination wavelengths from about 400 nm to about 475 nm.

BRIEF DESCRIPTION OF THE DRAWINGS

The presently disclosed embodiments will be further explained with reference to the attached drawings, wherein like structures are referred to by like numerals throughout the several views. The drawings shown are not necessarily to scale, with emphasis instead generally being placed upon illustrating the principles of the presently disclosed embodiments.

FIG. 1B and FIG. 1C show exemplary embodiments of a bone implant device that includes a delivery catheter and an expandable member sufficiently shaped to fit within a space, cavity or a gap in a fractured bone;

FIG. 2A shows a close-up cross-sectional view of the region circled in FIG. 1A of the distal end of the delivery catheter and the expandable member prior to the device being infused with a fluid;

FIG. 2B shows a close-up cross-sectional view of the region circled in FIG. 1A of the distal end of the delivery catheter and the expandable member after the device has been infused with fluid and light energy from the light-conducting fiber is introduced into the delivery catheter;

FIG. 2C and FIG. 2D each show a close-up cross-sectional view of the regions circled in FIG. 1B and FIG. 1C, respectively, showing the distal end of the delivery catheter and the expandable member and a light-conducting fiber in the delivery catheter and inner lumen of the expandable member;

FIG. 8, FIG. 9, and FIG. 10 are exemplary embodiments of an LED with a reflecting member;

FIG. 11 is an exemplary embodiment of a plurality of LEDs connected together on a string for delivering light energy to a treatment site;

FIG. 25A illustrates an exemplary embodiment of a balloon catheter having one or more fibers positioned on the outside thereof;

FIG. 25B illustrates a top view an exemplary embodiment of a balloon catheter having one or more fibers positioned on the outside thereof;

FIG. 25C illustrates an exemplary fiber with a portion of cladding removed therefrom;

FIG. 27 shows an exemplary embodiment of an expandable member having ridges located on an outer surface, wherein the ridges include at least one channel for the optical fibers to enter there through;

FIG. 34A, FIG. 34B, FIG. 34C, FIG. 34D and FIG. 34E provide embodiment methods for delivering light and/or implanting an intramedullary implant within the intramedullary space of a weakened or fractured bone;

FIG. 39A, FIG. 39B, FIG. 39C, FIG. 39D, FIG. 39E, FIG. 39F, and FIG. 39G show an experimental set up;

Figure 1A:
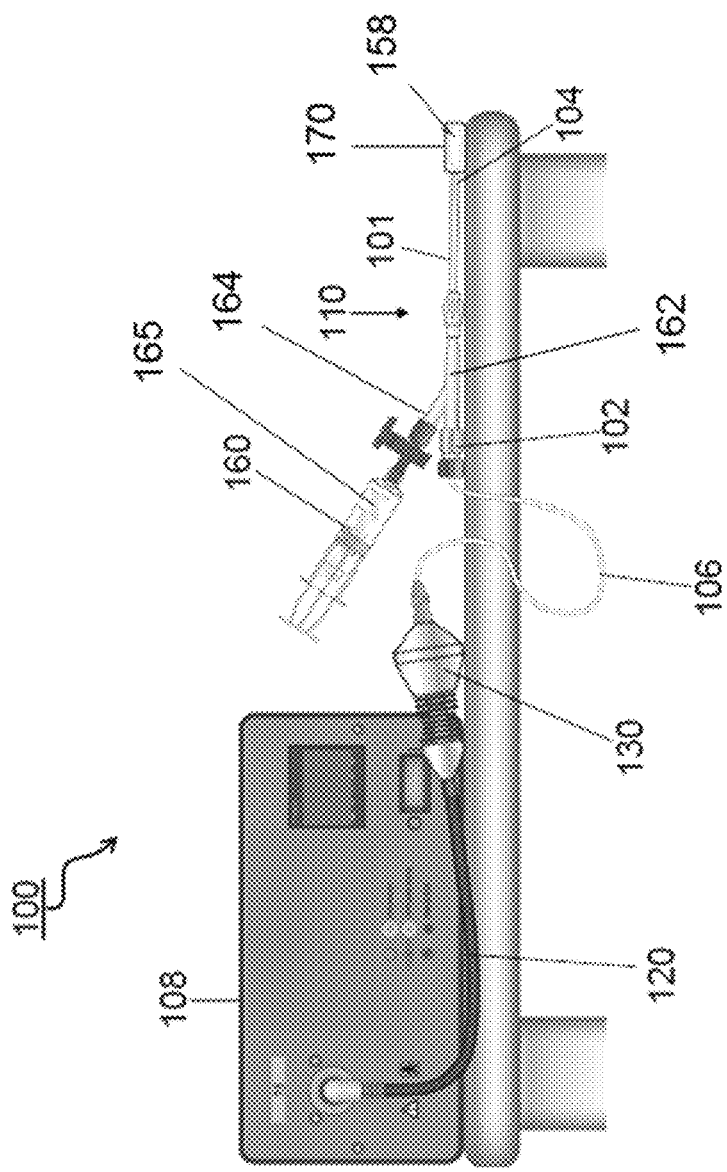
FIG. 1A shows a schematic illustration of an exemplary embodiment of a bone implant system.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

Systems and methods for antimicrobial blue light photolysis (ABLP) for intramedullary treatment of bone infections and disorders are disclosed herein. In some embodiments, devices and methods including stabilization and providing an anti-microbial effect for bone restructuring are disclosed. An anti-microbial effect may also include a bactericidal effect or an anti-bacterial effect, among other things. In some embodiments, the ABLP systems and methods can be used in conjunction with bone fracture fixation methods or other orthopedic procedures. For example, light for providing an anti-microbial, anti-bacterial effect can be used in a variety of medical applications, including but not limited to surgery, interventional radiology, respiratory and airway management, gynocology, dermatology, infectious diseases, wound care, and orthopedics.

Methods and systems for the controlled delivery intramedullary of blue light (frequency about 380-500 nm) for the treatment of osteomyelitis via a small diameter flexible fiber where the light is delivered in a circumferential fashion around the fiber, and where the energy delivered from the fiber is of a same average intensity at the front end of the fiber as it was in the back end of the fiber. The methods and systems deliver intramedullary light to the canal over long lengths via a small diameter, minimally invasive pathway to a bone. The methods and systems deliver and maintain a light delivery system within the canal of the bone to provide single or multiple doses of the light, potentially without removal of the light fiber system, thereby enhancing the ease of multiple treatments that may be required. In some embodiments, a port may be created and the instrument for the application of light redelivered into the canal. The controlled delivery of blue light in frequencies that can cause the death of the bacteria that causes infections can be achieved. The use of light in the formation and transfer of molecular oxygen on a cellular level, forming a reactive singlet oxygen, where this oxidizing species can destroy proteins, lipids, and nucleic acids causing cell death and tissue necrosis. The methods and systems provide secondary fluids, e.g., $H_2O_2$, that will enhance the death of the bacteria, wherein the blue light has weakened/damaged the outer shell of the bacteria, and the $O_2$ from the peroxide accomplishes the final oxidation destroying/causing the death of the bacteria.

System and methods for providing an anti-microbial effect on a bone are disclosed. According to aspects of the disclosed subject matter, a system for providing an anti-microbial effect on a bone includes a delivery catheter having an elongated shaft with a proximal end, a distal end, and a longitudinal axis therebetween, an inner void for passing at least one light sensitive liquid, and an inner lumen, an expandable member releasably engaging the distal end of the delivery catheter, the expandable member capable of moving from a deflated state to an inflated state by infusing at least one light sensitive liquid into the expandable member, and a light conducting fiber sized to pass through the inner lumen of the delivery catheter and into the expandable member. In some embodiments, when the light conducting fiber is in the expandable member, the light conducting fiber is able to initiate hardening of the at least one light sensitive liquid within the expandable member to form a photodynamic implant and the light conducting fiber is able to disperse light energy to provide an anti-microbial effect to the bone. The use of light to cure a monomer could be a secondary application of the system.

In some embodiments, the systems and methods described here can be used for the intermedullary treatment of orthopedic osteomyelitis, which is inflammation or swelling that occurs in the bone. Osteomyelitis can result from an infection somewhere else in the body that has spread to the bone, or osteomyelitis can start in the bone, often as a result of an injury. Osteomyelitis is more common in younger children (five and under) but can happen at any age. Osteomyelitis more commonly affects people younger than 20, or adults older than 50 years of age. While there is a higher incidence of bone infections in adults that live in developing countries, hemodialysis patients, injection drug users, and patients with certain chronic conditions such as diabetes are also more susceptible to this infection. Bones can become infected in a number of ways, including through bacteria or an infection in one part of the body that may spread through the bloodstream into bone, or an open fracture or surgery, such as hip, shoulder or knee replacement surgery, that may expose bone to infection.

The systems and methods herein can also be helpful in the destruction of biofilm as the blue light can be used to break down the surface bacteria.

ABLP can be used in a variety of procedures. In some embodiments, ABLP can be used in minimally invasive surgical procedures. In some embodiments, ABLP can be used for the use and delivery during intraabdominal procedures delivered via a trocar or cannula. In some embodiments, ABLP can be used for the use and delivery in arthroscopic procedures delivered via a trocar cannula. In some embodiments, ABLP can be used for the use in treating wound infections. In some embodiments, ABLP can be used for the use in the treatment of "open" surgical procedures.

A medical device disclosed herein may be used for treating conditions and diseases of the bone, including, but not limited to, the femur, tibia, fibula, humerus, ulna, radius, metatarsals, phalanx, phalanges, ribs, spine, vertebrae, clavicle and other bones and still be within the scope and spirit of the disclosed embodiments.

Blue light has demonstrated antimicrobial properties against a range of microbes, including but not limited to gram-positive and gram-negative bacteria, mycobacteria, molds, yeasts, dermatophytes, and similar pathogens. Antimicrobial blue light having wavelengths between about 400 nm to about 470 nm can be used as alternative to antibiotics.

The basic electrodynamics of photosensitized reactions involves the absorption of photons by the ground-state PS, causing electrons to be pumped to an excited singlet state. The excited-state PS can then engage in several different reactions that are destructive to microbes, such as electron transfer reactions and the formation of radicals, including the potent hydroxyl radical (Type I, redox reactions). A second activation pathway (Type II, peroxidation reactions) also exists, by which energy transfers via forbidden transition from the PS singlet state to an intermediate triplet state, a feature of only certain dyes like methylene blue (MB). Because surrounding oxygen molecules are one of the few biological molecules that exist in a naturally occurring triplet ground-state, the oxygen can absorb, or "quench" the PS triplet state energy in a non-radiative exchange process. The oxygen molecules then pump to their own singlet state forming highly reactive singlet oxygen.

Singlet oxygen is one of most powerful oxidative species known, and when generated in close proximity to bacterial membranes, rapidly results in membrane perforation, protein cross-linking, and consequent cell death. It has been demonstrated that singlet oxygen can exert potent cytotoxic effects on microbes without being internalized. The singlet oxygen lifetime in biological media is short, and this short active lifetime localizes the kill to the immediate vicinity of the activated molecule.

The most effective antimicrobial photosensitizers are positively charged (cationic) which permits them to bind to negatively-charged (anionic) microbial cell membranes. These cationic PS's bind poorly to zwitterionic (net neutral) human cells which are therefore protected from damage (Loebel et al, 2016). The destructive reactions caused by singlet oxygen are relatively selective for the organisms to which the PS adheres. The destructive effect is further amplified by the PDT "bystander" effect (Alexandre et al, 2007), a cooperative inactivation process between cells in a given microcolony, most likely mediated by microbicidal photoproducts or the transfer of lysosomal enzymes from nearby cells. Broad-spectrum activity against viruses is rapid and potent; here the active cidal mechanism involves diffusion-limited penetration across the envelope or capsid, followed by covalent cross-linking and destruction of side chains and backbone sites at multiple positions on viral proteins; downstream chain reactions causing aggregation, altered conformation and directly oxidized guanosine residues; and cross-linking, scission and irreversible oxidation of DNA and RNA with high second-order rate constant.

System Overview

According to embodiments of the present disclosure, the device, system and methods disclosed provide, among other things, a site-specific treatment approach to target a specific infection area within a bone. For example, in some embodiments, the site-specific treatment approach is designed to provide treatment in the endosteal, i.e. inside surface of the bone, so as to treat infection in the bone from the medullary canal, i.e. from the inside to the outside. This is contrast to treatments using antibiotics to fight infection; the treatment used of antibiotics results in a systemic broad approach towards treating the infection, which is not a targeted site-specific treatment as per the instant disclosure. For example, after an invasive surgical procedure an infection may develop in the patient, requiring the patient to undergo antibiotic treatment. Treatments using antibiotics are delivered either orally or by infusion, wherein such broad treatment goes towards an entire anatomical treatment of the body. For example, even during the course of this broad treatment using antibiotics, the specific area of the actual infection may not be properly treated and/or as a result this broad treatment likely will deliver more drugs than is required to treat the specific infection area or mall area. The present disclosure is directed to a site-specific approach by applying light to the specific infection area to kill the infected matter or bacteria. In some embodiments, the present disclosure can result in providing direct treatment to an infection area, using only an amount of treatment necessary to kill the infection, i.e., which is in contrast to the broad treatment approach of using antibiotics. In some embodiments, the use of light to treat an infection can result in only an additional small amount of antibiotic as a "clean-up" that may be required. In some embodiments, at least one aspect of the site specific treatment results in a faster "kill" or termination of the infection versus the broad treatment approach of using the systematic drug, i.e. antibiotics.

In some embodiments, the device, systems and methods disclosed provide an anti-microbial effect on and/or in bones. In some embodiments, the device, systems and methods disclosed herein can provide an anti-microbial effect for orthopedic procedures. In some embodiments, the device, systems and methods disclosed herein can provide a bactericidal effect on and/or in tissue or bones and surrounding tissue. In some embodiments, the device, systems and methods disclosed herein can provide an anti-bacterial effect on and/or in tissue or bones and surrounding tissue. In some embodiments, the device, systems and methods disclosed herein can provide an anti-infective effect on and/or in tissue or bones and surrounding tissue. In some embodiments, the device, systems and methods disclosed herein can provided an anti-fungal effect on and/or in tissue or bones and surrounding tissue.

In some embodiments, the device, system and methods disclosed provide for an application of light to kill the infection which creates the formation and transfers energy to molecular oxygen, thus forming the reactive singlet oxygen. This oxidizing species can destroy proteins, lipids, and nucleic acids causing cell death and tissue necrosis. The instant disclosure's application of light creates molecular oxygen, thus forming the reactive porphyrins. For example, during treatment, electromagnetic radiation having wavelengths in the visible spectrum (i.e., visible light above 395 nm, by non-limiting example) reacts with naturally produced and/or concentrated "endogenous" chromophores (porphyrins). At least one effect of the application of the electromagnetic radiation (illumination) is that the light in conjunction with or in combination with the porphyrins produces necrosis or cell death to the bacteria as evidenced by the microorganism's inability to divide. It is noted that the application of treatment of the instant disclosure provides treatment without the addition of ancillary drugs or chemicals, which can be considered as a "holistic" killing treatment or approach to fighting infection.

As a light-based disinfection approach, antimicrobial blue light (aBL), particularly in the wavelength range of 400-500 nm, has an intrinsic antimicrobial effect. Compared to traditional photodynamic therapy, aBL therapy excites the endogenous chromophores of bacteria, and thus does not require the addition of exogenous photosensitizers. Furthermore, in comparison to ultraviolet irradiation, aBL shows much less detrimental effects in mammalian cells. The bactericidal activity of aBL is non-specific, and many microbial cells, including various antibiotics resistant strains, are highly sensitive to this treatment. aBL therapy has previously shown promise as a treatment for various clinical pathogens, including, but not limited to *Pseudomonas aeruginosa, Acinetobacter baumannii*, methicillinresistant *Staphylococcus aureus* (MRSA), and *Candida albicans*, and other pathogens.

In some embodiments, the device, system and methods disclosed provide for an application that can be used as a self-standing instrument to "wand" the canal of the bone or as a part of a balloon (with monomer) to both stabilize and kill the infection, i.e. providing a site specific treatment approach. The transparency of the monomer increases as it is illuminated with light, allowing more light therethrough. It is possible that treatment for an infection within a canal of the bone may only include using a balloon placed within the canal and merely introducing the application of light disclosed in the present disclosure to treat or kill the infection area. For example, the use of the balloon can provide at least one benefit, in that the expanded balloon acts as filler within the canal compressing and causing the remaining medullary canal materials to be displaced and putting the balloon in direct apposition to the medullary canal wall. Whereby, the results of the application of the balloon within the medullary canal allow for an environment for an appropriate transmission or application of light to kill bacteria in the infection area. For example, failure to displace the medullary canal materials would result in an occluded canal, which would be preclusive to light meeting the bone walls or endosteal surface, thus failure in treating the infection area.

Further, the use of light in accordance with the present disclosure can provide for the termination of newer and more virulent strains of drug resistant bacteria, i.e. "super bugs". Traditional antibiotic methods of killing infections using antibiotic fails to kill virulent strains of drug resistant bacteria, i.e. super bugs. Traditional antibiotic methods kill using a chemical and biologic response associated with O2, i.e. necrosis and cell inability to divide and replicate. As noted above, the present disclosure incorporates the application of light which causes the formation of porphyrins, wherein the application of electromagnetic radiation (illumination) in conjunction with or in combination with the porphyrins, produces necrosis or cell death to the bacteria as evidenced by the microorganism's inability to divide. Further, as noted above, the application of electromagnetic radiation (illumination) according to the present disclosure presents a treatment of the infection area from inside the bone to outward.

In some embodiments, the light intensity will be uniform over the entire length of the one or more optical fibers used to deliver the blue light to the treatment site. This can be achieved, for example, by removing the cladding in specific configurations such that the intensity of light that is passed to the tissue through the areas of the fiber without cladding is uniform along the entire length thereof, as will be explained in more detail below. In some embodiments, this allows light to be emitted down the entire length of the fiber from the side of the fiber to treat any length of tissue.

Illumination Providing an Antimicrobial Effect within Cavities of the Bone

FIG. 1A, FIG. 1B, FIG. 1C, FIG. 2A, FIG. 2B, FIG. 2C and FIG. 2D are schematic illustrations showing various components of an embodiment of a system 100 of the present disclosure. As shown in FIG. 1A, the system 100 includes a light source 108, a light pipe 120, an attachment system 130 and a light-conducting optical fiber 106 having a nonlinear light-emitting portion 158, which emits light from the outside of the optical fiber 106 along its length. The attachment system 130 communicates light energy from the light source 108 to the optical fiber 106. In some embodiments, the light source 108 emits frequency that corresponds to a band in the vicinity of 350 nm to 770 nm, the visible spectrum. In some embodiments, the light source 108 emits frequency that corresponds to a band in the vicinity of 380 nm to 500 nm. In some embodiments, the light source 108 emits frequency that corresponds to a band in the vicinity of 430 nm to 450 nm. In some embodiments, the light source 108 emits frequency that corresponds to a band in the vicinity of 430 nm to 440 nm.

The system 100 includes emitting a beam of a blue light or violet-blue light within a cavity of the bone via an optical fiber for both illuminating towards polymerization as well as towards providing an antimicrobial effect. For example, light from a light source can be used to kill micro-bacteria located within a cavity of a bone before, during and after the healing process of the fractured bone. Steps to kill the micro-bacteria in the cavity of the bone can include emitting the beam of blue light or violet-blue light having a wavelength from about 380 nm to about 500 nm. For example, in some embodiments, broad spectrum visible light.in the range of 400 nm-480 nm can be used. In some embodiments, the light can be generated via a metal halyide bulb, or from a specific frequency LED. In some embodiments, broad spectrum light from 380 nm to 480 nm, inclusive of a small component of UV, can be used. In some embodiments, single spectrum light can be used, i.e., the use of specific frequency LEDs tuned to those frequencies that are known to be specific to certain bacteria. For example, in some embodiments, the blue light/beam can have a wavelength of about 405 nm, about 420 nm, about 450 mm, about 460 nm, or about 470 nm, or any other wavelength that can damage various bacterias. In some embodiments, multiple single spectrums can be used, e.g., 405 nm and 420 nm. The individual frequencies of light can be mixed/focused to provide two or more frequencies within a single fiber. For example, in some embodiments, the blue light/beam can have a wavelength of about 405 nm, about 420 nm, about 450 nm, or about 470 nm.

In some embodiment, more than one LED, such as dual LEDs can be used. This can potentially increase in power as LEDs have a defined amount of power in watts/milliwatts. If more power is required to achieve the antimicrobial effect, the ability to combine more LED illumination power can be useful. The LED illumination can be directed though the use of mirrors, prisms or other optical pathway modifiers that can be brought together, focused and directed through the fiber.

The other rationale for the use of multiple LEDs is selecting frequencies that are known to have an antimicrobial effect on the specific microbial target. It has been shown that some bacteria can be remediated with specific frequencies, while other bacteria are not affected, or are affected at lower levels. Through the ability of merging multiple light frequencies, the user can either pick the appropriate light for the bacteria or can apply multiple frequencies to remediate the bacteria.

Still referring to FIG. 1A, it is contemplated the light source can include a single bulb or multiple bulbs. For purpose of clarity, bulb is used as an indiscriminate description of a light source. A bulb may be a metal halide source, a mercury or xenon incandescent or LED. The type of light source can vary, and can be in the form of one or more LEDs, a laser, or any other potential light source that can provide the desired wavelength of light. The light source may further include one or multiple ports to attach light fibers. The light fibers or light guides may be joined, mixed or include some combination thereof, within the system. Depending upon the application, the light source can be designed to provide higher outputs in different frequencies, i.e. using multiple bulbs, so as to overcome potential fall off aspects that may occur using a single bulb. If multiple bulbs are used, it is contemplated that there may be multiple types of bulbs used in the system. For example, each different type of bulb may provide a specific attribute to meet an intended design aspect for the particular application, which may include attributes relating frequency ranges, energy density ranges, operation life expectancies, etc. Further, regarding other elements within the system where multiple elements of the same element are used, i.e. light fibers (optical fibers, light guides, etc.), light conductive materials and the like, it is contemplated that there may be different types of the same element used within the system. As noted above, each different type of element may be used depending upon the specific attribute to meet an intended design aspect for the particular application, which may include attributes relating material type(s), performance related ranges, operation life expectancies, etc. In conjunction with choosing a specific element, any materials and elements used with that specific element may be further used, so as to meet the intended planned design for the particular application. For example, it is contemplated a clear liquid epoxy may be used to bind and fill in interstices of multiple fibers towards a smooth tube or the like, with the system.

In some embodiments, there can be multiple light sources coupled to different components of the system. For example, a first light source can be coupled to the proximal end of one or more fibers, and a second light source can be coupled to the distal end of the one or more fibers.

Figure 3A:
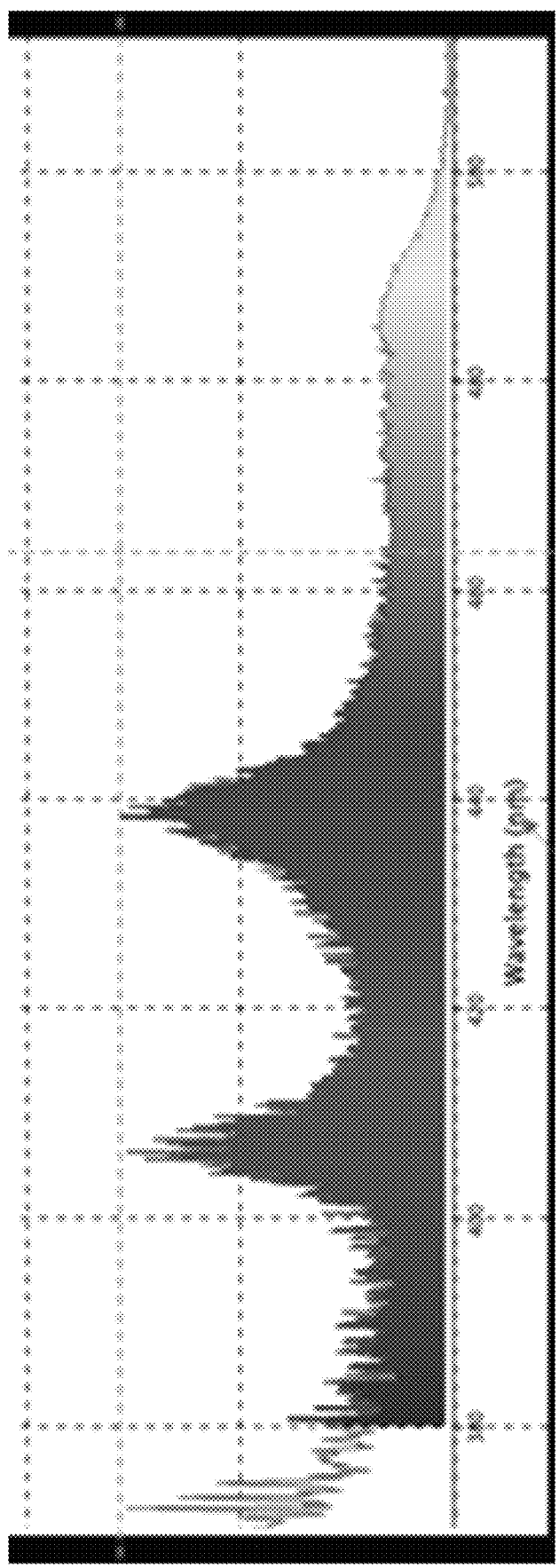
FIG. 3A is an exemplary graph of specific spectrum for 5 LEDs.

In some embodiments, a metal halyide bulb can be used. As shown in the exemplary graph in FIG. 3A, the waveform provides "peaks and valleys" such that specific spectrums are naturally higher than others as a function of the bulb/light that is illuminated from the bulb, but the intensity of the specific frequencies within the waveform cannot be changed. Looking at the power of the various frequency bands as a percentage of the total power delivered, it is shown that most of the frequencies outside the 400 nm-500 nm range are fairly low in power percentage-wise.

If a specific frequency/intensity is needed to affect the kill of the bacteria and that intensity is lower than needed, there is no means to increase the power without raising all the other frequency powers. This runs the risk of potentially inducing more power than is required and at the risk of potential damage to normal cell viability.

Figure 4A:
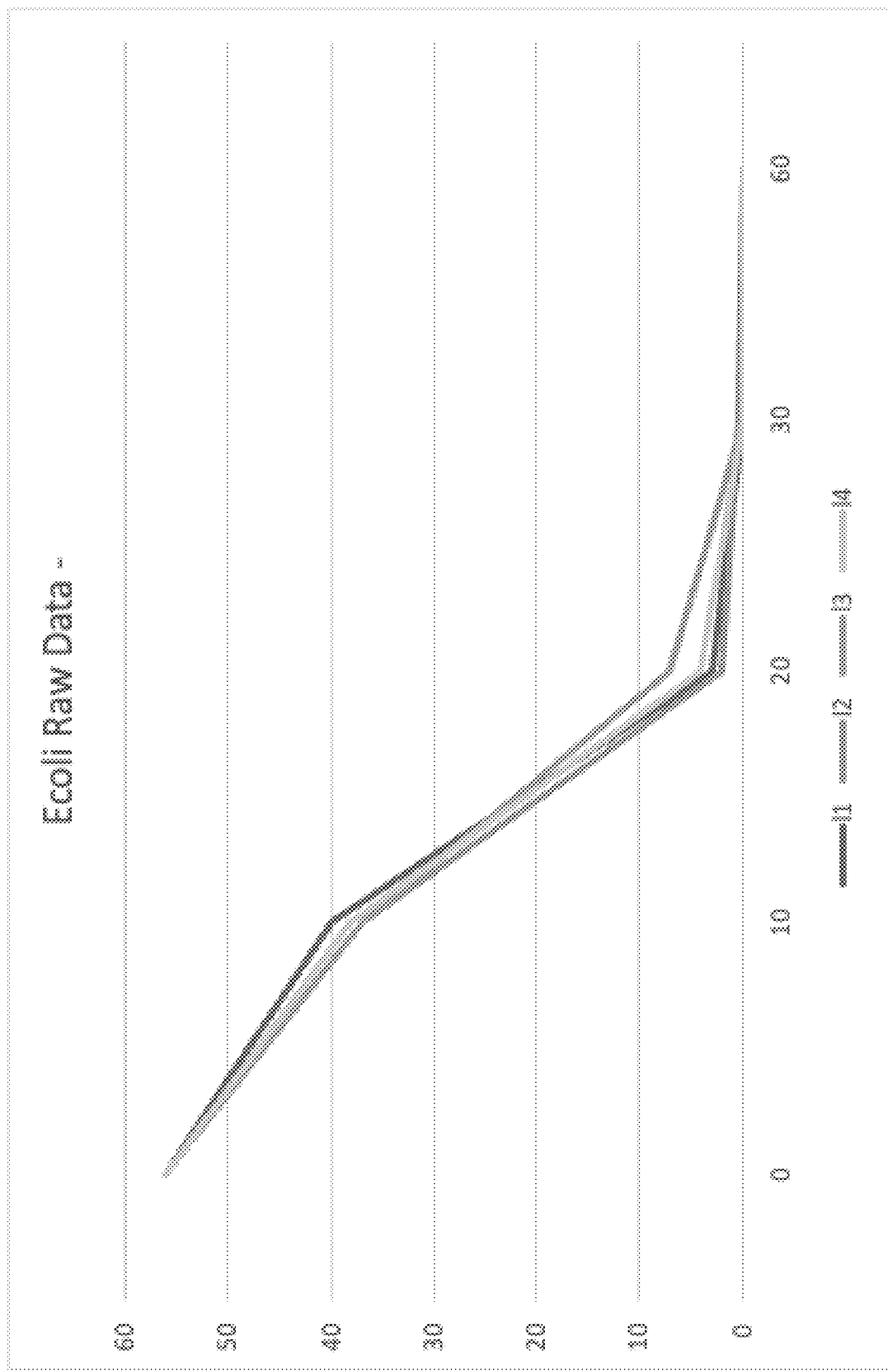
FIG. 4A, FIG. 4B, FIG. 4C, FIG. 4D and FIG. 4E are exemplary graphs illustrating bacteria reduction over time as it relates to power.
Figure 4B:
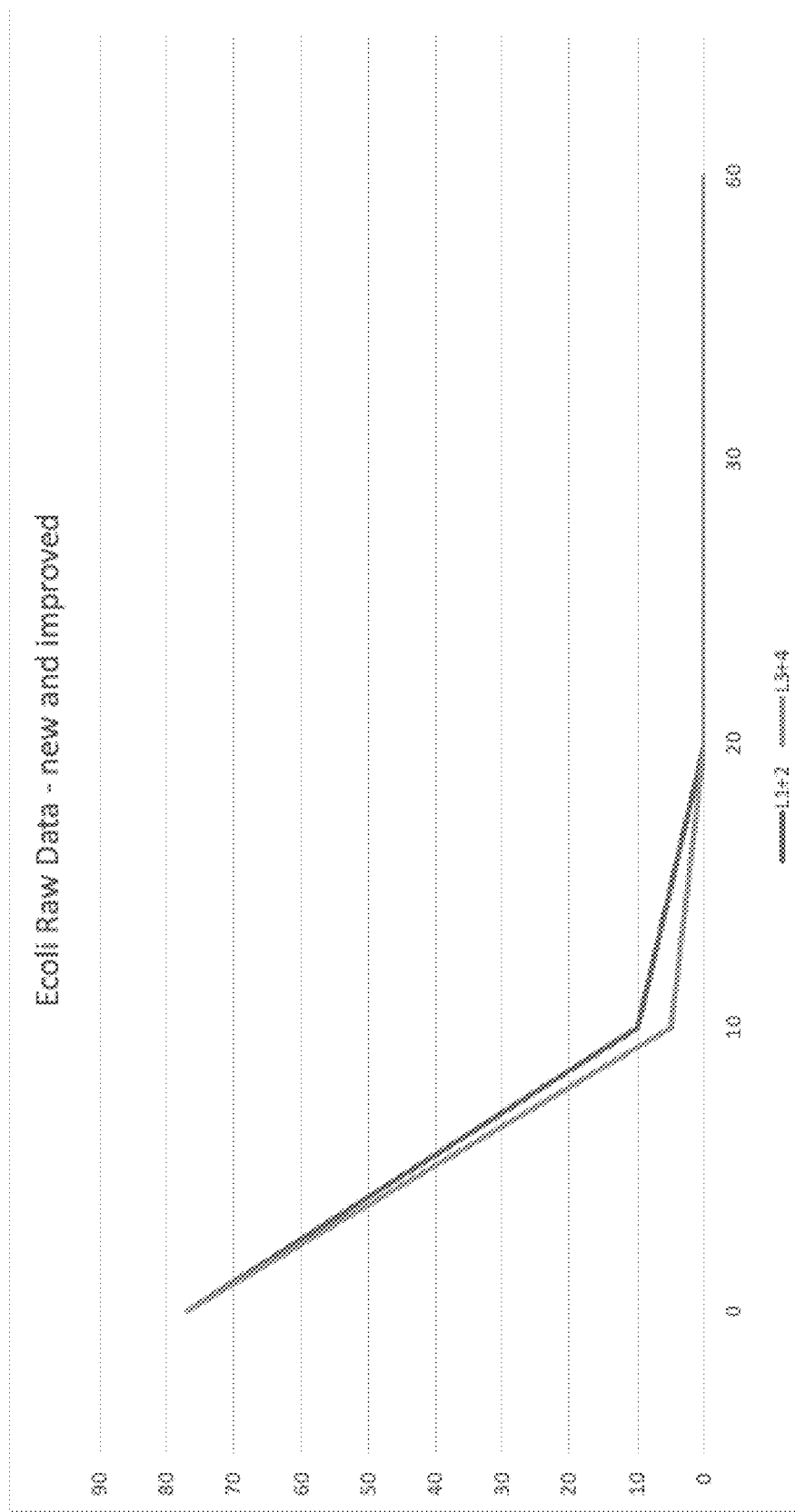
Figure 4C:
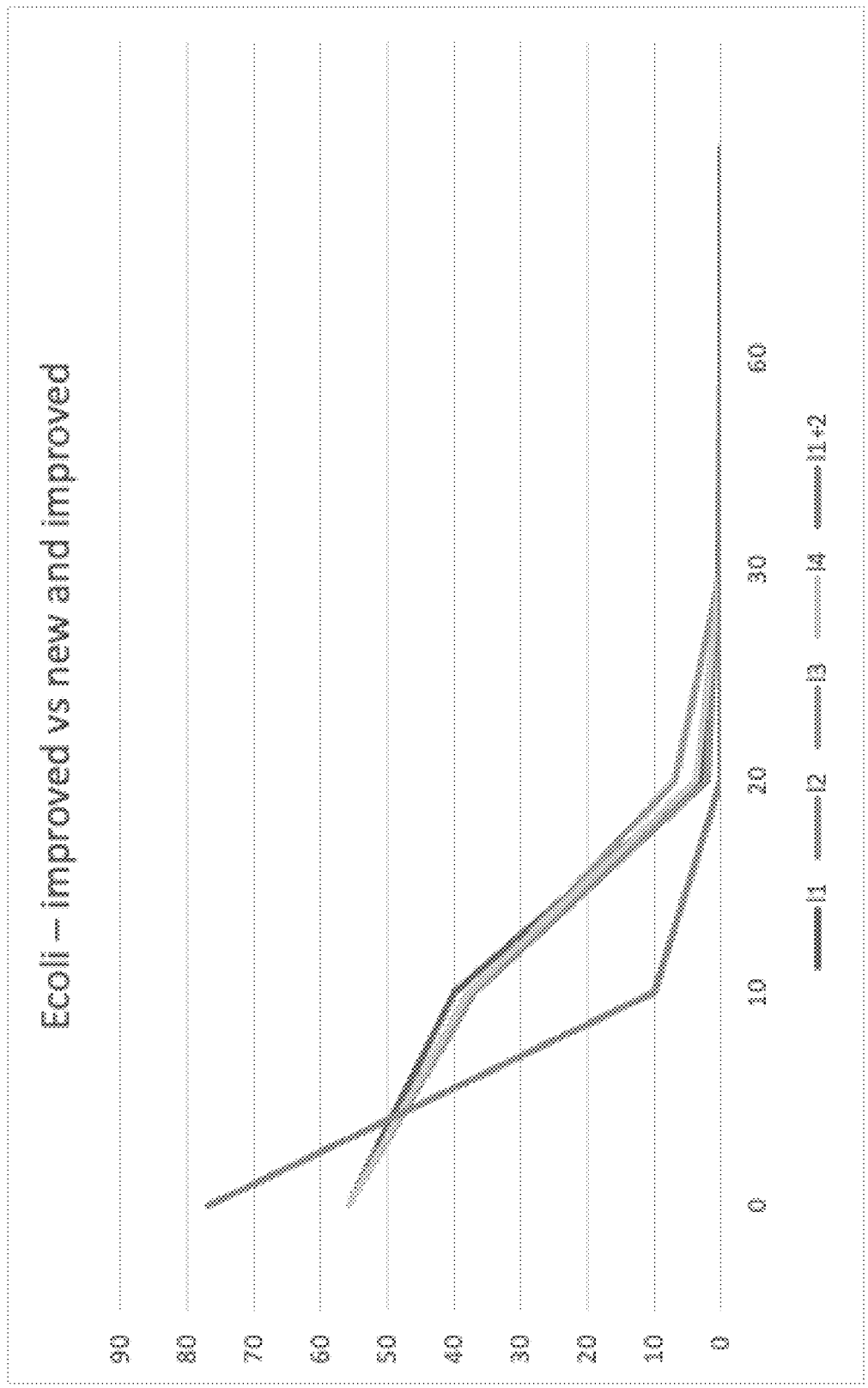
Figure 4D:
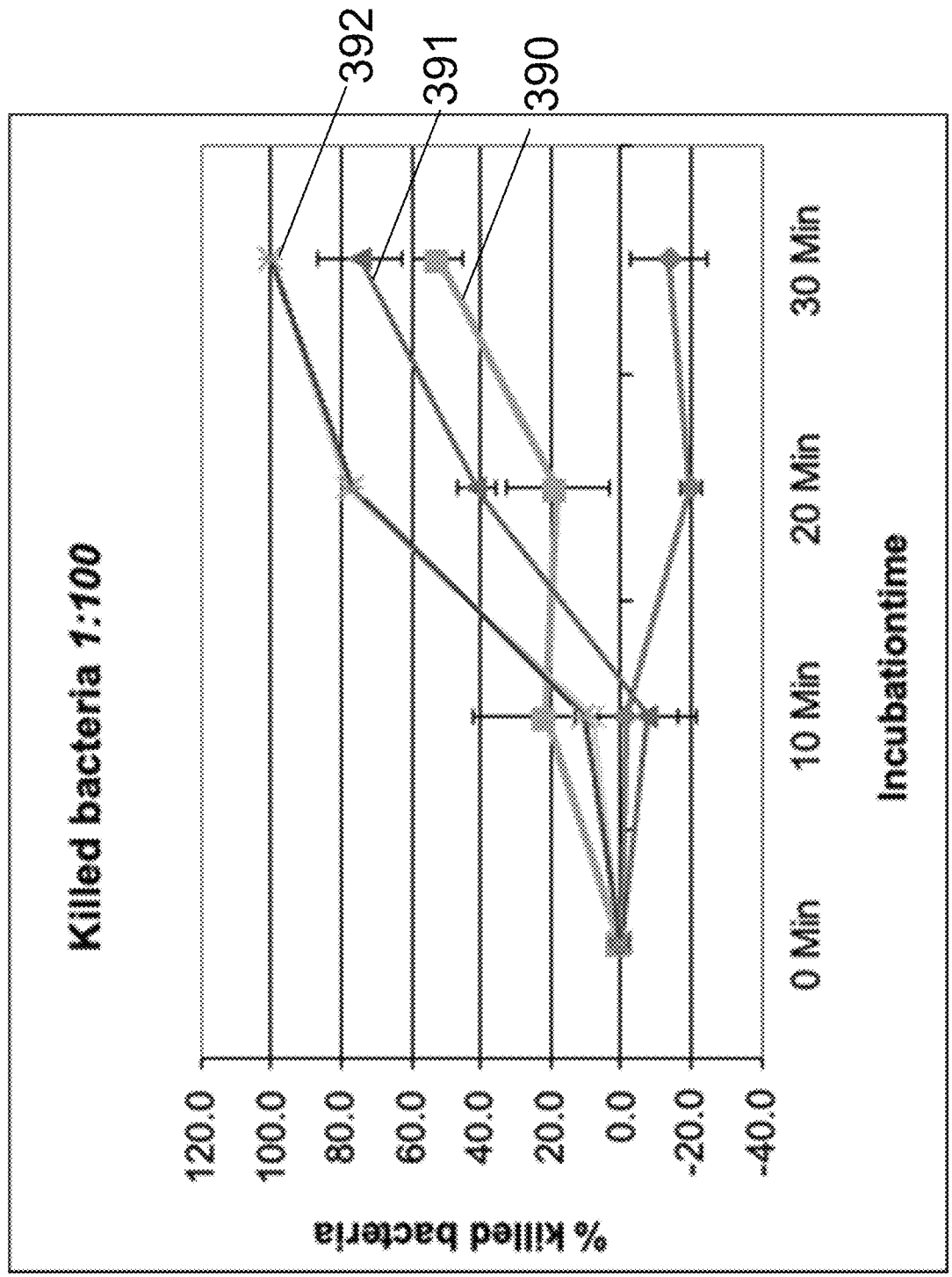
Figure 4E:
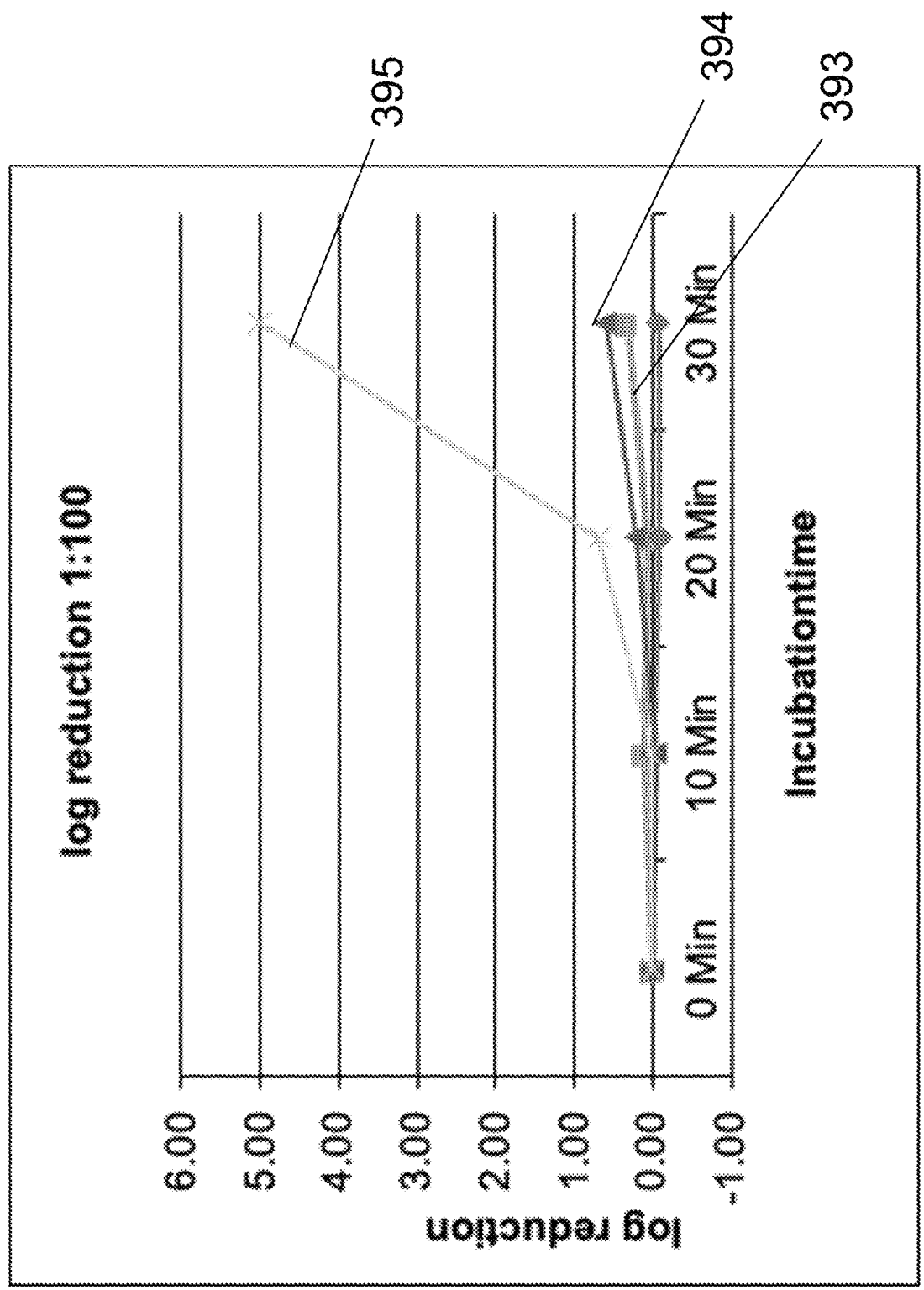

As shown in FIG. 4A, FIG. 4B, and FIG. 4C the frequency of the systems can remain the same while the power can increase, and the step up in power can result in faster and better kill of the target bacteria. Thus, more power results in more a more effective bacteria elimination. Similarly in FIG. 4D and FIG. 4E, which illustrates exemplary graphs showing time versus bacteria reduction at different power settings, high power correlates to an increase in bacteria reduction. Three different power level are shown in FIG. 4D, with lines 390, 391, 392 going from lowest to highest power. Similarly, three different power level are shown in FIG. 4E, with lines 393, 394, 395 going from lowest to highest power.

A plurality of specific LEDs at the specific frequencies can be used at frequencies that are desired or needed to cause an antimicrobial effect. This allows the frequency and the intensity delivered to the tissue is more defined and specific as the intensity of each LED is controlled—the delivered intensity at the various frequencies can be the same if desired—vs the peaks and valleys of the metal haylide.

If specific frequencies of light are appropriate in the remediation of one bacteria, while other frequencies are not, those frequencies can be turned off as there is no reason to deliver light to the treatment zone if it is not beneficial. Thus, it is possible to provide the desired frequencies of light using a subset of the plurality of LEDs as needed for each specific bacteria. This can provide a variable and tunable system.

The "tuning" of the system is relegated to the application or use of specific LEDs as each LED is a single frequency light. Thus, the system does not have the ability to adjust the LEDs other than adjusting the power intensity up or down. The system uses the combination of the available LEDs to create an appropriate blend of frequencies to achieve a blend of light frequencies to achieve the appropriate kill factor for a given bacteria. The system can adjust the power to increase or decrease the peaks (i.e., power intensity) of the various frequencies. In some embodiments, this can be done to ostensibly derive a square wave to create a block of power hitting the bacteria.

Figure 3B:
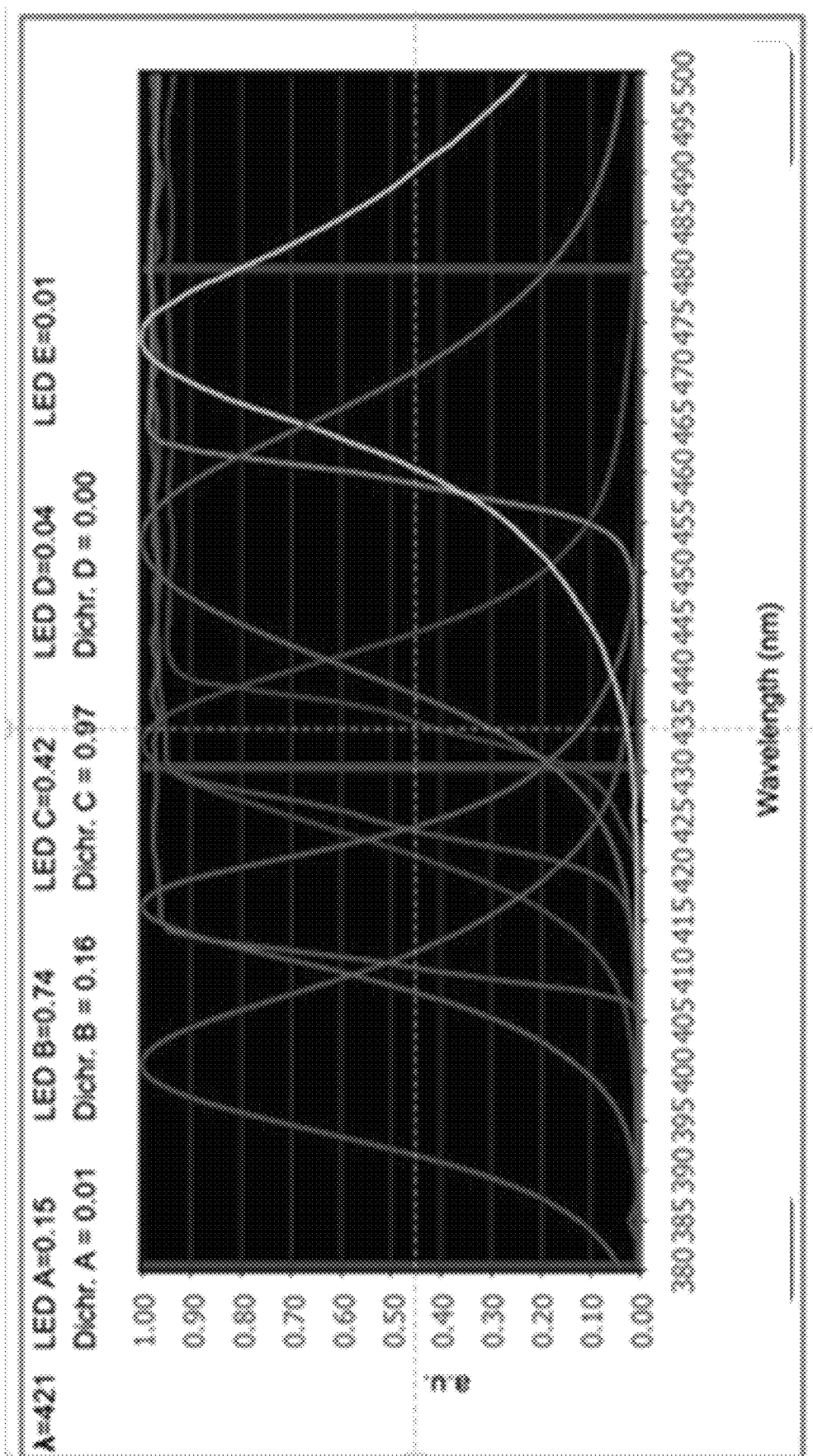
FIG. 3B is an exemplary graph showing peaks for 5 LEDSs at 405, 415, 435, 450 and 475 nm.
Figure 3C:
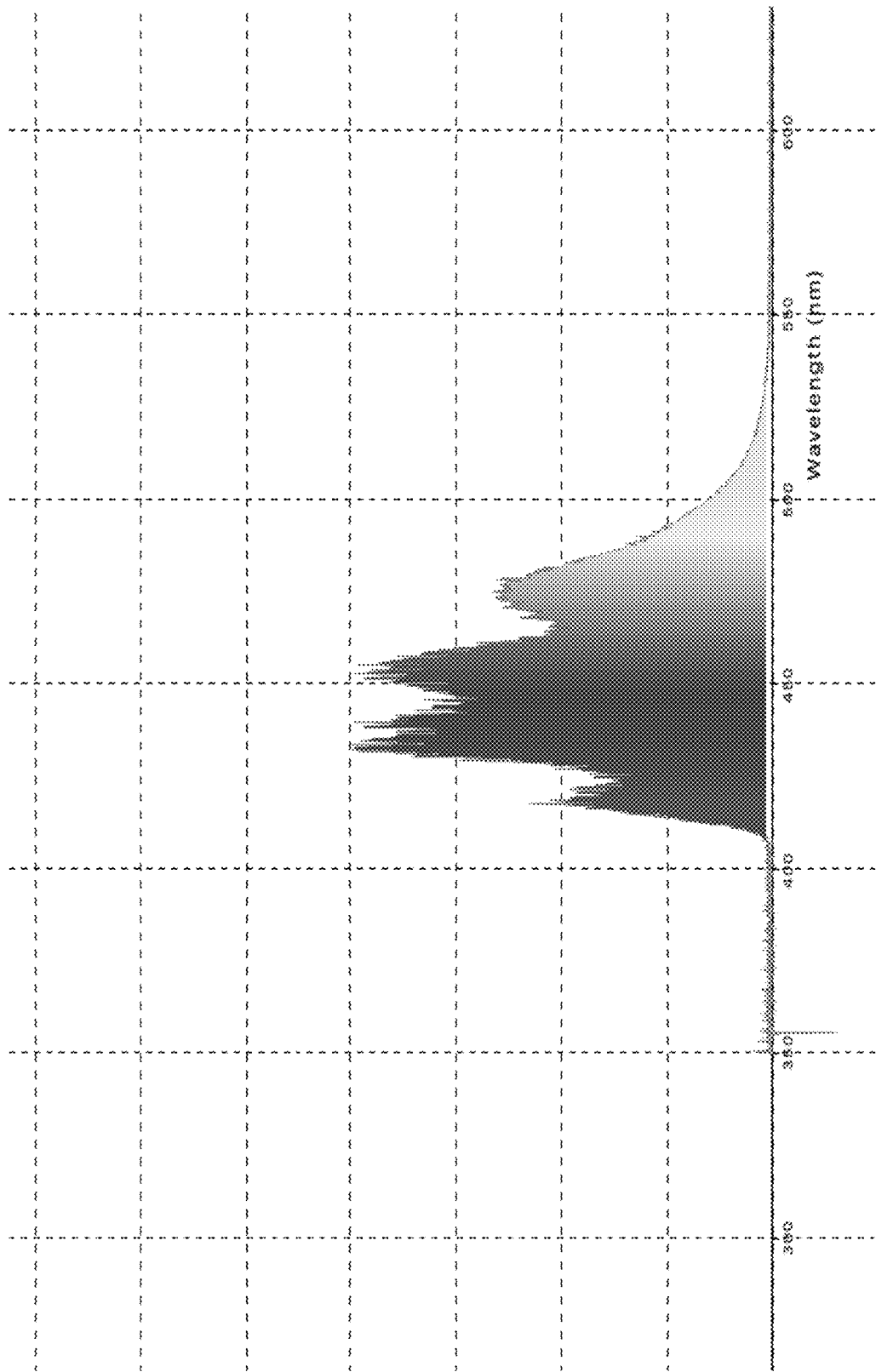
FIG. 3C is an exemplary power grid of the spectrum from system having five LEDs.
Figure 3D:
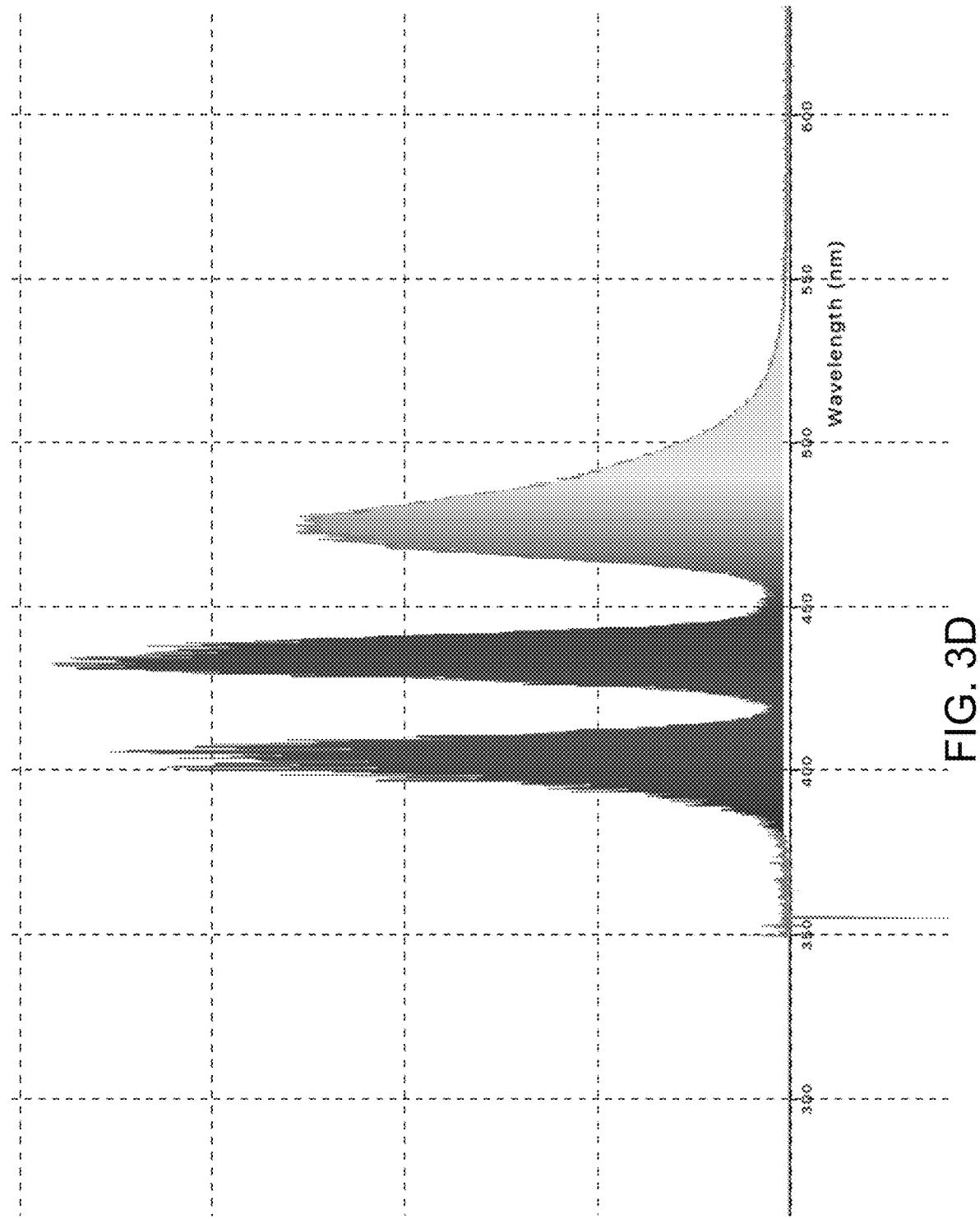
FIG. 3D is an exemplary graph of an adjustment of the power levels of three out of five LEDs such that the peak are approaching similar heights.
Figure 5:
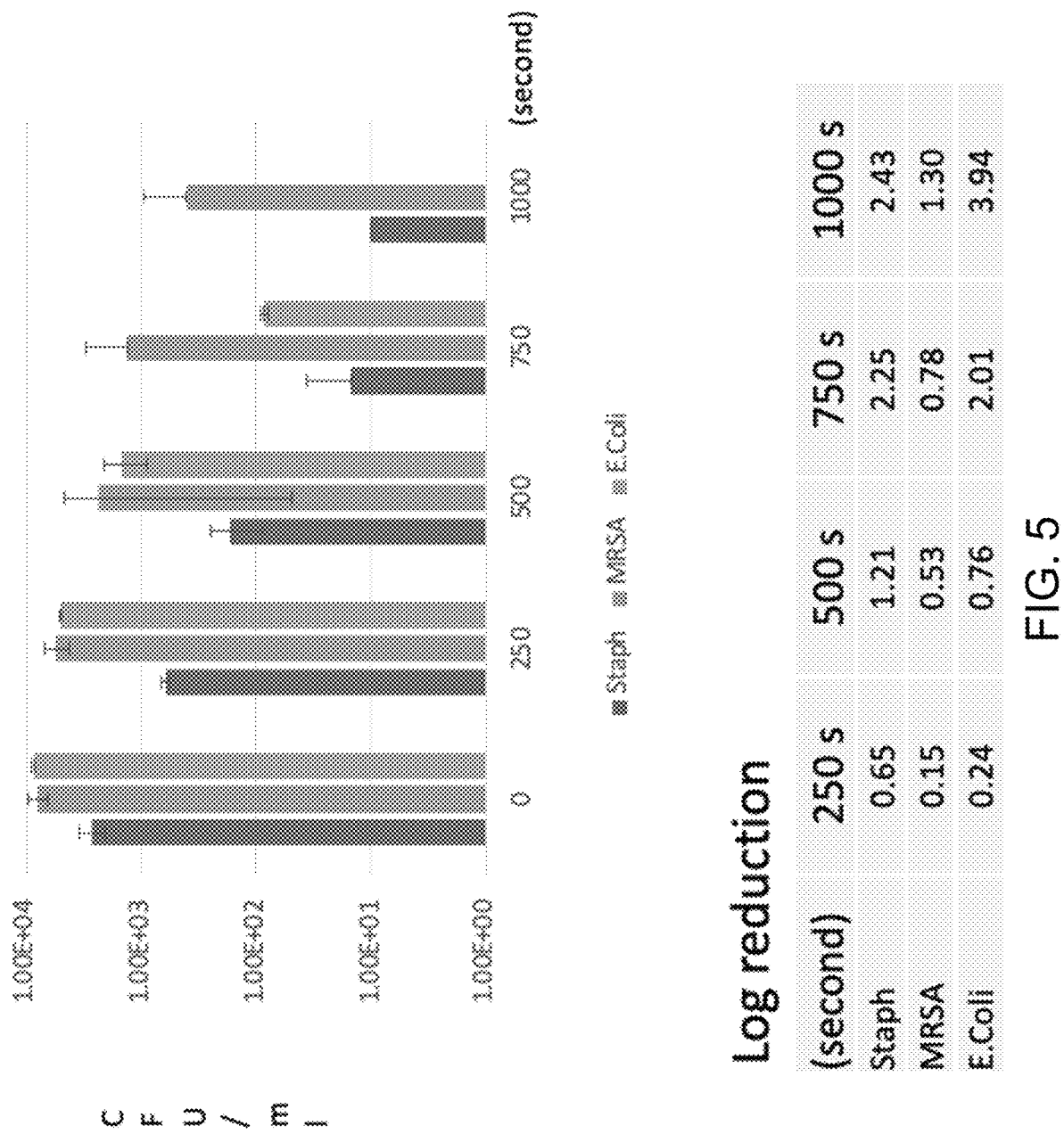
FIG. 5 illustrates exemplary results of the use of five LEDs to treat a tissue and/or bone.

For example, as shown in the exemplary graph in FIG. 3B, 5 LEDSs can be used at 405, 415, 435, 450 and 475 nm. A power grid of the spectrum from the 5 LEDs is shown in FIG. 3C. In some embodiments, individual power for each LED can be adjusted so each LED spectrum has its peak at the same level. FIG. 3D illustrates an adjustment of the power levels of three of the five LEDs such that the peak is approaching similar heights on the illustrated graph. As shown, the LEDs running at 415 and 450 are turned off. As shown, the three peaks have roughly the same peak each with the same power. This can be done such that each LED gives out the same power. If more power is needed, they can be adjusted individually or serially so that none of them become overpowered. It will be understood that any number of LEDs can be used and defined for any frequency. All the LEDs can be running at the same power or turned off if any of them are not needed. For example, if a specific bacteria is affected by a certain frequency, only that LED at that desired frequency can be run while the others are turned off. Thus, a fully variable and dynamic LED array can be used that can be customized depending on the desired treatment. In addition, any variation between 400 nm and 475 nm can be used.

In some embodiments, the system can be used and controlled either prior or during the procedure, and has the ability to vary/modulate/alter the intensity and/or the frequency of the light being delivered to treat tissue. The use of a "blue light" can cause cellular death, for example in the range of 400 nm-470 nm, absorbed by porphyrins, causing cell death by the generation of toxic reactive oxygen. The bactericidal effect of blue light has been shown in many pathogenic species with varying energy doses of J cm-2 sufficient to achieve remediation.

FIG. 5 illustrates an exemplary graph showing the use of five LEDs and their effect on various bacteria. For example, as shown, E coli had a ~4 log reduction with the 5 LED system, and ~0.6 log reduction with the broad spectrum.

It will be understood that both frequency and power are responsible for the killing of bacteria. In some embodiments, the frequency and/power of the plurality of LEDs can be tuned in an attempt to target specific bacteria. In some embodiments, a more broad spectrum approach can be used with the plurality of LEDs. For example, using high power at (seemingly) the wrong frequency can provided a null response. In addition, as many physicians do not know the specific strain of bacteria that is affecting a patient, the effects of using a broad spectrum light system can outweigh negatives of frequency specificity in an attempt to target a specific bacteria.

Figure 6A:
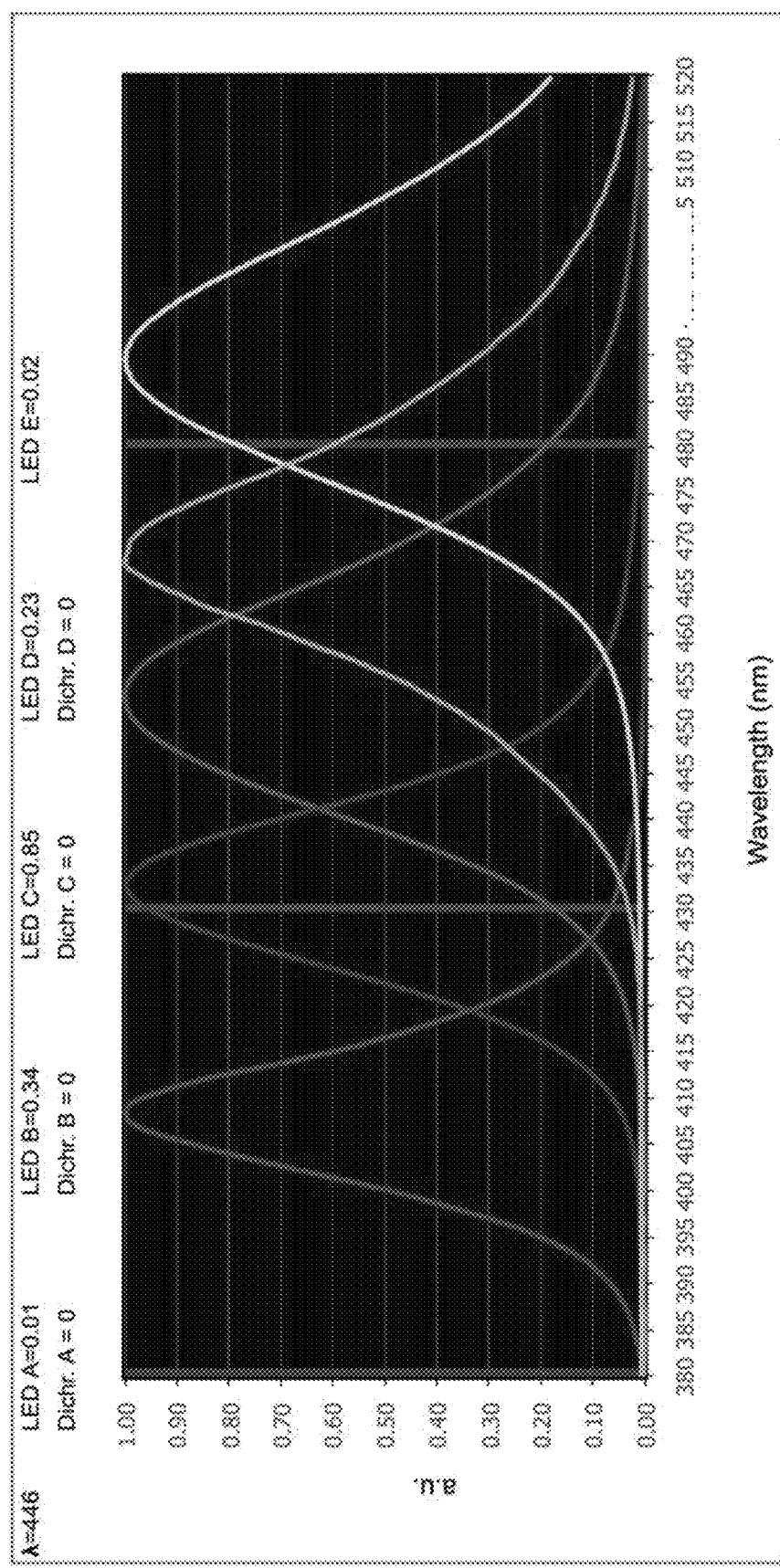
FIG. 6A and FIG. 6B show an embodiment of a system with multiple LEDs that are dialed in via a light box (i.e., switches thrown to pull specific frequencies), and the ability to drive the various LEDs at different powers (so that the optical output is the same)
Figure 6B:
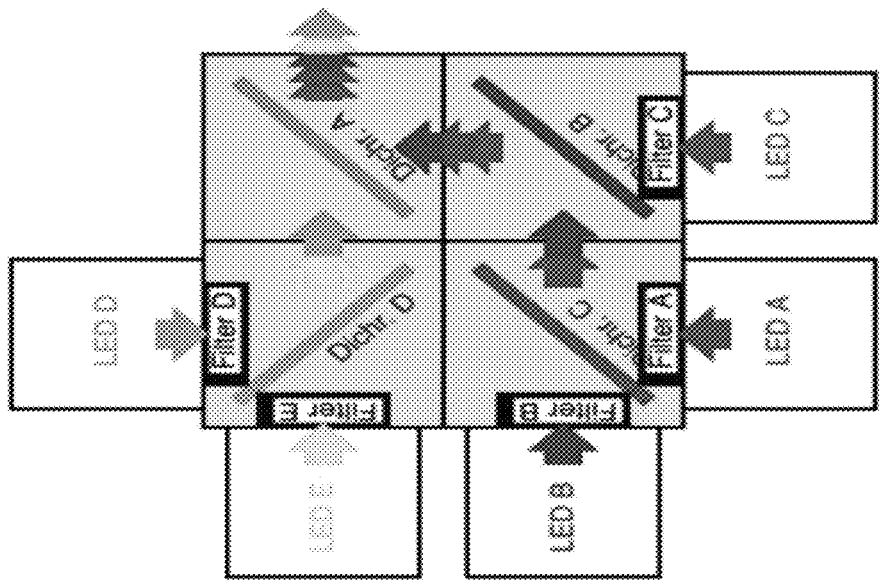

In some embodiments, a plurality of LEDs, as shown in the exemplary graphs in FIG. 6A and FIG. 6B, can be used and can be dialed in via a light box (i.e., switches thrown to pull specific frequencies), and the ability to drive the various LEDs at different powers (so that the optical output is the same). This allows for "ganging up" of multiple LEDs with different frequencies, and optical mirrors can be used to merge the multiple light frequencies into a single plastic optical fiber. Different LED frequencies can have different optical output, e.g., intensity. The output can be adjusted through the drive current, where overdriving them will result in higher optical output. The multiple LEDs ganged up can be used to fine tune the frequency/frequencies of light that are delivered to the fiber in the treatment of the bacteria, as certain species of bacteria have different frequencies of light that are able to kill them. This allows the system to target the light to the species of bacteria to make it a more targeted system.

The peaks shown in the exemplary graphs in FIG. 7A, FIG. 7B, FIG. 7C, and FIG. 7D are from different LEDs. In some embodiments, more than one LED (or any light source, such as lasers) can be used to provide light to the same light fiber. For example, 1 LED, 2 LEDs, 3 LEDS, 4 LEDs, 5 LEDs, 6 LEDs, 7 LEDs, 8 LEDs, 9 LEDs, 10 LEDs, 12 LEDs, or 15 LEDs or more than 15 LEDs can be used depending on the desired spectrum of light delivered. It is possibly to use two or more LEDs to provide more power. Intensity of power delivered across delivered light spectrum can be made uniform or substantially uniform by adjusting the current (power) of each LED. Additional LEDs can be added to fill in gaps so a user can create and control the light spectral curve delivered by a plurality of LEDs. For example, there can be uniform power across the spectrum, power can be varied across the spectrum, and the addition of additional LEDs adjusts the spectral curve.

Figure 7A:
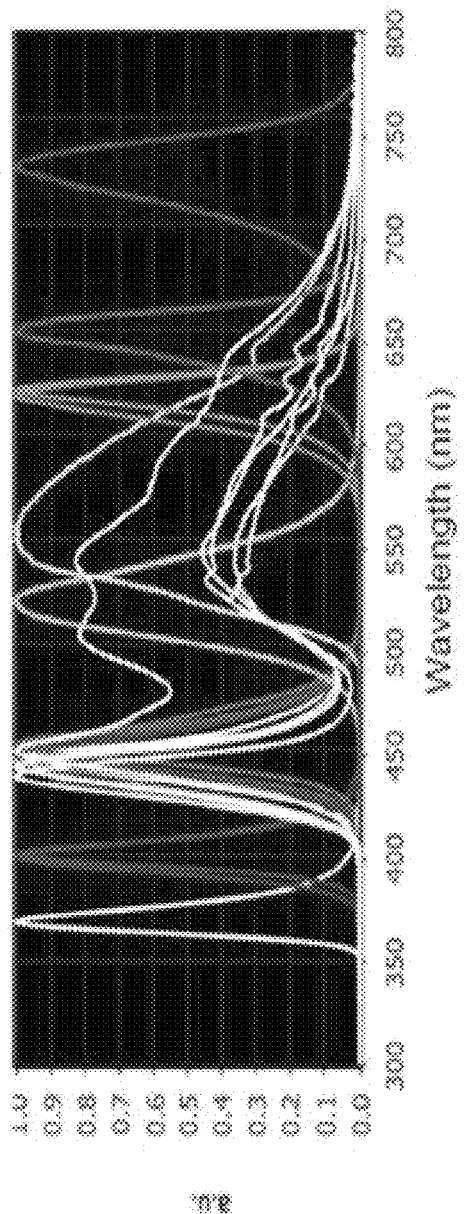
FIG. 7A, FIG. 7B, FIG. 7C, and FIG. 7D show exemplary graphs of spectral curves of the presently disclosed device with various numbers of LEDs.
Figure 7B:
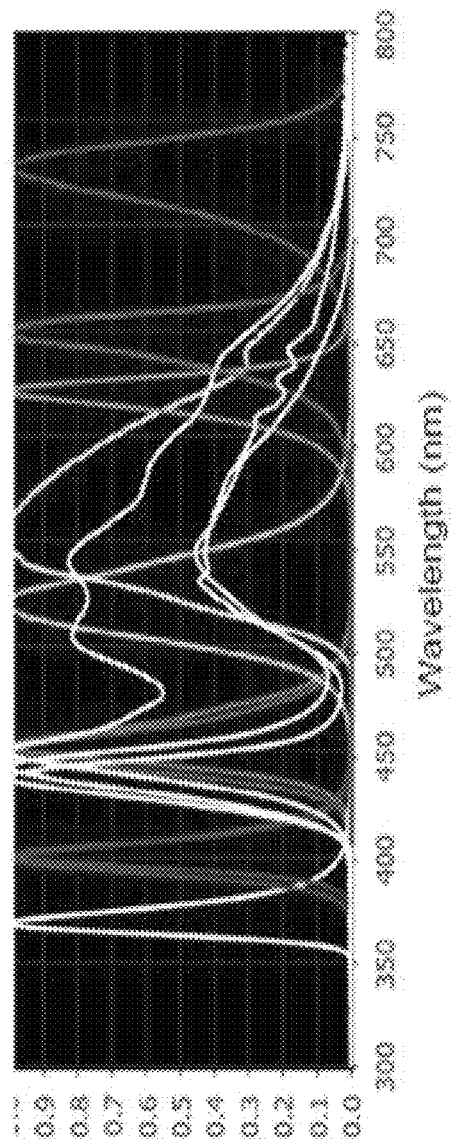
Figure 7C:
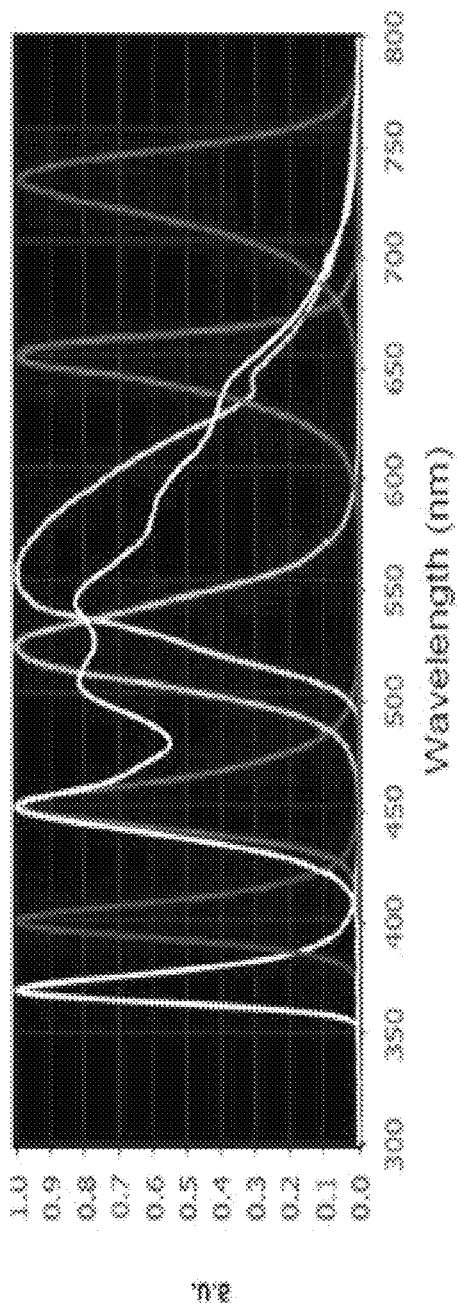
Figure 7D:
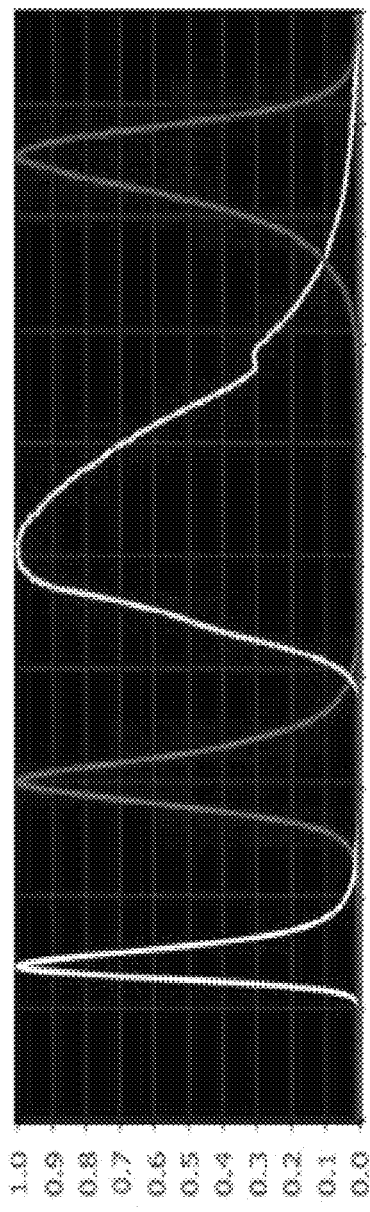

FIG. 7A, FIG. 7B, FIG. 7C, and FIG. 7D illustrate various exemplary graphs showing the spectral curves of the presently disclosed device and methods having varying plurality of LEDS. FIG. 7A illustrates the exemplary spectral curves of the presently disclosed device having 15 LEDs or more LEDs. FIG. 7B illustrates the exemplary spectral curves of the presently disclosed device having 12 LEDs or more LEDs. FIG. 7C illustrates the exemplary spectral curves of the presently disclosed device having 8 LEDs. FIG. 7D illustrates the exemplary spectral curves of the presently disclosed device having 4 LEDs.

Figure 9:
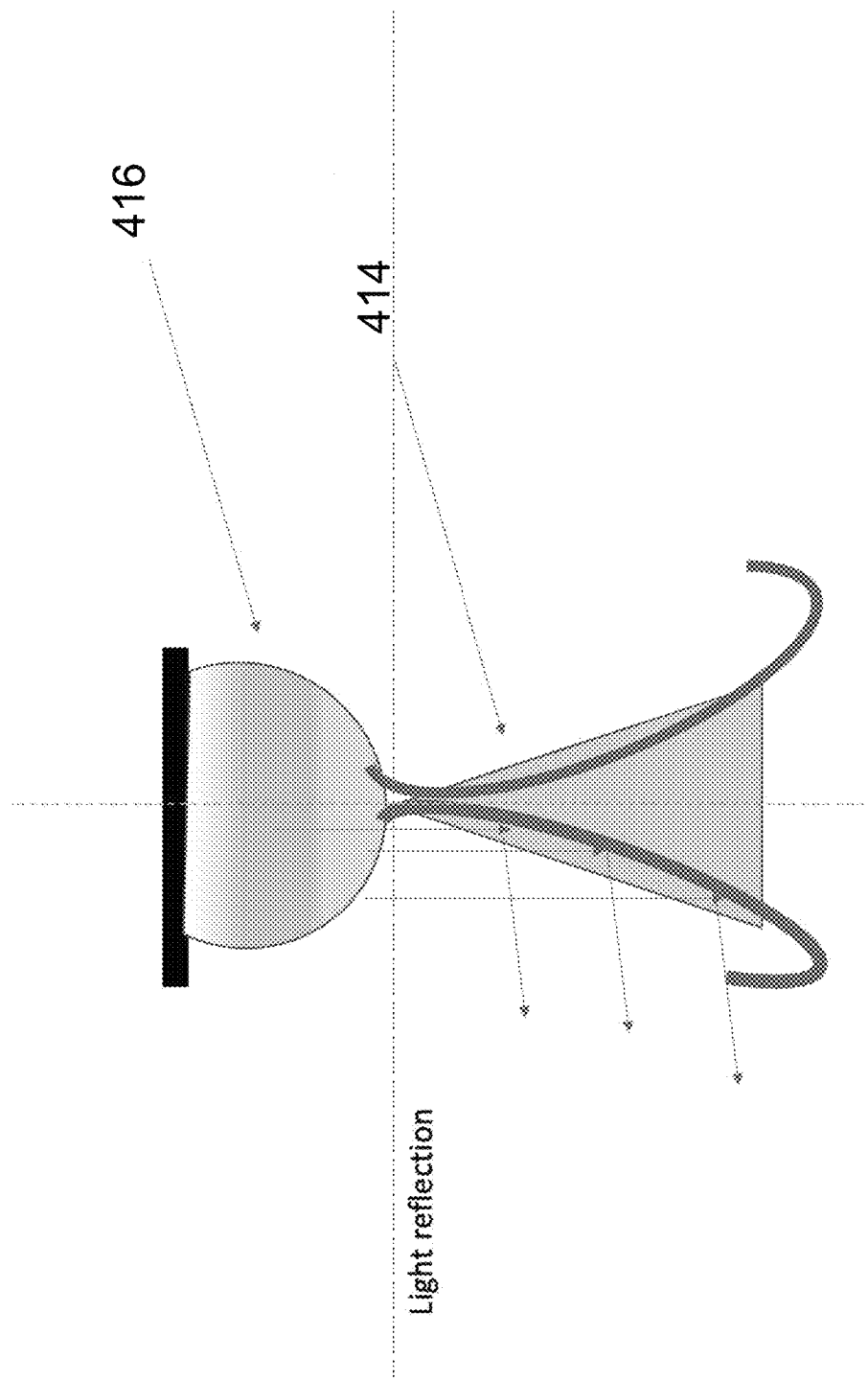
Figure 10:
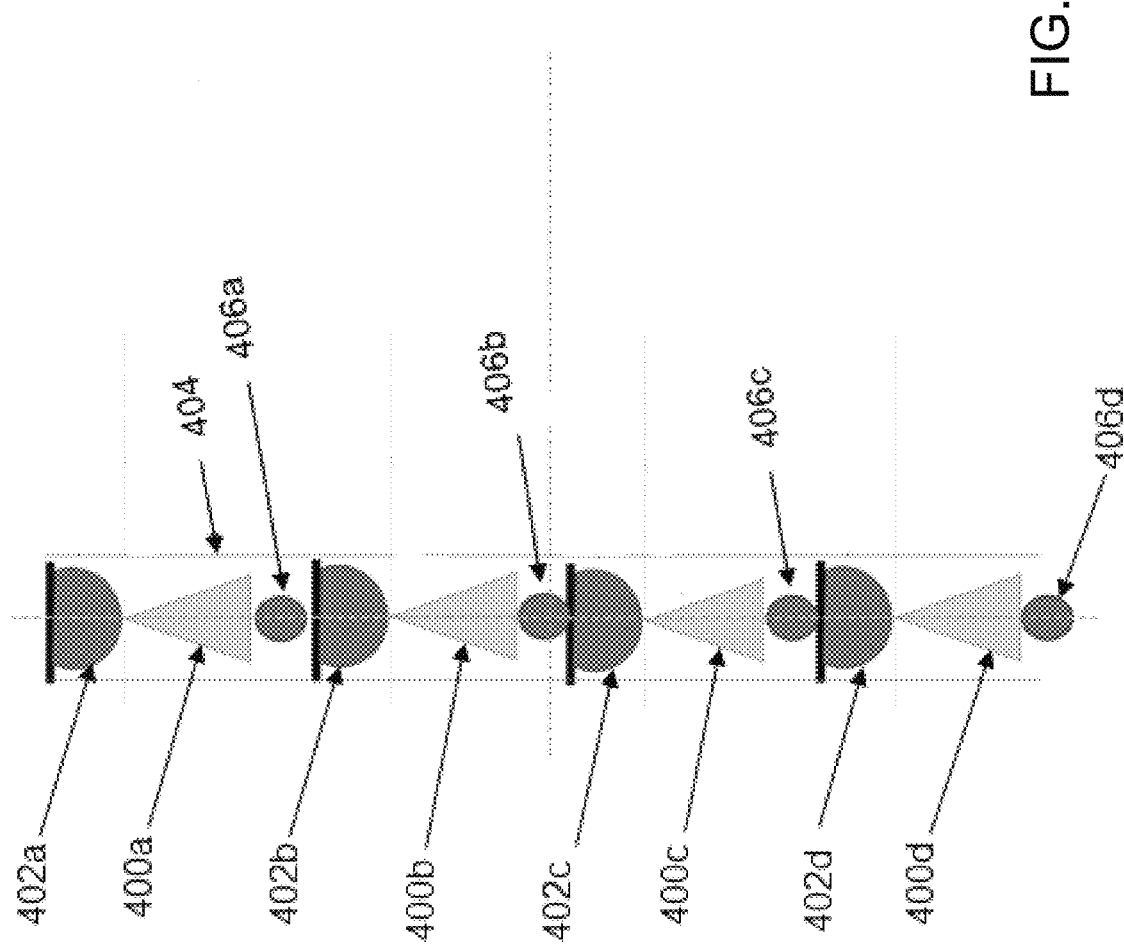

In some embodiments shown in FIG. 8, FIG. 9, and FIG. 10, one or more conical reflecting members (e.g., cone mirror) with an LED mounted on the tip of the reflective cone can be used such that the incidence of reflection causes a circular dispersion of even light around the cone. A cone mirror 410, as shown in FIG. 8, can be used in combination with an LED 412. The angle of the taper of the cone mirror can be used to direct the reflective beams of light outward, as shown with the cone mirror 414 and LED 416 of FIG. 9. This combination of LED and reflecting member can create a radiant ring of light due to the shape of the reflecting member.

In some embodiments, a plurality of LEDs 418 can be connected together on a string or fiber 420, as shown in FIG. 11, to form a chain of LEDs. The string of LEDs can produce even light deposition over the length of the string. Any length of string can be used and any number of LEDs can be position therealong depending on the size and shape and location of the treatment site.

In some embodiments shown in FIG. 10, a plurality of sets of conical reflecting members 400a, 400b, 400c, 400d and LEDs 402a, 402b, 402c, 402d are positioned in or encased within a clear tube 404 to preclude the transmission of light by intramedullary fluids in contact with the reflection or emitter faces. Support spacers 406a, 406b, 406c, 406d can be positioned between each conical reflecting member and LED to allow for rotation and malleability of the assembly. The stacked LEDs and cone mirrors within the tube act as a light fiber of LEDs.

In some embodiments, a malleable rod can be used comprised of multiple LED's mounted to the ends of small sections of high efficiency glass coupling (LED-glass-LED-glass) where the glass sections are internally modified to cause the light from the LED to be deflected outwards. The emitter face of the LED's can be mounted on top of a reflective mirrored shape to eminate the light outwards. These are encased within a clear tube to preclude the transmission of light by intramedullary fluids in contact with the reflection or emitter faces.

As shown, cone mirrors can be mounted on a surface that allows them to bend/rotate. An apex of the cone mirror can meet or be afixed in a position relative to the LED emitter such that it takes the light from the emitter and disperses it radially outwards. These assemblies can be stacked, multiple ones on top of each other, to form a line or a cylinder of emitters and cone mirrors. The entire assembly can be placed within a thin clear transparent tube which prevents bodily fluids from coming in contact with the emitter and/or the cone mirrors, which would preclude light transmission. The mirrors are used to bounce the light outward as the LED directs the light down the fiber. The geometry of the mirrors (flat planes) help in achieving this circumfrential outward redirection of the light. The cone mirrors are affective in short lengths, allowing for a system that can be flexible as the cone mirrors can be bent in reasonably short segments.

Figure 12A:
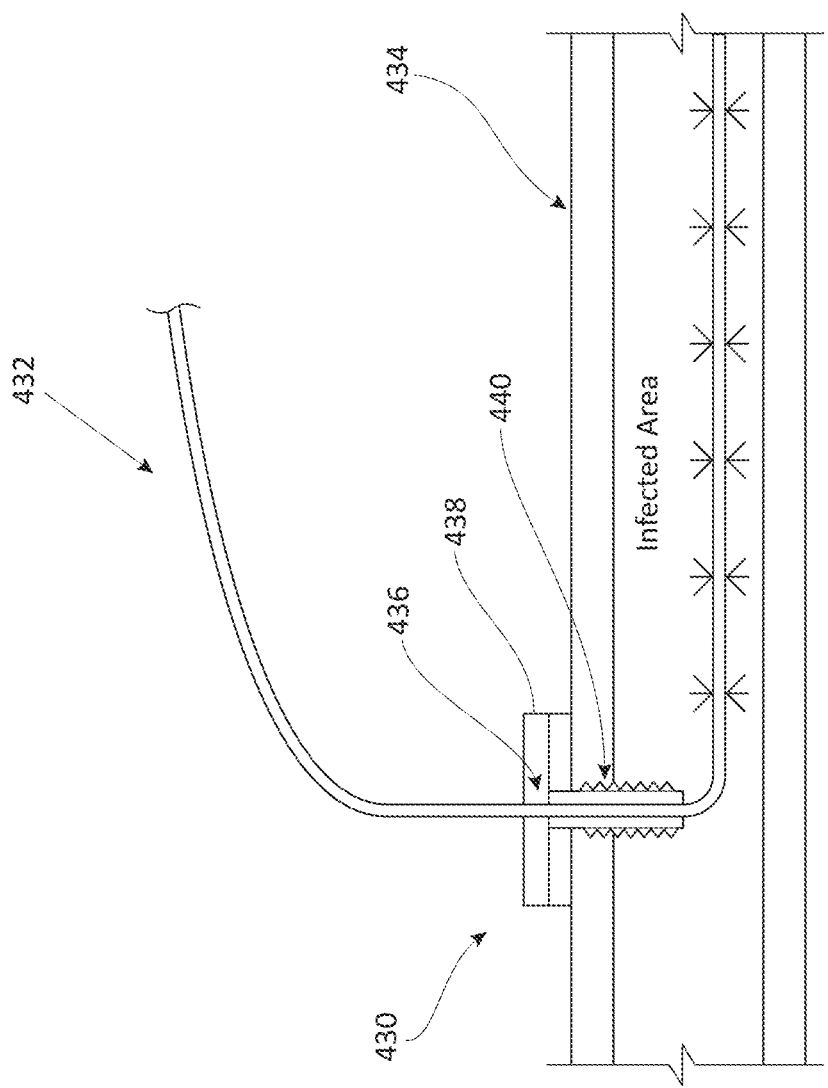
FIG. 12A shows an exemplary embodiment of a device providing an anti-microbial effect on a bone positioned in a body.
Figure 12B:
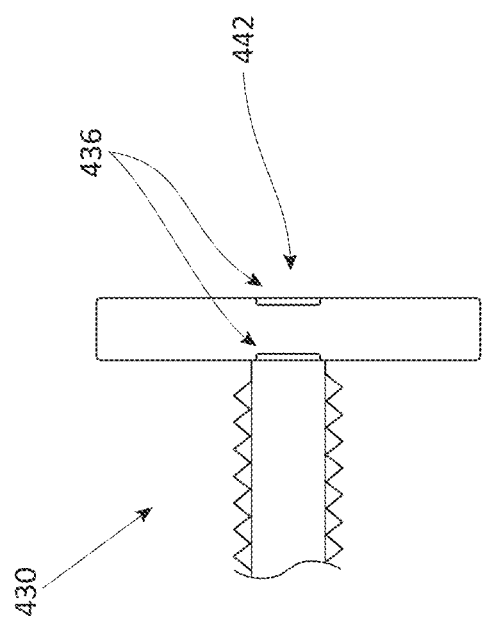
FIG. 12B is an exemplary embodiment of an introduction port for introducing one or more fibers for providing an anti-microbial effect on a bone.

Various treatment protocols can be used when treating a bone infection. In some embodiments, the ABLP for single stage delivery can be used for treatment of infection (e.g., one dose of light-on/off) for some defined period of time, after which the catheter can be removed from the canal. In some embodiments, the ABLP dual stage can be used for longer term treatment, with the catheter residing within the canal for a long period of time, for example a period of days. This can provide multiple doses of light to the canal, which allows for longer term indwelling of the catheter. The ability to place a port 430 through a bone surface 434, with access to the intramedullary canal, to open the port and deliver the light fiber 432, remove the fiber and close the port, and then open the port in a different time period and deliver a new fiber for additional treatments, as shown in FIGS. 12A and 12B. The port 430 can include a septum 436, an antimicrobial disk (or bandage) 438, a flexible tube 440 through the bone surface, and an opening 442 through one or more fibers can enter the bone. FIG. 12B illustrates an embodiment of the port 430 for delivering the fiber and can provide a way to maintain the position of the fiber. In some embodiments, the ABLP can be used as a single fiber, where only a single fiber is delivered within the canal providing light to the infected area. In some embodiments, the use of the ABLP as multiple fibers delivered within the canal such that all of the fibers providing light to the infected area is used. In some embodiments, multiple fibers can be used, each providing individual frequencies of light. In some embodiments, multiple fibers can be used, each providing multiple spectrums of light. In some embodiments, the delivery of the multiple fibers within the canal can be either as a single treatment, or the multiple treatments, as mentioned above.

Still referring to FIG. 1A, the beam of blue light/beam can deliver variable energy densities to bone walls of the cavity of the bone. However, unlike systems that have an illuminator directly or integrally part of the light source, there is no heat generation through the delivery of light using the catheter, for example to bone walls of the cavity of the bone, while emitting the blue light/beam. The steps of emitting the blue light/beam within the cavity of the bone may be completed without: (1) exposing the bone walls to further evasive surgical procedures due to antimicrobial effect related treatments; (2) the need for applying antimicrobial type liquids or related applications; and (3) the need of removing the killed micro bacteria from the affected area. Micro-bacteria may be defined, by non-limiting example, as an opportunistic microorganism. For example, a bacterium, virus, fungus or the like, that takes advantage of certain opportunities to cause disease, i.e. those opportunities can be called opportunistic conditions. These microorganisms are often ones that the human immune system cannot raise an adequate response, such these microorganisms can eventually overwhelm the body's weakened defenses.

For example, according to at least one aspect of the disclosure, it is contemplated to kill micro bacteria that may have an opportunity to exist or already exists within the cavity of the bone. The use of the blue light/beam can include many variables when treating an affected area, by non-limiting example, the blue light/beam may incorporate many combination of aspects when being applied to an affected area such as: (1) variable energy densities, conceptually by altering the wave form on the light liber it is possible to emit more or less light in different and specific areas—and similarly alter the temperature on a local level or site specific area; (2) variable generated temperature(s) at a specific location within the affected area; (3) variable exposure time emitted to the affected area; (4) variable distance of the optical fiber's distal end to the affected area; and (5) a pulsing or constant blue light/beam emitted or a combination thereof, among other things.

Still referring to FIG. 1A, the instant disclosure may additionally include step or steps of incorporating variable temperatures such as cooling an affected area (before, during or after treatment), so that the bone wall temperature along the blue light/beam emission does not exceed a temperature that may result in irreversible damage to the bone walls of the cavity of the bone. It is contemplated that possibly cooling vents may be used in the process so as to pulse a cooling liquid, i.e. water, through channels to cool the implant and the surround tissue. It is also possible that to fill the balloon with a super cooled material so as to necrose or freeze the biofilm, i.e. bacterial colony, through an overall thermal effect and in conjunction with the blue light. By non-limiting example, the bone wall temperature along the blue light/beam emission may be contemplated not to exceed a temperature of about 42° C. or between 40° C. to 45° C. It is contemplated that a super cooled device may be used so that the application necroses tissue.

Further, the energy emitted by the blue light/beam may be termed in portions of joules (i.e. radiant energy), joules per cubic meter (i.e. radiant energy density), watts (i.e. radiant flux), watt per meter and watt per hertz (i.e. spectral flux), watt per steradian (i.e. radiant intensity), or the like. In some embodiments, the light that is delivered from the system from the tips of the fibers is measured in milliwatts or watts of energy. When the system is run, the seconds that the system is emitting light is multiplied by the milliwatts/watts to find the Joules (power).

The radiant energy (light dispersion of the light fiber) is evenly dispersed over the length of the active fiber, both longitudinally and circumferentially. Therefore the power is dispersed over a greater area, albeit at lower individual measurements associated with the greater coverage area. This even dispersion of power allows larger areas to be covered without fear of potential over illumination/overpowering the tissues. While greater power is needed to achieve the resultant energy being transmitted evenly along the length of the fiber, the process is far more controllable, owing to the greater area, versus that of a single point emitter.

It is noted that when using light to kill bacteria, it can be dependent upon a variety of factors, not the least of which, may be intensity as defined by joules (watts) or intensity multiplied by time. Further, the polymerization and antimicrobial effects are not the same, i.e., at the same time, or dependent such that, where polymerization can be the marriage of a known frequency light to a known monomer, i.e., photo initiator, with a specified time toward polymerization, the successful ability to kill bacteria may require a higher energy deposition than would be required to cure. It may be possible to circumvent a need to apply non-clinically relevant times, more light, i.e. energy that may need to be applied. Among other things, a possible solution may be to attempt to use higher energy and illumination sources. The use of higher energy sources, or potentially more focused and specific wavelengths, may obviate the limitations in the transference and limitations to the amount of energy may be transported down the fiber. The issue related to transference appears when light is transferred using a large/long active length of the fiber as there are inherent and physically unavoidable losses in transmission. At each point of emission there is a loss-of light that increases incrementally along the length of the fiber. Each further point starts with less light than the point before and decreases light at the next point such that at some point forward, there will be no emission as all the light has been consumed prior to the end of the fiber, creating a downward slope of light emission.

The optical fiber 106 used in the system 100 can be made from any material, such as glass, silicon, silica glass, quartz, sapphire, plastic, combinations of materials, or any other material, and may have any diameter. Further, the optical fiber 106 can be made from a polymethyl methacrylate core with a transparent polymer cladding. It should be noted that the term "optical fiber" is not intended to be limited to a single optical fiber but may also refer to multiple optical fibers as well as other means for communicating light from the light source to the expandable member. It is possible the fibers, after exciting the light source, may be twisted so as to form into a single fiber. Further, the optical fiber may comprise of a single fiber at a location that is in combination with multiple fibers at another location. It is possible, the multiple fibers positioned at the other location may be further incorporated into another single fiber at yet at another location within the system, i.e., the method of using the light fiber may be a single fiber or multiple fibers or any variation thereof.

If a prescribed dose (for example, intensity or some other measurement associated with the light) is defined as the means to achieve an antimicrobial effect, then that dose/amount of energy needs to be delivered over the entire length of the fiber for the affected area to be treated (except in the case of an infection being confirmed to a single location where illumination can be directed similar to the effect of a flashlight or spotlight).

For example, bones are hollow and often in the form of long linear tubes such that an infection can run the length of the bone. Equal energy can be applied to the affected length. Without an even energy delivery, one area of the bone could be getting a great intensity than other areas, so the bone is not being medicated evenly.

In some embodiments, it is possible to define a specific energy that is required to remediate a specific bacteria. This can include the energy emitted by the fiber, and a time of the exposure. This can be used to define the joules required to kill a bacteria. As the treatment of bone often involves the treatment of elongate tubular areas, the delivery of the fiber down the length of the bone requires that the illumination is not only even over the length of the fibers, but also even in a circumferential manner. Thus, in some embodiments, the light is not only delivered evenly in a single angle off of the fiber, but is also delivered evenly or equally in a circumferential manner.

This method of delivering light along the length of bone or other infected area overcomes the issue of decreased energy deposition over length of a fiber.

In some embodiments, this can be achieved by the manner in which cladding is removed from the fiber. Cladding is a bonded material on the surface or outer diameter of the fiber to maintain internal reflectance and transmission of the light down the length of the fiber without losses (attenuation) by light escaping from the fiber. For example, when a small opening, such as a nick, is made in a proximal end of the cladding, the light blasts out of that opening and steals light from the area below the nick. Each subsequent "nick" bleeds out light but the intensity of the second nick is less than the first as the pressure has already been lowered. This continues until the energy is almost negligible at the distal end, as shown in FIG. 3D.

Failure to have a system that maintains even light energy or dispersion of the system over the length of the fiber can cause a differential in energy delivery. The inbalance then precludes a method to achieve a delivery system where the specified power delivery is even over the length of the device. For example, either one end of side of the device is overpowered or underpowered. Thus, changing the power would lead to an unbalanced system.

Figure 13:
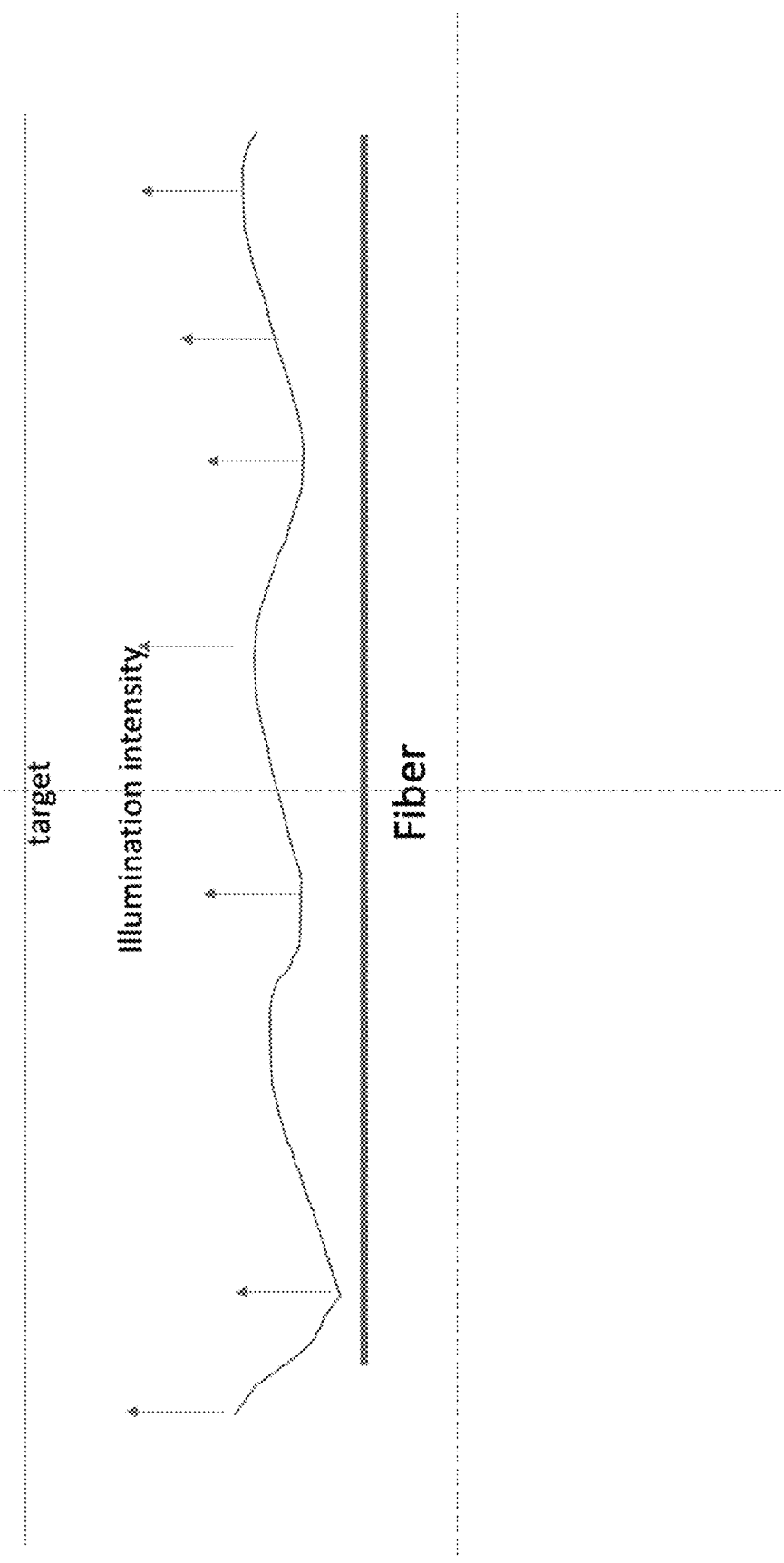
FIG. 13 illustrates an exemplary graph showing power distribution over the length of the fiber.

The light delivered by the fiber needs to be even over the length of the fiber such that the correct power over the length of the fiber can be provided, at even powers at short lengths over the fiber to achieve the antimicrobial effect, as shown in FIG. 13. If there is an imbalance in the power over the length of the fiber, there can be high spots and/or low spots, and the patient suffers as there isn't any way to achieve a balance in treatment. If there are high spots and/or low spots (areas of increased intensity and/or areas of decreased intensity), then there is not even power deposition to the targeted area needing treatment. This would correlate to overmedication or undermedication of the treatment site. Thus, the correct power can be selected for an even power distribution over the length of the fiber.

In some embodiments, uniform light delivery along the length of a fiber can be achieved by virtue of a variable helical spiral. Removal of cladding in this manner allows the system to maintain the same energy deposition over the length of the fiber such that the top and the bottom are even and light emanating from all planes of the fiber are uniform. This allows for 360 degrees of light over the length of a fiber.

The type of light fiber can vary, and can include traditional fiber optics, telecommunication fiber, or plastic fiber optics that can be efficient in the transmission of light with minimal light loss. It should be noted that with any form of diffusing/diffusion light fiber, the intensity of the light will decrease over length of the fiber dependent upon the amount of light being diffused (length and/or area).

A process of even diffusion of the light in the cladding over the length of the fiber results in stronger intensity at the initiation end of the fiber and an ever decreasing amount as distance is increased from the initiation source. This reduction in optical power and intensity negates it's use in the curing of photodynamic implants, as the intensity at the distal end has weakened significantly (or the increased power to achieve curing at the distal end of the fiber has been increased so significantly that there is an overpowering of the fiber at the proximal end). Thus, a variable helix of a cut in the cladding, spiraling down the fiber, with the spiral getting tighter and tighter as the light is bleeding out allows for even light dispersion over the length of the fiber.

In some embodiments, an antimicrobial system can include an optical fiber having a diameter in the range of 1 mm to 20 mm, with a light emitting helical coil on the circumference of the fiber. The illumination of the fiber is delivered radially from the fiber outwards. Illumination frequencies are in the visible spectrum from about 400 nm to about 475 nm.

Figure 14A:
FIG. 14A and FIG. 14B shows that a reflective surface is added to the distal tip of a light fiber.
Figure 14B:
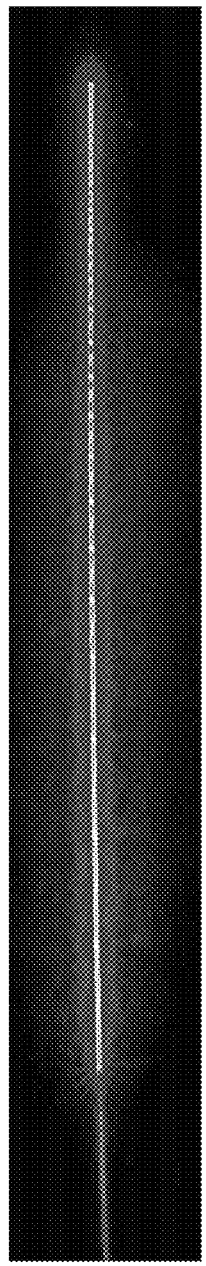
Figure 15A:
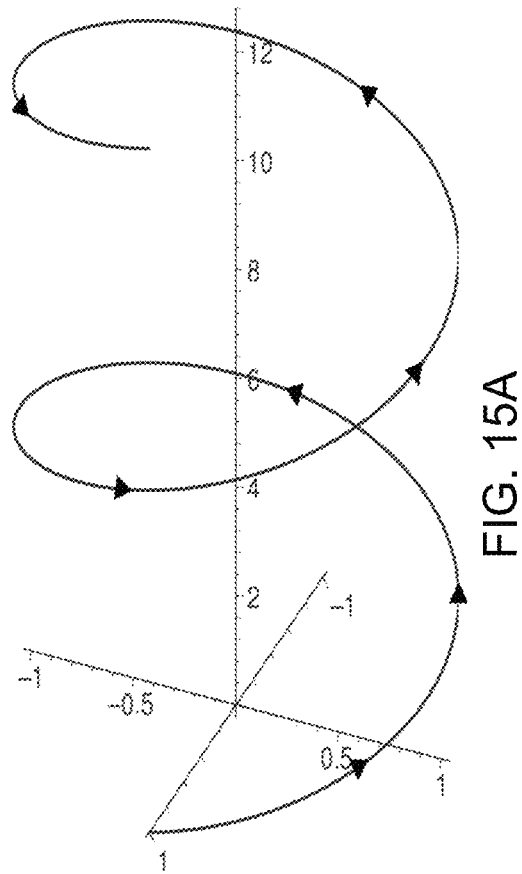
FIG. 15A, FIG. 15B, FIG. 15C, and FIG. 15D shows various views of an exemplary embodiment of a fiber with cladding removed in a spiral.
Figure 15B:
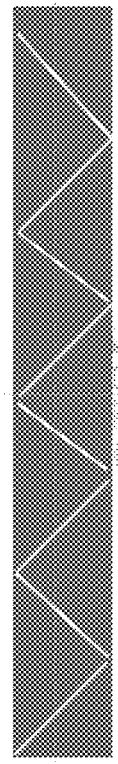
Figure 15C:
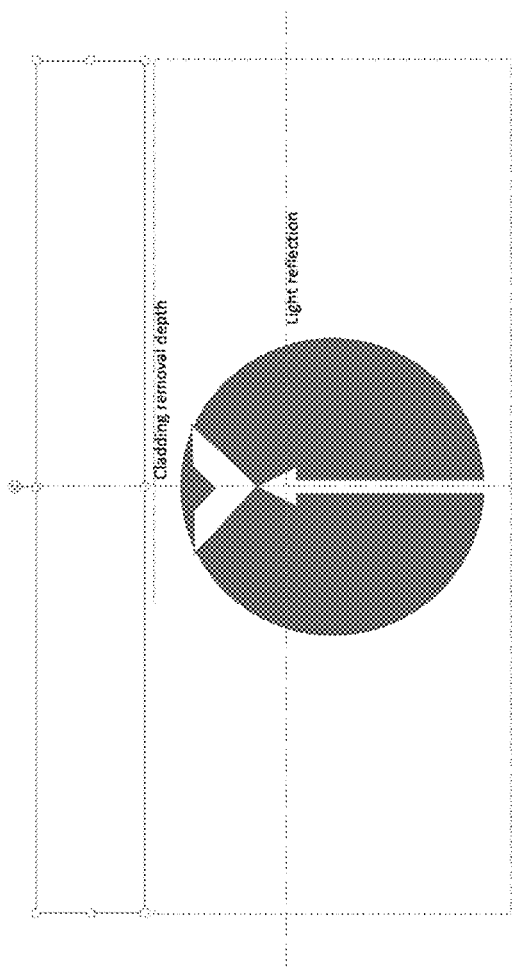
Figure 15D:
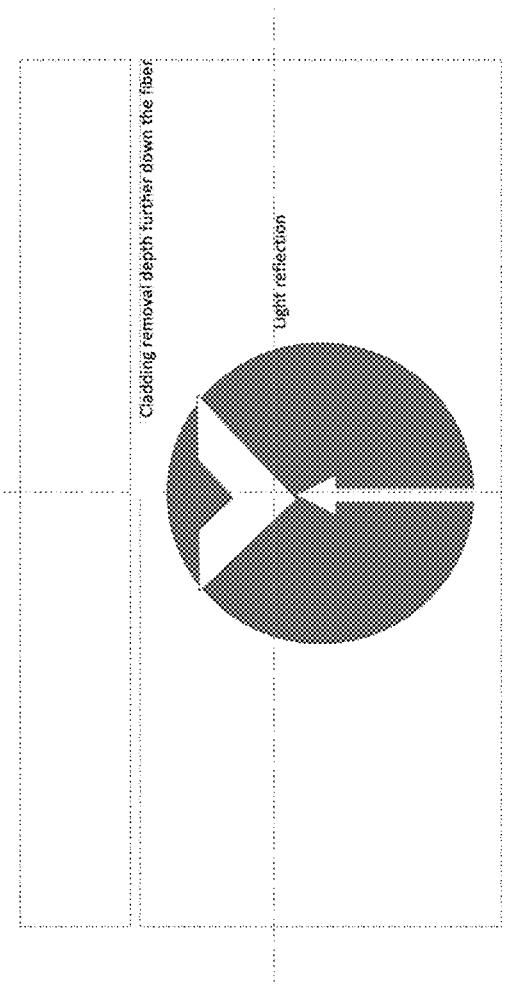

Thus, in some embodiments, a fiber 450 can have a spiral/helical coil of cladding that can be removed, allowing light to escape from within the fiber to affect the ABLP process, as shown in FIG. 14A and FIG. 14B. The cladding is removed such that the light intensity along the length of the fiber is uniform. Traditionally, PMMA (acrylic) comprises the core (96% of the cross section in a fiber 1 mm in diameter), and fluorinated polymers are the cladding material. Since the late 1990s much higher performance graded-index (GI-POF) fiber based on amorphous fluoropolymer (poly(perfluoro-butenylvinyl ether), CYTOP) has begun to appear in the marketplace. Polymer optical fibers are typically manufactured using extrusion, in contrast to the method of pulling used for glass fibers.

In some embodiments, cladding is removed physically (i.e., scratching the surface in a very precise method using, for example, a diamond tipped cutting head, a razor, or scalpel blade) which can reveal the fiber and allow light to emanate through the space in the cladding In some embodiments, cladding is removed chemically from a polymer optical fiber using organic solvents which can also be used to create etched portions of the fiber allowing the attenuation of light. Cladding can also be removed using low energy lasers to finely ablate the surface, water jet cutting, or with compressive dies to penetrate/break the surface of the cladding.

To provide for uniform light delivery, when the cladding is removed along the length of the fiber, the spiral can tighten as it progresses from a proximal end of the fiber to a distal end of the fiber. In some embodiments, the depth of the cut into the fiber can also increase from the proximal end of the fiber to the distal end of the fiber.

The greater penetration depth of the fiber towards the dispersion of light requires increased penetration depth as the light intensity also decreases through the attenuation or loss of light though the removed cladding area.

For example, a spiral design, as shown in FIG. 15A, FIG. 15B, FIG. 15C, and FIG. 15D, can be used that wraps around the fiber on the line of the spiral, where the the cladding has been removed to allow light to escape. As the light escapes, the intensity of the light being emitted is reduced from 100% of the light at a proximal end of the fiber closest to a light source, and the light moves distally further and further down the spiral, there is less light coming out of the fiber (the light intensity decreases). In order to resolve the issue, the pitch can be increased to narrow the gap between the two spirals and to increase the amount of light hitting the target. However, as the light moves further and further down the fiber and the intensity is dropping, the depth of the cut in the cladding can be increased to decrease the distance that the light within the fiber needs to transit before exiting the fiber. Thus, in order to achieve the necessary amount of light along the entire fiber length, there is a balance of the spiral and the depth of the cladding cuts to achieve an even light distribution over the length of the fiber. For example, an initial cut in the fiber can be shallow such that only the cladding is removed. The cuts can become deeper distally along the length of the fiber (i.e., thousands of an inch deeper).

In some embodiments, the cut in the cladding can also vary in depth, with the proximal aspect of the fiber cut only a minimal depth (for example, ~10 micron depth) to allow the light to pass through to an increasing depth of cut as the spiral moves down the length of the fiber. This is illustrated in plots based on pitch (mm), cutter rpm and cutter amps, with the increased amps yielding a deeper cut.

Figure 16:
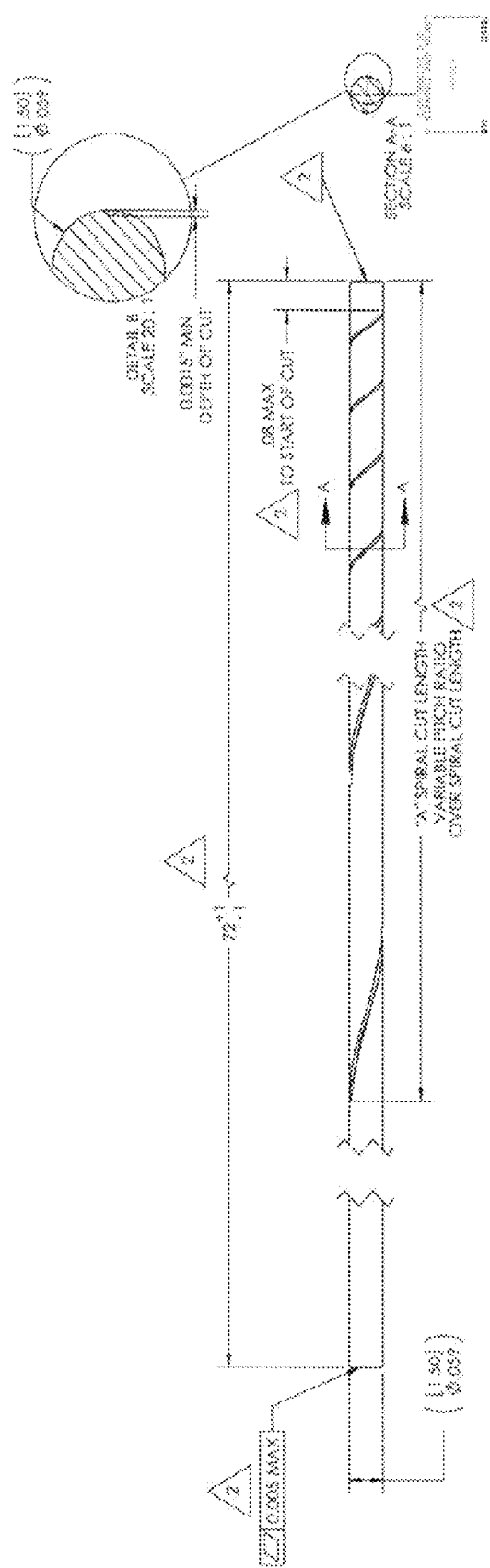
FIG. 16 shows an exemplary embodiment of a fiber with a portion of the cladding removed.

In some embodiments, the removal process includes holding the fiber in a rotary chuck with the cutting point mounted on a motor. A spring position can be used to advance the pointer and make contact with the cladding, and the spring drive holds the pointer in contact with the fiber. While the increased pitch and cutter rpms are applied, the cutter system is rotated around the fiber to apply the spiral cut (as does the increased depth of the cut), as shown in FIG. 16. As shown in FIG. 16, there is an increasing helical pitch, including a slow/shallow pitch at the proximal end and a very tight pitch at the distal end. It will be understood that the pitch becomes tighter from the proximal end to the distal end of the fiber. Further, the depth of the cut increases as the cut progresses down the length of the fiber from the proximal end to the distal end.

Figure 17:
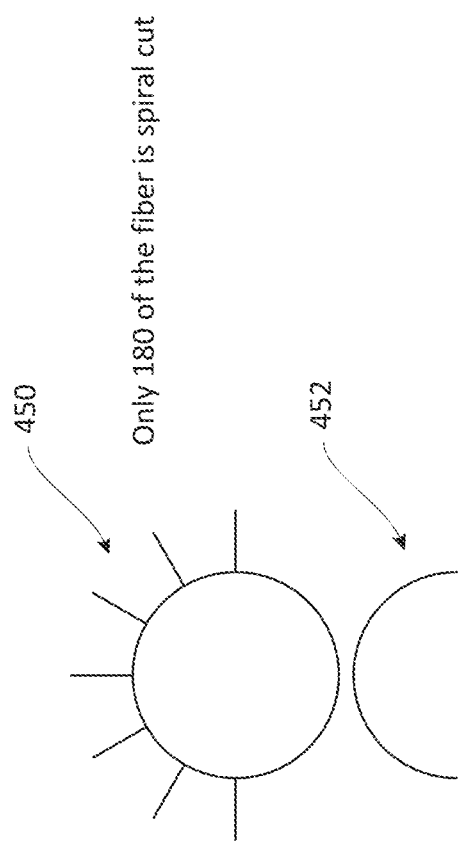
FIG. 17 shows that in some embodiments, the cladding is removed 360 degrees around the fiber; and in some embodiments, the cladding is only removed in a 180 degree orientation with the cut side outwards.

In some embodiments, the cladding is removed from only certain portions of the fiber. In some embodiments, the cladding is removed 360 degrees around the fiber. In some embodiments, the cladding is only removed in a 180 degree orientation, as shown in FIG. 17, with the cut side outwards. As shown in FIG. 17, the uncut side of the fiber 450 can be positioned against a balloon 452. The 180 degree cut side is exposed to the endosteal surface. By having the spiral cut only on 180 degrees of the fiber, the intensity of the light increases. The reduction in the cut cladding can increases the output efficiency. In some embodiments, the cladding is removed in a 90 (45+/−) degree orientation, with the 90 degree cut side exposed to the endosteal surface. This reduction in the cut cladding can also increases the output efficiency. In some embodiments, the cladding is removed in a 120 (60+/−) degree orientation, with the 120 degree cut side exposed to the endosteal surface. The reduction in the cut cladding can increase the output efficiency. It will be understood that any amount of the circumference of the cladding can be removed from the fiber to control the amount of light from the fiber and the area of tissue being exposed thereto. The cladding can be removed in the direction of intended light delivery.

Based on cladding removal, as shown in FIG. 16, energy dissipation remains the same or substantially the same as length increases. Cladding cut width is same, but the depth of cut increases over the length so light emanates stronger toward the distal end. A helical spiral can be cut with a slower pitch at proximal end, and the pitch can increase as it moves toward the distal end, creating a tighter spiral.

In some embodiments, rather than removing a portion of the cladding from the fiber to achieve uniform light energy delivery/power deposition along the length of the fiber, one or more fibers can be used to deliver the light energy uniformly does not include cladding. When using a fiber without cladding, the fiber can be overcoated with a light diffusing membrane. The over coating can be applied (or an extrusion) where the leaking of light through the diffusion membrane is low at the proximal end of the fiber (or light intensity side) and the diffusion can gradually increase as the fiber gets longer towards the distal end of the fiber. The outer membrane can be scaled to allow for uniform/even light and power deposition along the length of the fiber.

A diffusive membrane can be deposited in specific thicknesses or patterns on the fiber to achieve uniform delivery of light. In some embodiments, segments of diffusive material can be applied to the outer surface of the fiber in an arrangement that provide uniform light along the length thereof. In some embodiments, a diffusive coating (e.g., a spray coat, dip coat, or ionic deposition coating) can be applied to the fiber such that the thickness of the coating decreases along the length from the proximal end to the distal end of the fiber. The thinning of the coating towards the distal end allows for an increase in the amount of light diffusion through the coating from the proximal to the distal end such that the end result is uniform delivery of light along the length of the fiber. As described herein throughout the disclosure and the various embodiments, the energy across the length of the fibers (the linear deposition of even power) is uniform such that the bacteria or other microbe at the treatment site will be killed at an even rate.

Exemplary characteristics of PMMA plastic optical fiber (POF):
- PMMA and polystyrene are used as the core, with refractive indices of 1.49 and 1.59 respectively.
- Generally, fiber cladding is made of silicone resin (refractive index ~1.46).
- High refractive index difference is maintained between core and cladding.
- High numerical aperture.
- Have high mechanical flexibility and low cost.
- Industry-standard (IEC 60793-2-40 A4a.2) step-index fiber has a core diameter of 1 mm.
- Attenuation loss is about 1 dB/m @ 650 nm.
- Bandwidth is ~5 MHz-km @ 650 nm.

The cladding of POF is a thin, embedded/impregnated layer to maintain the light within the core. The cladding can be very thin (for example, 10 micron) in standard 1 mm step index. A diamond pointer, such as a diamond blade or other "super sharp" edged device can be used to remove a small very thin amount of the cladding from the fiber.

The use of multistrand optical fibers all held in contact proximity with that of a light source, where the termination end of the emitter faces of the fibers are aligned with reflective shapes within the tube to cause the even dispersion of light over the length of the system as each individual light fiber is delivering the originating energy amount.

The fibers are of different lengths, and each specific length fiber or fibers terminates on or near the reflective face of the intermediate light diffusion member A light-dispersing element with the cladded surface designed to contain the light within the element is modified so as to evenly bleed out light.

The light-diffusing element can include a surface coating which acts as a scattering surface coating The coating can be comprised of a phosphor, a fluorophore, etc.

The light dispersing element can be coupled to efficiency deliver light from LED sources.

Short segments of light-dispersing elements can be mounted on the face of LEDs, with multiple segments comprising a chain to thereby construct a length to provide sufficient and even energy deposition.

The light element may be a glass rod that includes a plurality of internal voids such that when light is directed through the element the voids cause the light to be scattered in a transverse direction, exiting the lateral surface of the element to provide a broad-area illumination effect.

The light element can be configured to be a flexible or malleable rod. In some embodiments, the rod can be rigid or it can be bent in a gentle curve/curves.

The light fiber can be constructed as a two part system having an inner fiber which is merely a plastic fiber conductor (without the traditional cladding) and an outer layer, a tube, that created intimate contact with the inner plastic fiber, that functions as a cladding.

The outer layer can be applied to the inner fiber and can have a surface coating which acts as a light scattering surface. The means of light scattering is either a coating of or an infusion of nanoparticles in an extrusion. For example, the coating may be comprised of a phosphor or a fluorophore to affect the scattering.

As previously mentioned, the bleeding out of light results in a continual loss of light intensity, and over the length of the fiber, results in a loss of roughly 90% intensity over a 10 length distance (nonspecific length) hence the proximal end is far more intense than that of the distal end. To prevent this imbalance of light, which would preclude the fibers use in either curing or delivery of antimicrobial blue light, a modification to the coating can be used.

Figure 18:
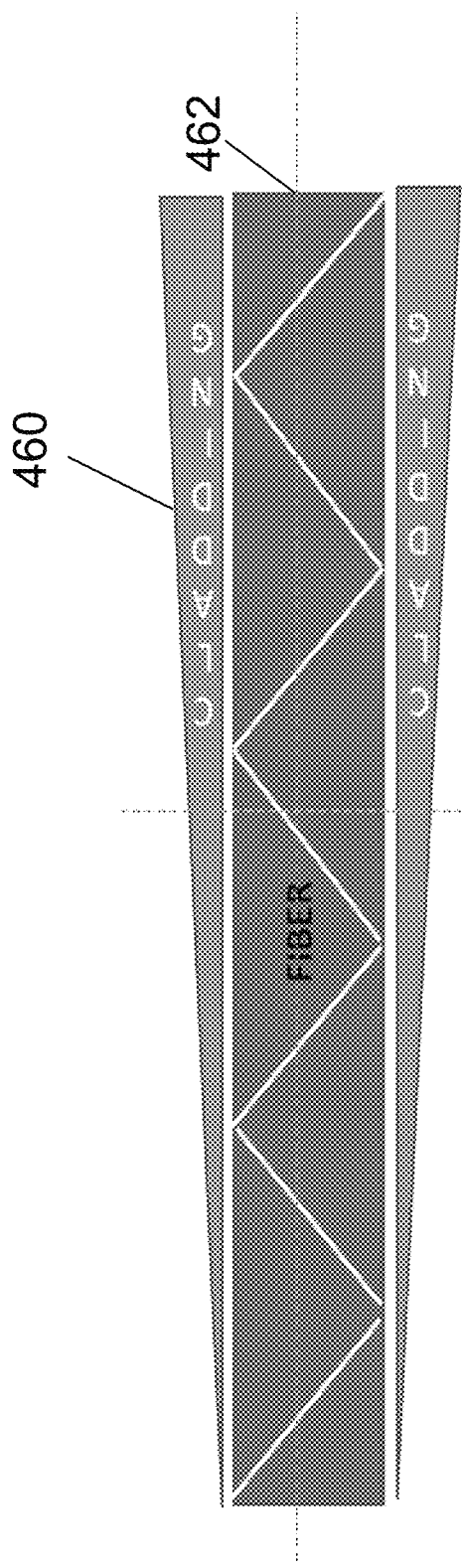
FIG. 18 illustrates an exemplary fiber having cladding that changes depth along the length of the fiber.

In some embodiments, the modification to the coating is that it can be thicker or less transparent to minimize light transmission through the fiber (and decrease loss) at the proximal end of the fiber, as shown in FIG. 18. The coating or cladding 460 can decrease in thickness from the proximal end to the distal end of the fiber 462, increasing the transmission at the end of the fiber. For example, it can be assumed that the amount of light transmission through the cladding is sufficient at the proximal end and can match to the amount of light transmission at the distal end.

The applied outer layer extrusion has a tapered or variable delivery of the nanoparticles, with the proximal end of the coating having a greater percentage of non-diffusion particles and more opacity, and with the distal end of the coating having more diffusion particles and less opacity. In some embodiments, the nanoparticles have a cross-sectional dimension of at least 25 nm. The nanoparticles have an average transmittance, per mm thickness, over the wavelength range from 400 nm-700 nm of greater than 90%.

The light-diffusing optical fiber coating, where the secondary coating layer of the extrusion is the outermost coating.

The cladding may be glass or a polymer. Cladding glasses include silica glass or modified silica glass. Cladding polymers include, but are not limited to, acrylate polymers, or fluorinated variants thereof (fluoroacrylate polymers).

Delivering Light to Cavities of the Bone

The light can be delivered to the bone using a variety of mechanisms.

Figure 19:
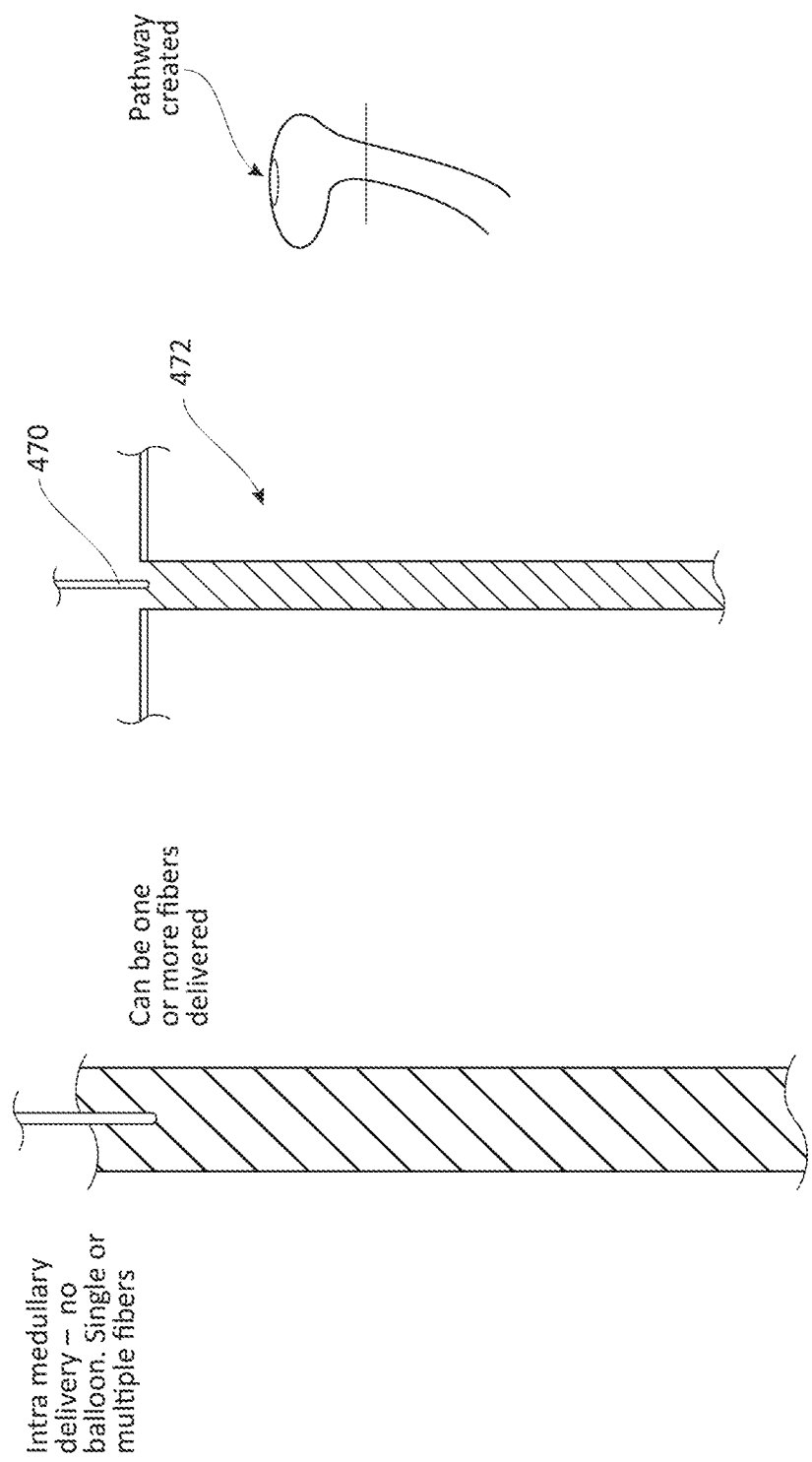
FIG. 19 shows that the surface treatment of wounds or the use in conjunction with procedures that require larger area coverage of the ABL light can be achieved by creating a "wand" from the light fibers.

In some embodiments, one or more fibers is configured to deliver the light (the removal of the cladding in the traditional spiral fashion). For small diameter canals, for example metacarpals, metatarsals, shaft of the ulna, the one or more fiber are straight. A passageway is created into the bone and the fiber can be fed into position. For larger diameter canals, the one or more fibers are heat set in a coiled configuration similar to the thread on a screw or a bolt, as shown in FIG. 19. Coiled fibers 470 are delivered into the canal via a sheath 472 where the sheath holds the precoiled fiber in a straight linear fashion and the removal of the sheath has the coiled fiber regaining the spiraled/coiled form down the length of the bone. The coiled system expands and achieves intimate contact with the endosteal surface.

In some embodiments, a plurality of fibers can be bundled together and used to deliver light along the length of the treatment site such that each fiber or subsets of the fibers in the bundle are cut to different lengths. All the fibers in the bundle are illuminated with a single source and the light energy delivered by each fibers at its tip are equal, but because the lengths of the fibers vary the light will be delivered uniformly along the length of the bundle of fibers from the shortest fiber in the bundle to the longest fiber in the bundle.

In some embodiments, it is possible to pulse the light delivered to the treatment site (tissue and/or bone) with intervals of higher power densities or by turning the light source on and off rather than a constant application of light. This can be useful for disinfecting large amounts of CFUs, and/or improving the efficiency of the disinfection process, and/or combating aggressive or robust forms of pathogens. Additionally, by adjusting the power density and the exposure time, the total energy density delivered to the pathogen sample may be adjusted. By pulsing the power, the correct dose of light can be delivered, or sequential doses of light can be delivered over a period of time. This can be done with systems that can be hardwired or plugged into a power source, or with a system that utilizes batteries or other portable power sources. The variability of the delivery of power to the system to control the duration and timing of the delivering of time can also be used for long term treatment, for example in a portable or wearable version such as bandages, or within indwelling catheters (e.g., urinary catheters), as described herein.

In some embodiments, the exposure time for each pulse of light in a time interval may be greater than the off period of time. In some embodiments, the exposure time for each pulse of light is less than the off period of time. Similarly, while the term "off period of time" is used herein with reference to a period of time where no light is output to the pathogen sample, one skilled in the art may configure the pulsed light output by the blue-violet light delivery system (or one or more light diffusing optical fibers) to have a first power density during a first exposure time followed by a second power density during a second exposure time that is different than the first power density. Furthermore, both the first power density and the second power density may be greater than 0 mW/cm2.

Figure 20:
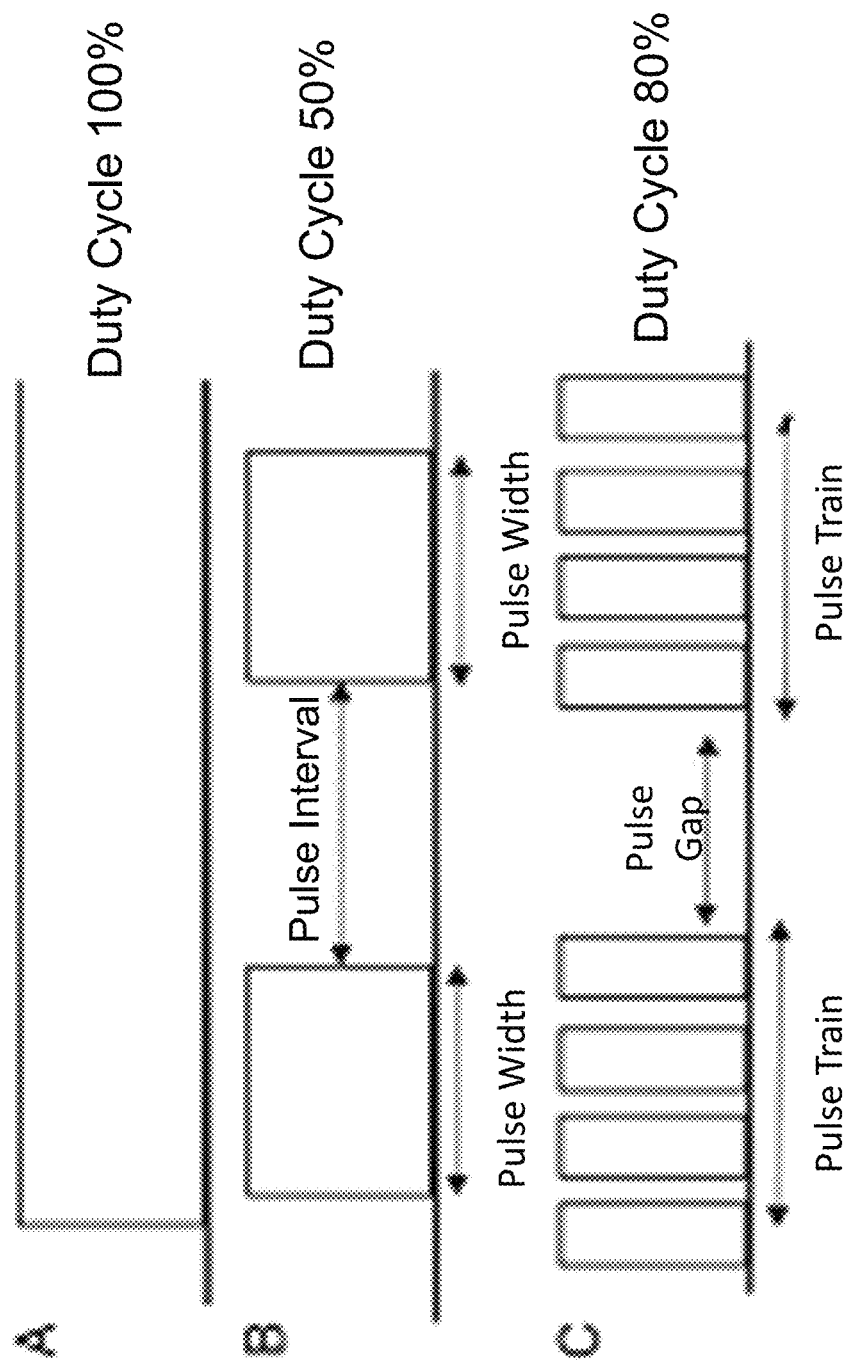
FIG. 20 illustrates exemplary modes of light source operation that can be continuous or pulsed.

FIG. 20 illustrates exemplary modes of light source operation that can be continuous or pulsed. The pulsing characteristics can be defined by the pulse duration (width), reported in seconds; pulse intervals, reported in seconds; and pulse frequency (number of pulses per second, in Hz). In more sophisticated pulsing sequences, especially in ultrafast pulses (nanoseconds, picoseconds, or femtoseconds), a series of pulses termed the pulse train are followed by a pulse gap. This is usually reported as time (e.g., picoseconds). The duty cycle refers to the time the beam is on during entire treatment. For a continuous wave, this is 100%, although it can vary significantly with pulsing regimens.

The fiber may be delivered within the canal in a variety of ways. In some embodiments, a hollow cannula is delivered within the canal and the fiber is introduced within the lumen of the cannula. The cannula can then be removed from the canal, e.g., slid backwards, over the fiber so as to allow the fiber to be exposed within the canal. The cannula can be metal or plastic, and can be stiff or malleable to allow appropriate delivery. The strength and stiffness of the cannula dependent upon the area of the body anatomy requiring the requisite force to delivery it.

The delivery system is capable of irrigation and aspiration of fluids, and the light system can be used in conjunction with an intramedullary reaming or surgical irrigation aspiration system. The fluids can be water, H2O2, acetic acid, povidone iodine, one or more essential oils, or a combination of antibiotics (irrigation of low concentration of H2O2, with concentrations of high does H2O2). The delivery port for the fiber may have an irrigation port at the entrance point to the bone and a longer aspiration point catheter that is further down the length of the bone. The irrigation aspiration can be continual during the process to provide a clean canal to ensure that the light fiber is not covered or occluded with intramedullary materials.

In some embodiments, the use of the light system in conjunction with essential oils, H2O2, acetic acid, and/or povidone iodine provides antimicrobial effect. Essential oils/photosynthesizers can be used to impregnate or identify the bacteria such that the bacteria become charged to allow for more effective blue light treatment. With some bacteria, the blue light can be used to damage the shell of the bacteria, and the essential oils or peroxide then can break down the bacteria further. In some embodiments that include an inflatable balloon, the balloon can include an edge or a lip such that the solution (i.e., an essential oil) can be poured over the balloon to impregnate the balloon with the solution for treating a specific bacteria.

For example, the association of aminoglycosides with the blue LED light and essential oils can be used against resistant bacteria.

The essential oils of aegle, ageratum, citronella, eucalyptus, geranium, lemongrass, orange, palmarosa, patchouli and peppermint, were tested for antibacterial activity against 22 bacteria, including Gram-positive cocci and rods and Gram-negative rods, and twelve fungi (3 yeast-like and 9 filamentous) by the disc diffusion method. Lemongrass, eucalyptus, peppermint and orange oils were effective against all the 22 bacterial strains. Aegle and palmarosa oils inhibited 21 bacteria; patchouli and ageratum oils inhibited 20 bacteria and citronella and geranium oils were inhibitory to 15 and 12 bacterial strains, respectively. All twelve fungi were inhibited by seven oils (aegle, citronella, geranium, lemongrass, orange, palmarosa and patchouli). Eucalyptus and peppermint oils were effective against eleven fungi. Ageratum oil was inhibitory to only four fungi tested. The MIC of eucalyptus, lemongrass, palmarosa and peppermint oils ranged from 0.16 to >20 microliters ml-1 for eighteen bacteria and from 0.25 to 10 microliters ml-1 for twelve fungi.

The coiled system can be left in place for a single dose of light or for longer periods of time (i.e., for multiple days) to achieve multiple doses of light. The entry point of the light fiber into the canal is a medical grade antibiotic covering to preclude incremental bacteria or the transmission of materials into the canal. The irrigation aspiration catheter can be left in place during the illumination and can be removed post the illumination where the irrigation port may allow the infusion of antibiotics. The system may be left in place for a period of days so that multiple activations of light can be applied, and the irrigation port can be used to provide continual drip/or small dose of antibiotics within the canal of the bone.

The external aspect of the fibers (those outside of the anatomy) are contained within a supportive sheath so as to protect them, for example to prevent accidental breakage. The delivery port for the light fiber for the indwelling catheter is sealed to the external environment around the light fiber, for example using a port. The sealed port allows for the ability to deliver intramedullary antibiotics or intramedullary fluids.

Multiple fibers delivered within the canal can be held in intimate contact to each other, for example, via clear bands, retaining clips, or other mechanism, or they can be delivered and released from the intimate contact to the other fibers.

Multiple fibers can be powered by multiple LEDs or a single LED. Power can be adjusted via the amount of time that the system is run. The system can be used to aspirate fluids from the canal. The system can be used to acquire intramedullary samples from the canal.

Fibers on outside of the balloon can be held in retaining tubes/columns or lumens on the outside of the balloon. The inside of the balloon or the outside of the balloon can be comprised of a reflective surface to enhance the light as extraneous light will be reflected to the endosteal surface.

Devices for Delivering Fibers for Treating Larger Areas

Figure 21:
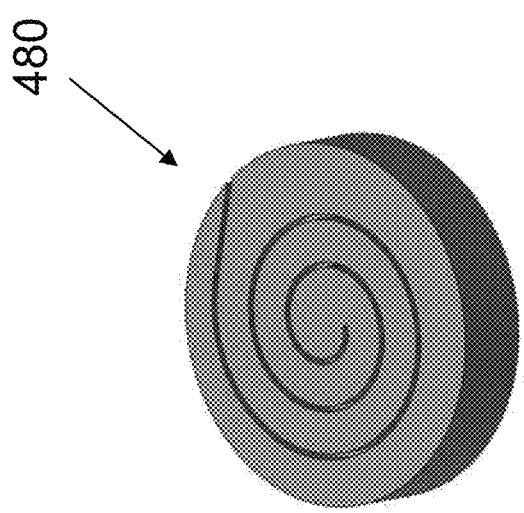
FIG. 21 shows an exemplary embodiment of a paddle with a plate-shape.

For surface treatment of wounds or use in conjunction with procedures that require larger area coverage of the ABL light, the light fibers can be built to create a larger structure such as a paddle 480, as shown in FIG. 21. The shape of the paddle can vary and can include a plate-shape as shown in FIG. 21, but it will be understood that the paddle can take any shape required based on the size of the area to be treatment and the size and shape of the area of the body into which the paddle is inserted. In some embodiments, the paddle holds a single fiber coiled. In some embodiments, the paddle holds multiple fibers coiled. The fibers contained within a paddle can be rigid or semi rigid so as to be malleable to take shapes as required.

The paddle can have one side that is optically clear and one portion that is opaque so that the light only emanates from the paddle in one general direction outwards. The size of the optically clear portion may be predefined. There may be a covering on the paddle that allows for adjustment of the open area that can be slidable, hinged, pivotable, or other means to cover and occlude the light from being transmitted outwards. The inner surface of the paddle on the opaque side can be a polished reflective surface that reflects and focuses the light from the one or more fibers outward.

The shape of the paddle surface can be that of an optical reflector so as to gain as much of the light from the rear of the fiber to be delivered outwards. These reflective shapes may follow the shape of the fibers that have been laid within the paddle such that each of the fiber sits within a curved reflective recess within the paddle. These reflective shapes may follow the shape of the fibers that have been coiled such that each of the fiber sits within a curved reflective recess within the paddle. A paddle can be a square, rectangle or circular form. The paddle variants therein can be used to deliver light during a surgical procedure where the wand is delivered within the surgical cavity to provide continual light to the affected tissues.

In some embodiments, the paddle (or any of the other shapes described herein) can be constructed to be malleable such that the paddle, wand, or other shape can be bent, shaped, and/or formed so it can be introduced within a cavity during an open procedure. For example, it can be affixed to a retractor or other instrumentation so that the light source is directed within an incision, or it can be shaped or bent as required to be placed within a bodily orifice.

Devices for Delivering Fibers to Confined Areas

Figure 22A:
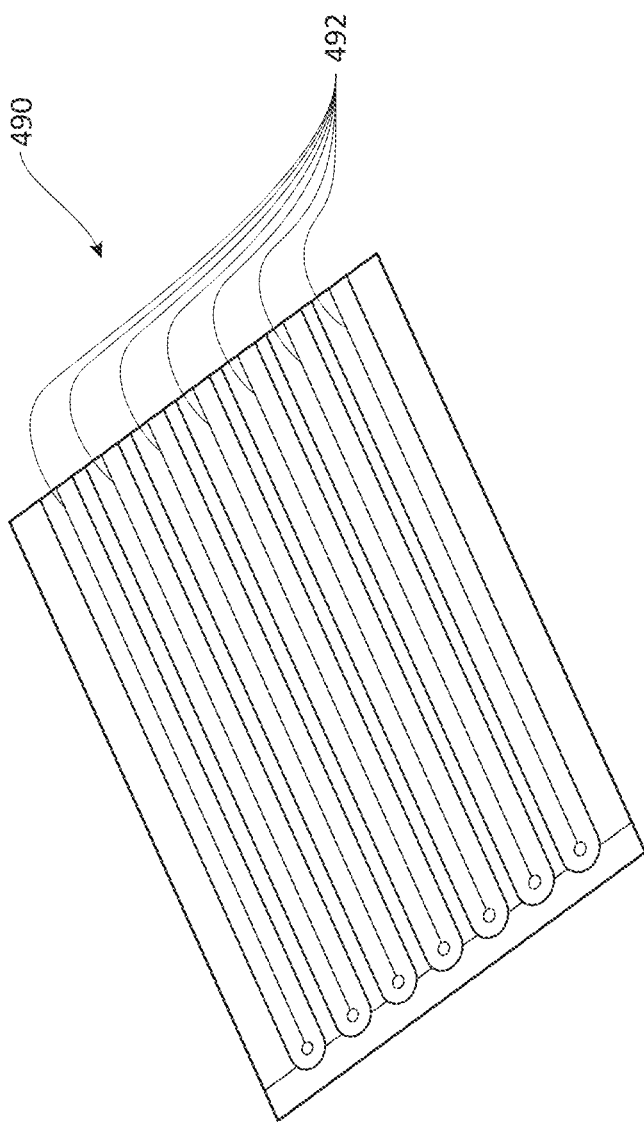
FIG. 22A and FIG. 22B illustrates an exemplary device providing an anti-microbial effect on a bone that can include a series of shorter length fibers.
Figure 22B:
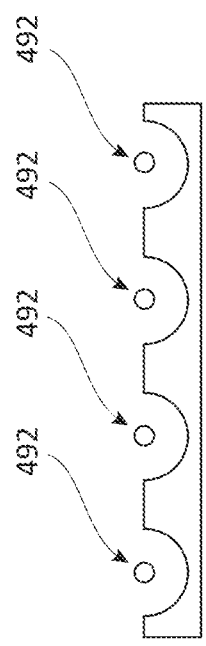

In some embodiments, a device can include a series of shorter length fibers 2-4 inches, or 3-5 inches, running in parallel (like a fork or a comb), as shown in FIG. 22A and FIG. 22B. FIG. 22A illustrates a top view of an embodiment of optical fibers 492 running parallel for form a comb-like structure 490. As shown in the cross-sectional view in FIG. 22B, each fiber run parallel and is positioned in a rounded opening that forms a focal reflector. In some embodiments, the fibers reside within focal reflectors, with one side being opaque and one side for illumination. The curved reflective shape directs the light that is not in the direction of the intended use and reflects and focuses it outwards.

Figure 23B:
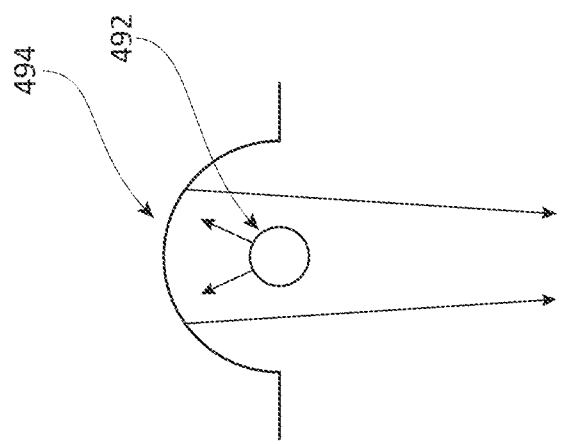
FIG. 23A and FIG. 23B illustrates an exemplary fiber positioned relative to a reflector.
Figure 23A:
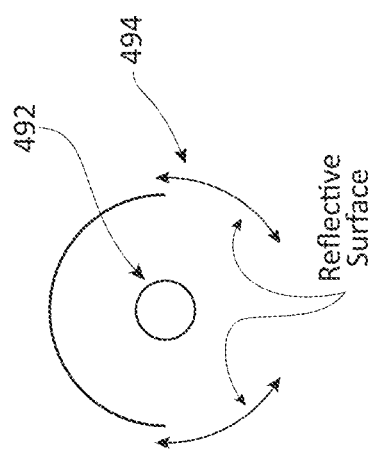

FIG. 23A represents the position of the fiber relative to the rear reflector (or reflective surface) 494. FIG. 23B illustrates the fiber 492 within the rear reflector, and showing the ability to adjust the opening exposure of the illumination area or close it completely using slidable shields 494 to block or focus the beam. For example, the reflector can include one or more gates to control and focus the amount of light affecting tissue.

Catheter with Wand Configuration for Delivering Fibers

Figure 24:
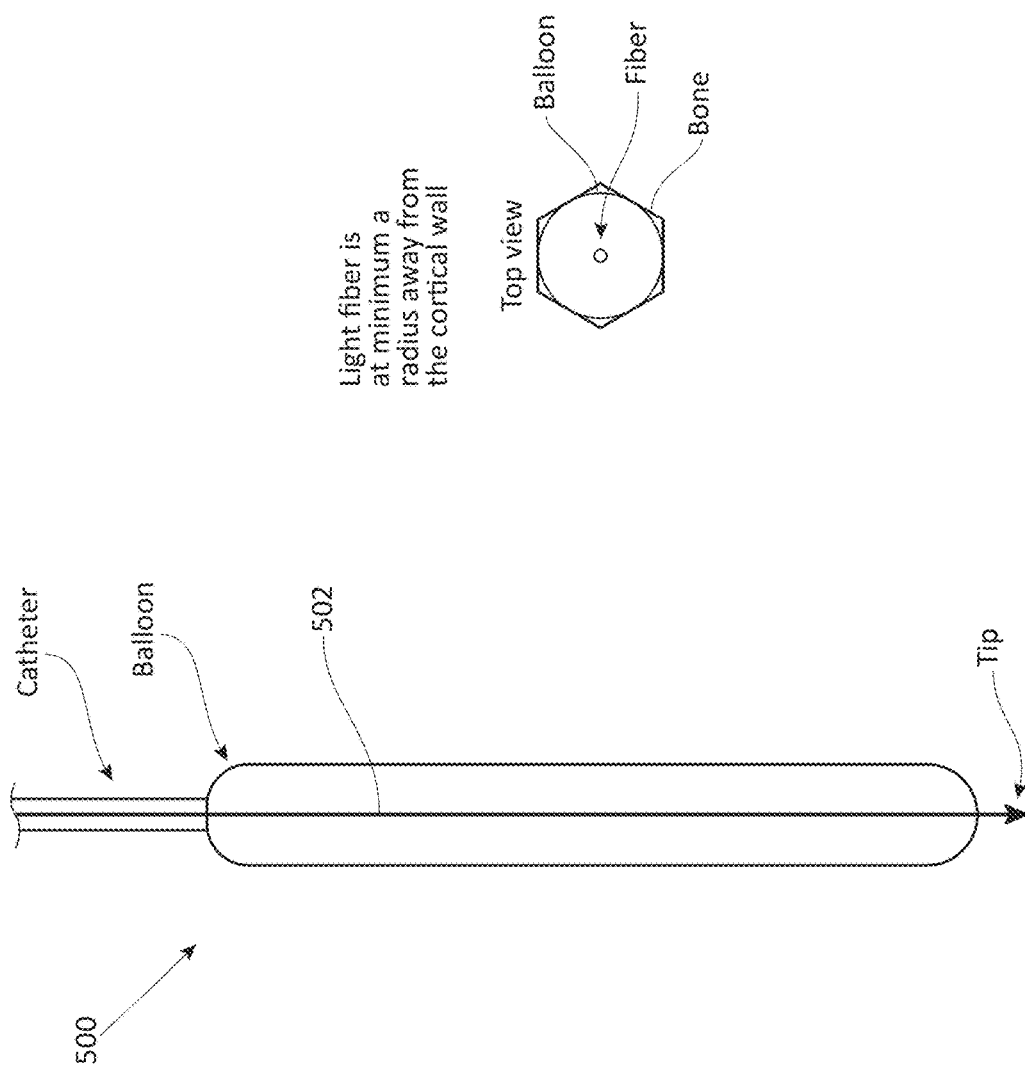
FIG. 24 shows an exemplary embodiment of a device for providing an anti-microbial effect on a bone.

The surface treatment of wounds or the use in conjunction with procedures that require larger area coverage of the ABL light can be achieved by creating a wand 500 from the light fibers 502, as shown in FIG. 24. The wand can hold a single fiber or multiple fibers. The fibers can be contained within a rod or tube. The wand can be in the form of a plate or other shape as needed and can be rigid or semi rigid so as to be malleable to take shapes as required. The rod/tube can have one portion that is optically clear and one portion that is opaque so that the light only emanates from the wand in one general direction outwards. The optically clear portion can vary in size, and for example may be 30 degrees, 45 degrees, 60 degrees, or 90 degrees. The optically clear portion may be predefined. There may be a covering on the wand that allows for adjustment of the open area, from a maximum of 90 degrees down to 15 degrees. The inner surface of the wand on the opaque side of the tube can be a polished reflective surface that reflects and focuses the light from the fiber/fibers outward. The shape of the wand/reflective surface can be that of an optical reflector so as to gain as much of the light from the rear of the fiber to be delivered outwards.

In some embodiments, the fibers can be placed within a large bore needle that includes areas where the sides of the needle are removed so as to permit illumination outwards. The bore needle allows the flexible fiber to be inserted/introduced into a depth of tissue so as to illuminate an area that is not exposed. In the case of a mass, such as a tumor or other defined area that needs to be illuminated, the bore needle allows the introduction of the fiber to be delivered to points and locations where the flexible fiber does not permit insertion. The cut away of the needle provides illumination such that the bore of the needle can be withdrawn while leaving the fiber within the body. The bore needle can permit access to areas where the fiber alone might not be able to be delivered but access needs to be made in a minimally invasive fashion.

Catheter with an Inflatable Member

According to aspects of the disclosed subject matter, a method for providing an anti-microbial effect on a bone comprises gaining access to a cavity in a bone; delivering in an unexpanded state, an expandable member having at least one channel to the cavity in the bone; infusing the at least one light sensitive liquid in the expandable member to move the expandable member from a deflated state to an inflated state, positioning an optical fiber sufficiently designed to emit light energy along a length of the optical fiber inside the at least one channel in the expandable member; activating a light source engaging the optical fiber; and delivering light energy from the light source to the optical fiber to providing an anti-microbial effect on a bone In some embodiments, an inflatable member, such as a balloon, can be delivered in an uninflated fashion. The balloon can be inflated using a variety of substances, including air or water, to expand the balloon against the endosteal surface of the bone. A light source can be activated, and the energy delivered to the bone and/or bacteria. As shown in FIG. 25A, if a balloon 510 is utilized, in some embodiments the fibers 512 are located outside of the balloon such that when the balloon is inflated, it expands and distends the balloon shape so that the fibers are pushed outwards. FIG. 25B illustrates a top view of the fibers 512 located circumferentially on the outside of the balloon 510. This allows for the fibers to be direct or close contact with the endosteal surface (inside of the bone wall). The intimate or close contact can increase the effective power of the light as it is closer to the wall (less loss of power via distance). In some embodiments, the outer surface of the balloon and/or the interior of the balloon can be mirrored or include a reflective portion so as to enhance the delivery of light from the fibers.

In some embodiments, utilization of a balloon can act to increase spatial volume and reduce fluid volume. A reduction in the treated volume can result in an increase in the energy deposition, and that the increase in volume can result in more of the fiber transmitting light to the fluid. The use of a balloon reduces the illumination energy (inverse square law). In some embodiments, the power per volume, due to the balloon displacement and lower sample volume, exceeds the losses due to illumination distance.

Two issues are at play here: power and volume. Distance as it relates to power can also be a factor. For example, if the energy is 500 units (undefined) and the volume of solution to be treated is 3000 (undefined), then the energy delivered per volume is 3000/500=6 volume units per 1 energy unit. The effective power per volume is ⅙. If the volume is reduced to 1000 with the same energy level, the effective power per volume is ½. A reduced volume of solution can provide more power per volume and more effective elimination of bacteria.

As one moves further away from the light source, the intensity decreases. Thus, the ability to increase the power can be to reduce the volume of solution in the balloon (where the volume per unit of energy is greater than the loss of intensity by distance). In some embodiments, the choice of balloon to achieve the reduction may be important. For example, a longer thinner balloon to achieve the reduction may be better than a larger diameter, where the volume is decreased but the distance to the source is so far that the intensity of the light has decreased.

The reason that the fibers in the balloon, or the fibers on the outside of the balloon, or the wand of light are important to the process is that they cause a reduction in the internal space of the materials within the canal, decreasing the distance that the light needs to travel to accomplish antimicrobial effect. Allowing for the fibers on the outside of the balloon achieves a decrease in the distance between the tissue and/or bone and the light for treatment.

Conversely, with the fibers on the outside of the balloon, the distance to the edges of the bone is reduced (for example, an 18 mm balloon and a 2 mm distance for the light to travel). Thus, as the balloon expands, the fibers on the outside of the balloon are pushed closer to the tissue and/or bone, which also decreases the distance between the fibers and the treatment site to achieve greater light illumination without having to increase the power. The fibers can be positioned on the outside of the balloon such that the fibers are moved towards the treatment site when the balloon is expanded.

In some embodiments, the number of fibers can be decreased if the fibers can be moved closer to the target site. This increases the intensity of the light from each fibers, resulting in the use of less fibers, but with the resulting intensity remaining substantially the same. The variables include power (driven power), distance which determines intensity, time (as time defines joules), and the number of fibers (more fiber decreases distance), and lateral distance between the next sequential fiber (thereby requiring each fiber to cover less area). Hence the fibers being in closer proximity to the bone makes the system significantly more efficient, but a light source of 2200 would have to be used to achieve the same effect as the 2 mm distance. The inverse square law applies when looking at the light source versus distance such that as the light source gets further away, the intensity decreases.

Of concern to the either high power or long duration run of the system where the joules are significant is the fact that interim located tissue may be impacted by the illumination at these lengths and powers.

In some embodiments, a light source can be positioned inside a light diffusion balloon that is used as the light delivery device. The balloon can have a nano surface to spread the internally reflected light. The light source can be powerful enough to provide the power in milliwatts to achieve the required joules at full expansion of the balloon. The light source can be comprised of a multistrand fiber (end fiber illumination) cut at increased length sections, with the segmented lengths of the illumination fiber providing even outward illumination. The light fiber can be a diffusion surface on a solid glass, sapphire, or other transmissive material. The light transmission system can have multiple reflective members to increase the transmission area of the light. The light is dispersed to the surrounding tissues/bone by the reflective members of the central light fiber. While the intensity of the energy delivered within the balloon may be "even," the diffusion surface ensures the even power distribution. The diffusion surface reduces the need for the precise power distribution of the light fiber. The internal surface of the balloon is reflective such that non attenuated light is reflected back into the balloon where it amplifies the energy. The surface can be a part of the balloon or an applied surface thereafter.

In some embodiments, a balloon with two walls can be used, such that the space between a first wall and a second wall contains one or more fibers that can be wrapped circumferentially around the balloon. The light fibers around the circumference can be positioned to deliver light, and fibers that are wrapped around the balloon are emitters, cut at different lengths so as to achieve the same amount of optical power at each cut surrounding length. The active portions of each segment are the same so via a multifilament stacking there can be equal optical intensity.

In some embodiments, the diffusing balloon catheter is a soft cylindrical balloon catheter with translucent diffusing walls. Used with an internal radial light diffuser, the diffusing balloon catheter, provides a homogeneous illumination of biological tissues in contact with the balloon walls. The compliant property of the balloon in contact with the walls of the bone or tissue, allows the balloon to adapt its shape to the geometry and consequently to provide an accurate dosimetry of light to the affected area. The balloon can be inflated with water to minimize refraction and adapts its shape to the internal diameter of the bone canal, or the balloon can be inflated with air or any other material capable of inflating the balloon and allowing the light to diffuse.

In some embodiments, there is a fitting at the base of the balloon tip that holds the fibers in position such that the side of the fiber without the cladding is held in position and emits light outward. The full cladded side is against the balloon. FIG. 25C illustrates an embodiment of the removed cladding on the fiber. There is a fitting at the catheter/top of the balloon where the fibers are located and constrained that they are in vertical alignment up the balloon so that the base of the fiber and the tip of the fiber are in alignment. In some embodiments, the constraining member is at the top of the balloon residing on the catheter. This allows the fibers to slide through the constraining member as the balloon is expanding and pulling the fibers. In some embodiments, as shown, the cladding to partially removed from the fiber but is not fully spiraled.

Referring to FIG. 1A, FIG. 1B, FIG. 1C and FIG. 2A and FIG. 2B, for the system to deliver the light to the cavity of the bone, the system 100 further includes a balloon catheter 110 having an elongated shaft 101 with a proximal end 102, a distal end 104, and a longitudinal axis there between. In an embodiment, the balloon catheter 110 can have an outside diameter ranging from about 3 mm (9 French) to about 8 mm (24 French). In larger diameter canals, for example, the femur or tibia, the OD of the balloon when inflated can be various sizes, including 22 mm. However, it is noted the balloon catheter 110 may have an outside diameter of about 3 mm (9 French). At least one inner lumen is incorporated within the elongated shaft 101 of the balloon catheter 110. The elongated shaft 101 of the balloon catheter 110 may include two inner lumens. The elongated shaft 101 of the balloon catheter 110 may include three inner lumens, four inner lumens or more. It is contemplated the one or more inner lumens may accept one or more optical fibers. The proximal end 102 of the balloon catheter 110 includes an adapter for passage of at least one of inflation fluids or medical instruments.

The distal end 104 of the balloon catheter 110 includes at least one expandable member 170. The expandable member 170 of FIG. 1A has a bulbous shape; however, the expandable member 170 may have any other suitable shape. It is possible, the at least one expandable member 170 includes multiple expandable members. For example, the distal end 104 of the balloon catheter 110 may include a first inner inflatable balloon positioned inside and completely surrounded by an outer inflatable balloon. In an embodiment, the expandable member 170 can be manufactured from a non-compliant (non-stretch/non-expansion) conformable material. In an embodiment, the expandable member 170 is manufactured from a conformable compliant material that is limited in dimensional change by embedded fibers. One or more radiopaque markers, bands or beads may be placed at various locations along the expandable member 170 and/or the balloon catheter 110 so that components of the system 100 may be viewed using fluoroscopy.

FIG. 1B and FIG. 1C show schematic illustrations of embodiments of a bone implant device. The devices include a balloon catheter 110 and an expandable member 170 sufficiently shaped to fit within a space, cavity or a gap in a fractured bone. It is contemplated the expandable member may be of any shape so as to fit within a space, cavity or a gap in a fractured bone. For example, the expandable members 170 of FIG. 1B and FIG. 1C can have a tapered elongated shape to fill the space, cavity or gap in certain fractured or weakened bones to be repaired or stabilized. In an embodiment, the expandable member 170 can have an antegrade shape as shown in FIG. 1B. In an embodiment, the expandable member 170 can have a retrograde shape as shown in FIG. 1C. In FIG. 1B, the expandable member 170 can have a larger diameter at its distal end than the proximal end. In FIG. 1C, the expandable member 170 can have a larger diameter at its proximal end than the distal end.

In the embodiments shown in FIG. 1A, FIG. 1B, and FIG. 1C, the proximal end of the balloon catheter 110 includes a first port 162 and a second port 164. The first port 162 can accept, for example, the light-conducting fiber 140 or multiple light-conducting fibers. The second port 164 can accept, for example, a syringe 160 housing a light-sensitive liquid 165. In an embodiment, the syringe 160 maintains a low pressure during the infusion and aspiration of the light-sensitive liquid 165. In some embodiments, the syringe 160 maintains a low pressure of about 10 atmospheres or less during the infusion and aspiration of the light-sensitive liquid 165. In some embodiments, the syringe 160 maintains a low pressure of less than about 5 atmospheres during the infusion and aspiration of the light-sensitive liquid 165. In some embodiments, the syringe 160 maintains a low pressure of about 4 atmospheres or less during the infusion and aspiration of the light-sensitive liquid 165. In some embodiments, the light-sensitive liquid 165 is a photodynamic (light-curable) monomer. In some embodiments, the photodynamic (light-curable) monomer is exposed to an appropriate frequency of light and intensity to cure the monomer inside the expandable member 170 and form a rigid structure.

Thus, the method may optionally include curing a light-curable fluid, such as a monomer, inside the balloon to harden the expandable member. In some embodiments, an optical fiber can be positioned inside the expandable member and the light source can be activated to deliver light energy to the optical fiber from the light source to cure the expandable member using the at least one light sensitive liquid that has been infused into the expandable member after light from the fibers has been used for an antimicrobial treatment.

FIG. 2A and FIG. 2B show close-up cross-sectional views of the region circled in FIG. 1. FIG. 2A shows a cross-sectional view of a distal end of the balloon catheter 110 and the expandable member 170 prior to the device being infused with light-sensitive liquid. FIG. 2B shows a cross-sectional view of the distal end of the balloon catheter 110 and the expandable member 170 after the device has been infused with light-sensitive liquid and light energy from the light-conducting fiber is introduced into the balloon catheter 110 and inner lumen of the expandable member 170 to cure the light-sensitive liquid.

As illustrated in FIG. 2A and FIG. 2B, the flexible balloon catheter 110 includes an inner void 152 for passage of the light-sensitive liquid 165, and an inner lumen 154 for passage of the light-conducting fiber 140. In the embodiment illustrated in FIG. 2A and FIG. 2B, the inner lumen 154 and the inner void 152 are concentric to one another. The light-sensitive liquid 165 has a low viscosity or low resistance to flow, to facilitate the delivery of the light-sensitive liquid 165 through the inner void 152. In an embodiment, the light-sensitive liquid 165 has a viscosity of about 1000 cP or less. In an embodiment, the light-sensitive liquid 165 has a viscosity ranging from about 650 cP to about 450 cP. The expandable member 170 may be inflated, trial fit and adjusted as many times as a user wants with the light-sensitive liquid 165, up until the light source 110 is activated, when the polymerization process is initiated. Because the light-sensitive liquid 165 has a liquid consistency and is viscous, the light-sensitive liquid 165 may be delivered using low pressure delivery and high pressure delivery is not required, but may be used.

In some embodiments, the expandable member can be trial fit into a space within a bone by alternatingly moving between a deflated state and an inflated state by a fluid, such as water, air, or a light sensitive liquid. The expandable member is designed to be at least partially placed into the space within the bone, and directly in contact with the bone and to form fit to a surface contact area within the space of the bone. A light conducting fiber sized to pass through the inner lumen of the delivery catheter and into the expandable member to disperse light energy to provide an anti-microbial effect. In some embodiments, subsequently a light sensitive liquid can be infused into the expandable member, and the light conducting fiber can be positioned in the expandable member to initiate hardening of the light sensitive liquid within the expandable member to form a photodynamic implant of a size and a shape so the bone is restructured to a substantially original size and an original shape around the formed photodynamic implant.

FIG. 2C and FIG. 2D show a close-up cross-sectional view of the region circled in FIG. 1B and FIG. 1C, respectively. FIG. 2C and FIG. 2D show cross-sectional views of a distal end of the balloon catheter 110 and the expandable member 170 and a light-conducting fiber 140 with a cut 141 in the fiber in the balloon catheter 110 and inner lumen of the expandable member 170. The device also has a separation area 172 at the junction of the balloon catheter 110 and the expandable member 170 where the balloon catheter 110 may be separated from the expandable member 170.

Channels within the Expandable Member for the Optical Fibers

Figure 26:
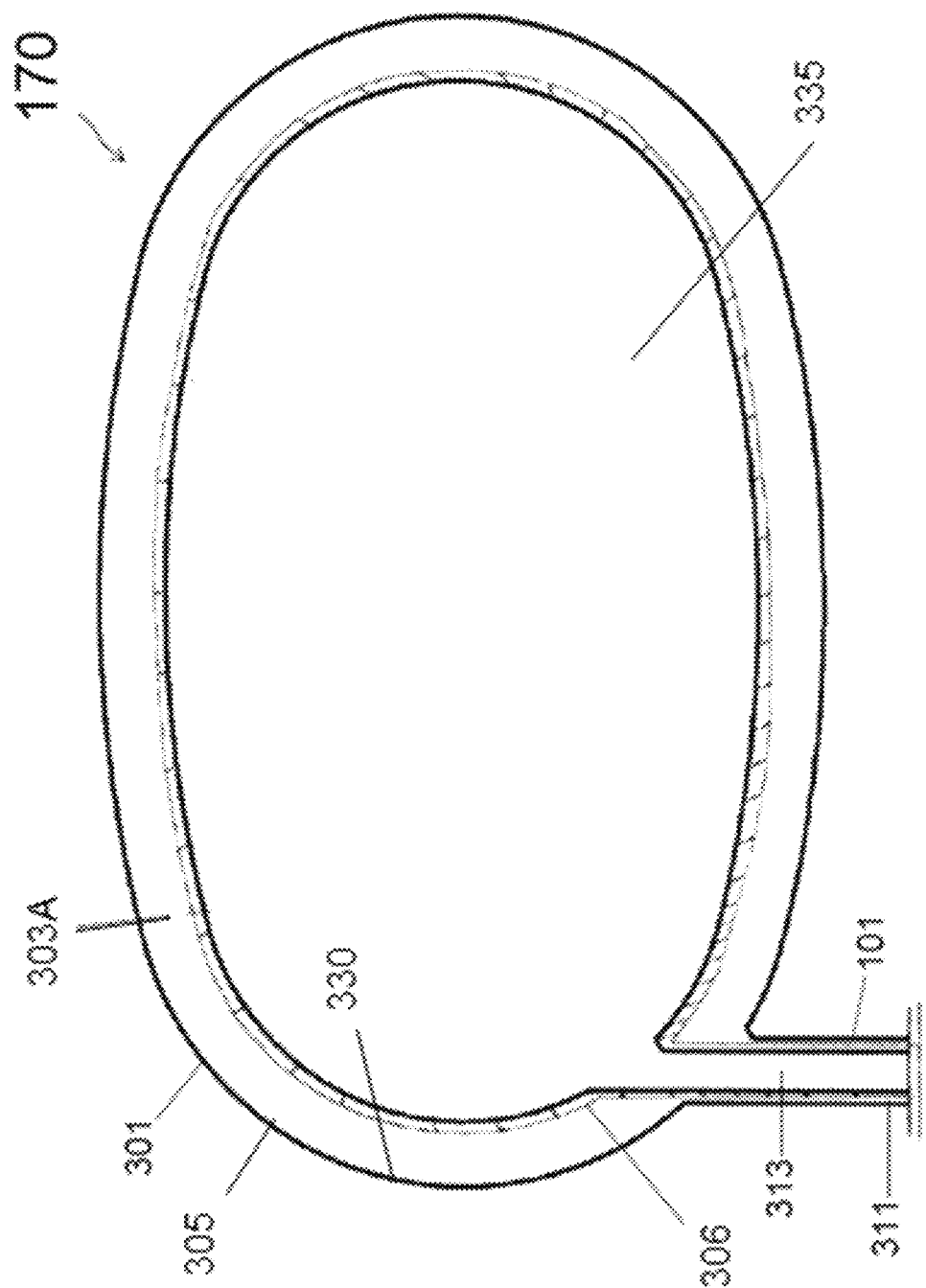
FIG. 26 shows an exemplary embodiment of a distal end of a balloon catheter in commutation with expandable member.

FIG. 26 shows a view of another embodiment of a distal end of a balloon catheter of the present disclosure. The distal end of the balloon catheter includes expandable member 170, which comprises an inflatable balloon 301. The inflatable balloon 301 has a wall with an outer surface 305 and an inner surface 330. The inner surface 330 defines an inner cavity 335.

Further, at least one channel 303A is located in the cavity 305 of the inflatable balloon 301 approximate the inner surface 330 of the inflatable balloon 301. The balloon catheter includes an elongated shaft having a first inner lumen 311 in fluid communication with the expandable balloon 301 which is also in communication with the at least one channel 303A. A separate optical fiber 306 can be incorporated within the elongated shaft of the balloon catheter and encircle the inner surface of the expandable balloon 303A within the at least one channel 303A.

Further, the elongated shaft of the balloon catheter includes a second inner lumen 313 in fluid communication with the expandable balloon 301, wherein another channel (not shown) or multiple channels (not shown) may be incorporated. For example, the additional channels may be used for additional optical fibers that can be incorporated within the elongated shaft of the balloon catheter and encircle the inner surface(s) of the expandable balloon 303A. It is possible that, the channel or channels may be shaped longitudinally within the expandable member, wherein there may be 1, 2, 3, 5, 8 or more longitudinal channels extending from one end to another end of the expandable member. It is possible that a longitudinal channel or channels may be inter-connected with one or more other channels, so that an optical fiber or multiple optical fibers may extend there through. The longitudinal channel may be linear, non-linear or some combination thereof extending from one end to another end of the expandable member.

In some embodiments, the channel or channels may be spiral shaped within the expandable member, wherein there may be 1, 2, 3, 5, 8 or more spiral channels. It is possible that a spiral shaped channel or channels may be inter-connected with one or more other channels, so that an optical fiber or multiple optical fibers may extend there through. The spiral shaped channel or channels may be linear, non-linear or some combination thereof. At least one aspect, by non-limiting example, among other things, is that the channel or channels can be configured to provide a maximum amount of light to the bone walls within the cavity of the bone. At least one benefit, among other things, of a spiral configuration is the large amount of light provided.

Figure 27:
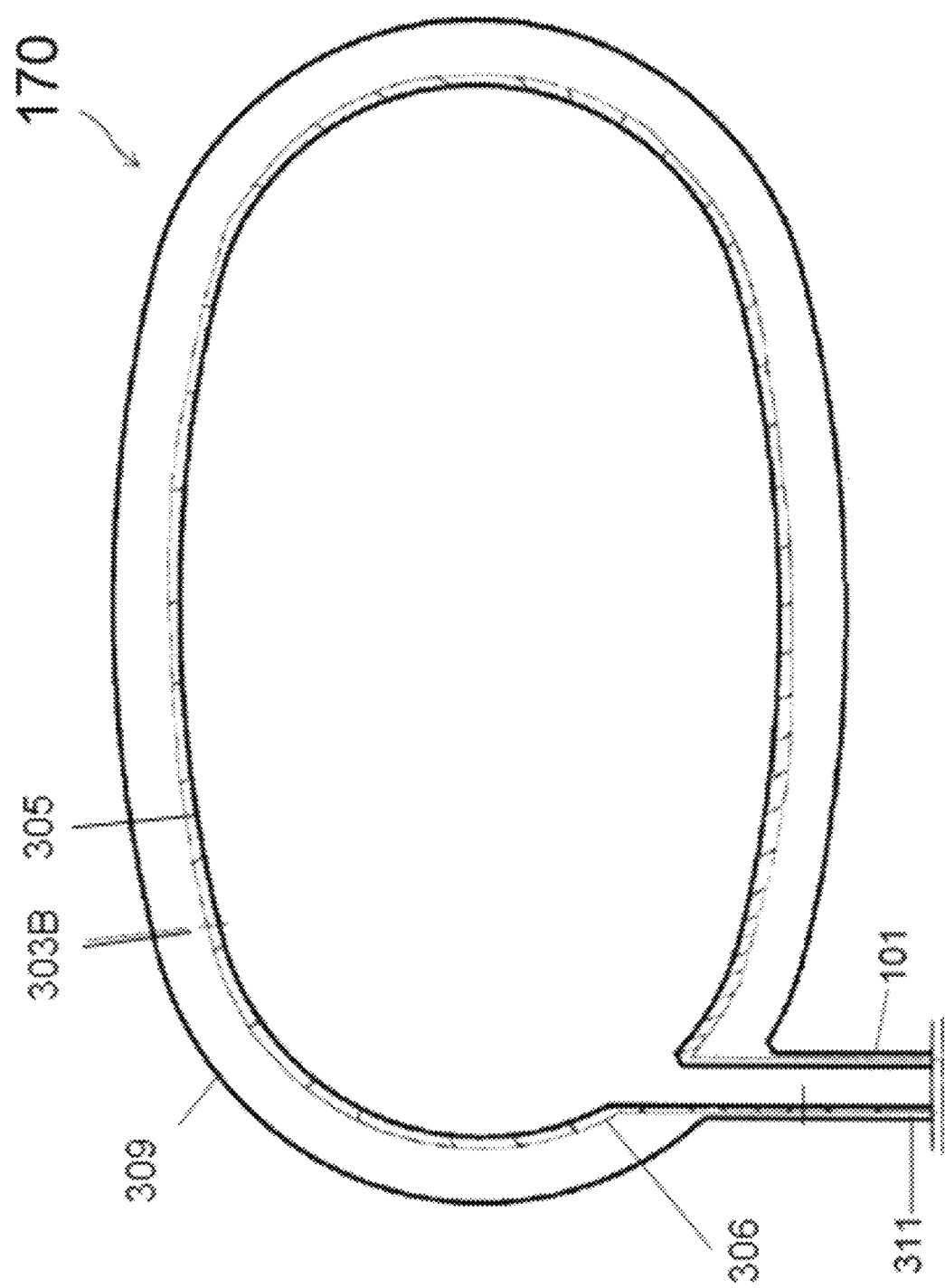

Ridges Located on an Outer Surface of Expandable Member Having at Least One Channel for the Optical Fibers FIG. 27 shows ridges 309 located on an outer surface 305 of the balloon 301 of the expandable member 170, wherein the ridges 309 include at least one channel 303B for the optical fibers 306 to enter there through. The distal end of the balloon catheter includes expandable member 170, with the inflatable balloon 301 includes an inner lumen 311 and one or more ridge 309 located the outer surface 305 of the inflatable balloon 301, wherein at least one or more channel 303B is located within the one or more ridge 309. The ridge 309 can be configured to incorporate at least one or more channel 303B for at least one or more optical fiber 306, such that the at least one or more optical fiber 306 is capable of entering and exiting the at least one or more channel 303B.

The ridge or ridges 309 may be shaped longitudinally along an outer surface of the expandable member, wherein there may be 1, 2, 3, 5, 8 or more longitudinal ridges 309 extending from one end to another end of the expandable member 170. It is possible that a longitudinal ridges 309 may be inter-connected with other ridges 309, so that an optical fiber or multiple optical fibers 306, i.e. within the channel's 303B of the ridges 309, may extend there through. The longitudinal ridges 309 may be linear, non-linear or some combination thereof extending from one end to another end of the expandable member.

The ridges or channels that are described could also be the means for the delivery of the irrigation fluids (for example, the H2O2). They also could be set in a series. For example, the even numbers of them (i.e., 2, 4, 6, 8) are the irrigation versions, and the weep holes for the fluid is at the proximal aspect, where the aspiration channels are the odd numbers channels (i.e., 1, 3, 5, 7) have small holes at the distal section of the channel to pull the materials out of the canal, thereby having the irrigation aspiration on the circumference.

In some embodiments, the ridge or ridges 309 may be spiral shaped within the expandable member 170, wherein there may be 1, 2, 3, 5, 8 or more spiral ridge or ridges 309. It is possible that a spiral shaped ridge or ridges 309 may be inter-connected with one or more other channels, so that an optical fiber or multiple optical fibers 306 may extend there through. The spiral shaped ridge or ridges 309 may be linear, non-linear or some combination thereof. At least one aspect, by non-limiting example, among other things, is that the ridge or ridges 309 can be configured to provide a maximum amount of light to the bone walls within the cavity of the bone.

The ridges that include channels are configured to provide access for passing optic fibers to pass there through and within the cavity of the bone; either prior to, during the delivery of the light-sensitive liquid, or after the light-sensitive liquid has been cured and hardened. It is contemplated the optical fiber(s) may provide for an antimicrobial effect while light-sensitive liquid is infused through the inner void 210 in the delivery catheter 101 and enters the inner cavity 295 of the expandable member 170.

Figure 28:
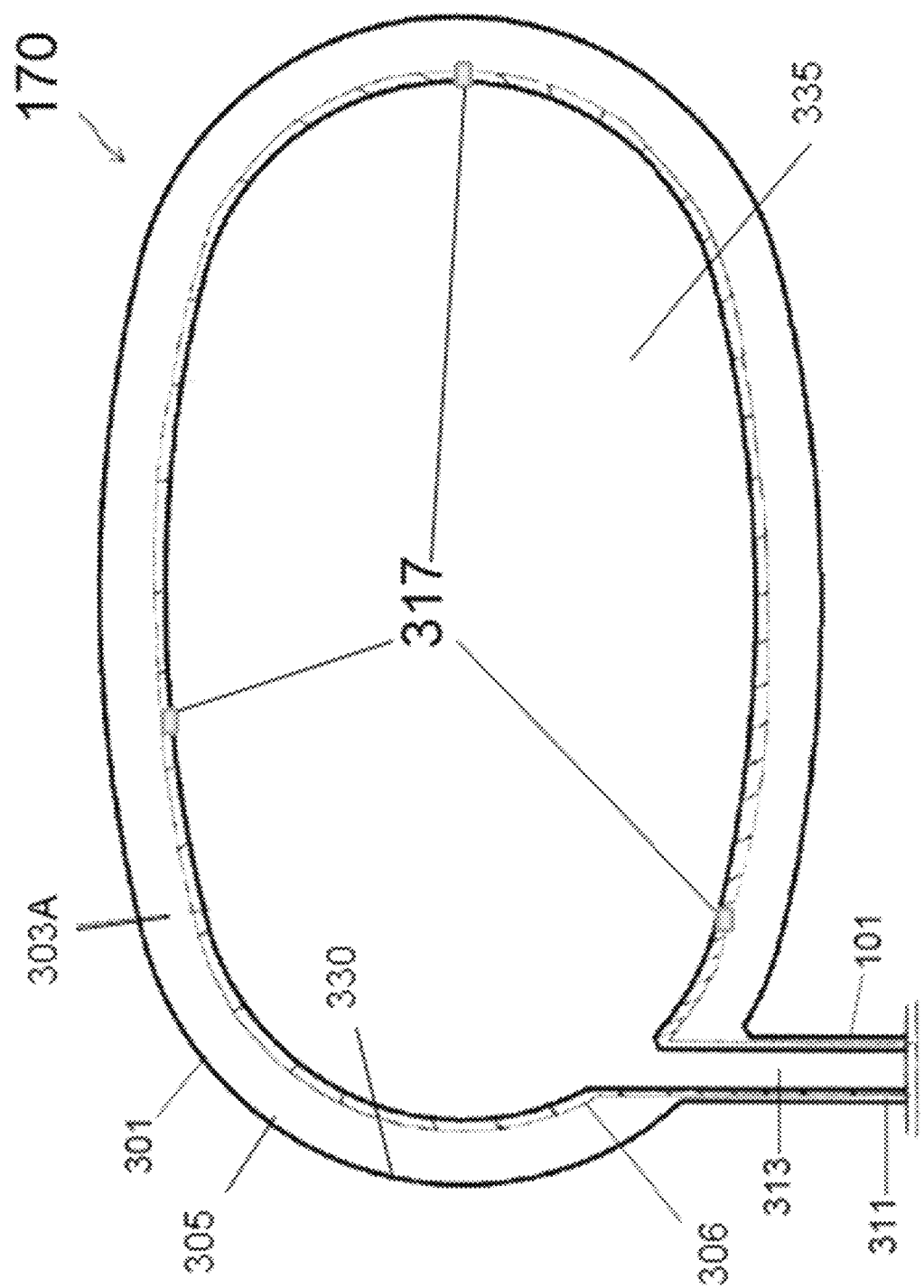
FIG. 28 shows an exemplary channel or channels configured with at least one or more reflective prisms, i.e. magnification devices, for magnifying light from the optical fibers.

Channels Having One or More Reflective Prisms, i.e. Magnification Devices, for Magnifying Light from the Optical Fibers FIG. 28 is similar to and includes the elements of FIG. 26, however, FIG. 28 shows a channel or channels 303A configured with at least one or more reflective prisms 317, i.e. magnification devices, for magnifying light from the optical fibers. The reflective prisms may include reflective prism arrays, reflective prism assemblies and the like, wherein the reflective prisms can be located along the channels 303A, 303B, and/or at an end of the channels 303A, 303B. The reflective prism can be used to reflect light, in order to flip, invert, rotate, deviate or displace the light beam from the optical fiber. For example, the reflective prism may comprise of different types of materials, including reflective tape, among other things.

Figure 29:
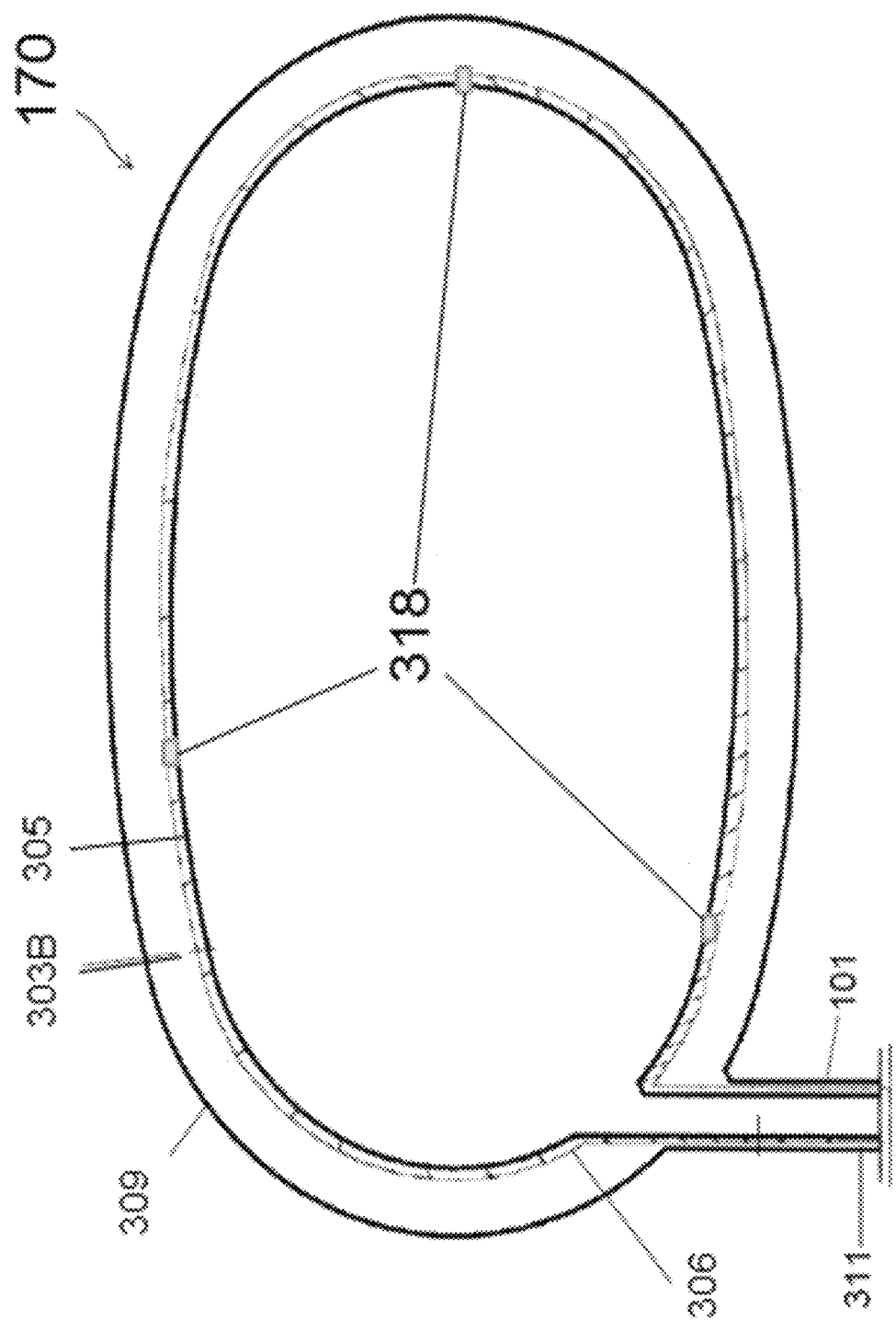
FIG. 29 shows an exemplary ridge or ridges configured to include at least one or more reflective prisms, i.e. magnification devices.

Ribs Having One or More Reflective Prisms, i.e. Magnification Devices, for Magnifying Light from the Optical Fibers FIG. 29 is similar to and includes the elements of FIG. 27, however, FIG. 29 shows a ridge or ridges 309 configured to include at least one or more reflective prisms 318, i.e. magnification devices. The reflective prisms may include reflective prism arrays, reflective prism assemblies and the like, wherein the reflective prisms can be located along the ridge or ridges 309, and/or at an end of the ridge or ridges 309. The reflective prism can be used to reflect light, in order to flip, invert, rotate, deviate or displace the light beam from the optical fiber.

Figure 30A:
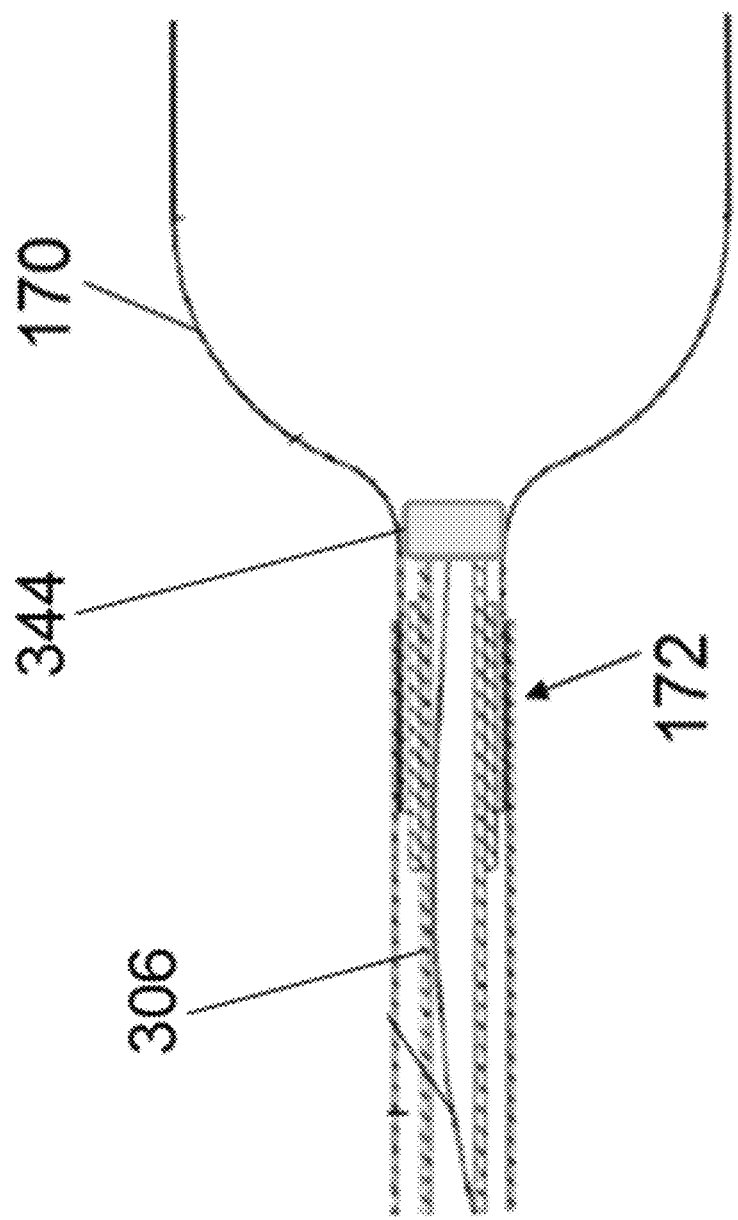
FIG. 30A shows an exemplary embodiment of a manifold located at a proximal end of the expandable member.
Figure 30B:
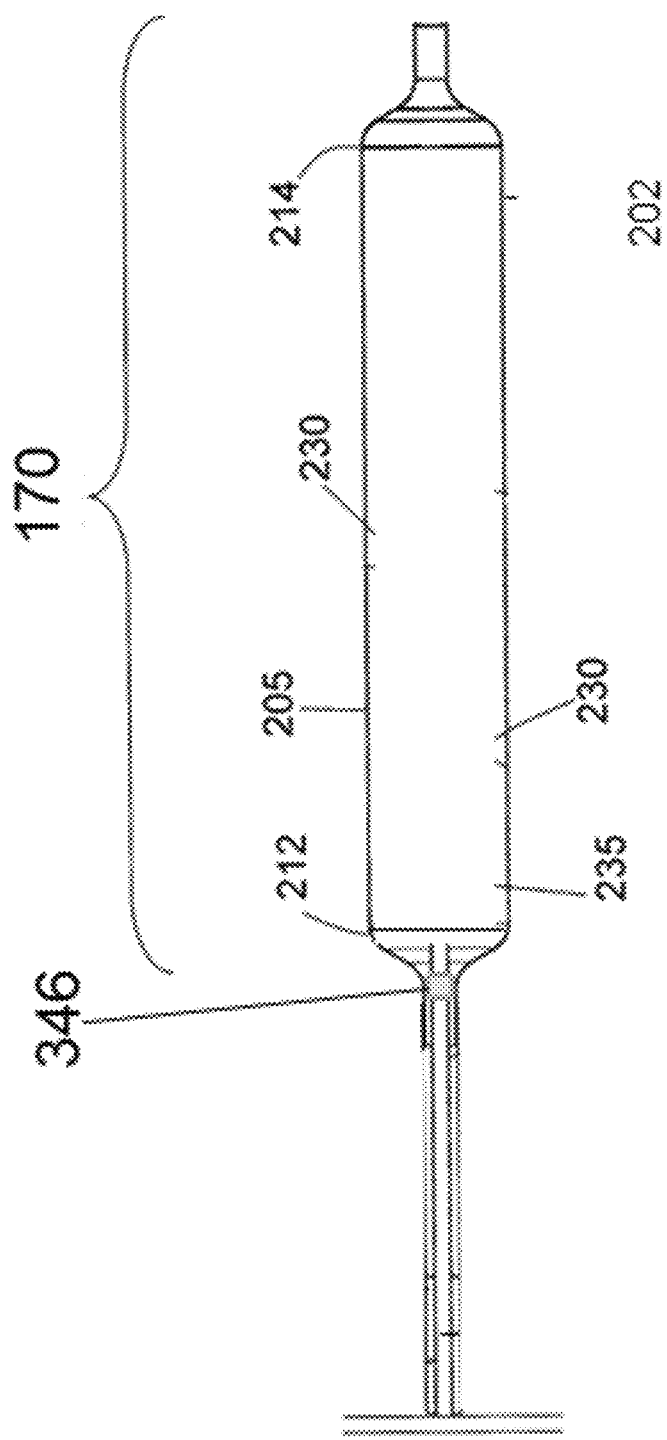
FIG. 30B shows an exemplary embodiment of a manifold located in a lumen at a distal area of the expandable member.

Manifold Incorporated within an End of Expandable Member for Allowing Access to Channels for the Optical Fibers FIG. 30A and FIG. 30B show at least one manifold 344, 346 located within at least one lumen of the expandable member 170.

FIG. 30A is similar to and includes the elements of FIG. 2C, however, FIG. 30A shows the manifold 344 in communication with the at least one lumen of the expandable member 170 and in communication with the one or more channels (not shown) located within the expandable member 170 as shown in FIG. 26. The manifold 344, by non-limiting example, can provide access for one or more light-conducting fiber 306 to enter the at least one lumen of the expandable 170 and through the manifold 344 and further into the channels located within the expandable member 170. The manifold 344 is configured to provide access for passing optic fibers 306 within the cavity of the bone; either prior to, during the delivery of the light-sensitive liquid, or after the light-sensitive liquid has been cured and hardened.

Still referring to FIG. 30A shows the manifold 344 located at a proximal end of the expandable member 170. For example, the manifold 344 may be located within a lumen of the expandable member 170 from about an end of the separation area 172 closest to the proximal end of the expandable member 170 to the proximal end of the expandable member 170 (see FIG. 2C and FIG. 2D). The manifold 344 of FIG. 30A may be utilized by first accessing the flexible balloon catheter first port with the light-conducting fiber (see FIG. 1A, FIG. 1B, and FIG. 1C), then passing the light-conducting fiber through the inner lumen (see FIG. 2A and FIG. 2B), through the a distal end of the balloon catheter and into the separation area 172 (see FIG. 2C and FIG. 2D), then into at least one lumen of the expandable member to enter into the manifold 344.

FIG. 30B shows a manifold 346 located in a lumen at a proximal area 212 of the expandable member 170. Wherein, the manifold 346 of FIG. 30B may be utilized by entry through the flexible balloon catheter, however, the manifold 346 may be utilized by the optical fiber entering the distal end 214 of the expandable member 170.

Regarding FIG. 30A and FIG. 30B, the manifold 344, 346 may comprise of a flexible material, a non-flexible material or some combination thereof. The manifold 344, 346 may comprise of two or more openings that connect with two or more channels located within the expandable member.

Removable Cap to Seal Lumens of Expandable Member

Figure 31A:
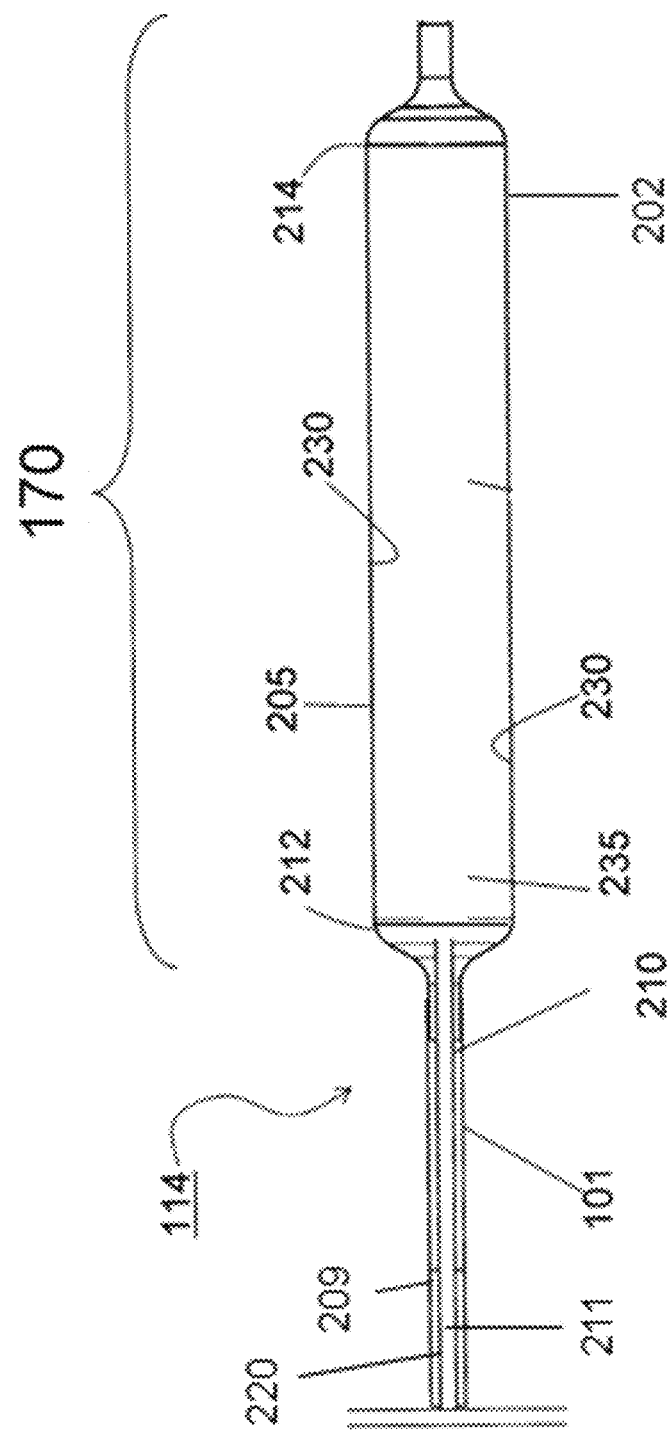
FIG. 31A, FIG. 31B and FIG. 31C show views of a distal end of a device having a removable cap for repairing a weakened or fractured bone of the present disclosure, according to embodiments of the disclosure.
Figure 31B:
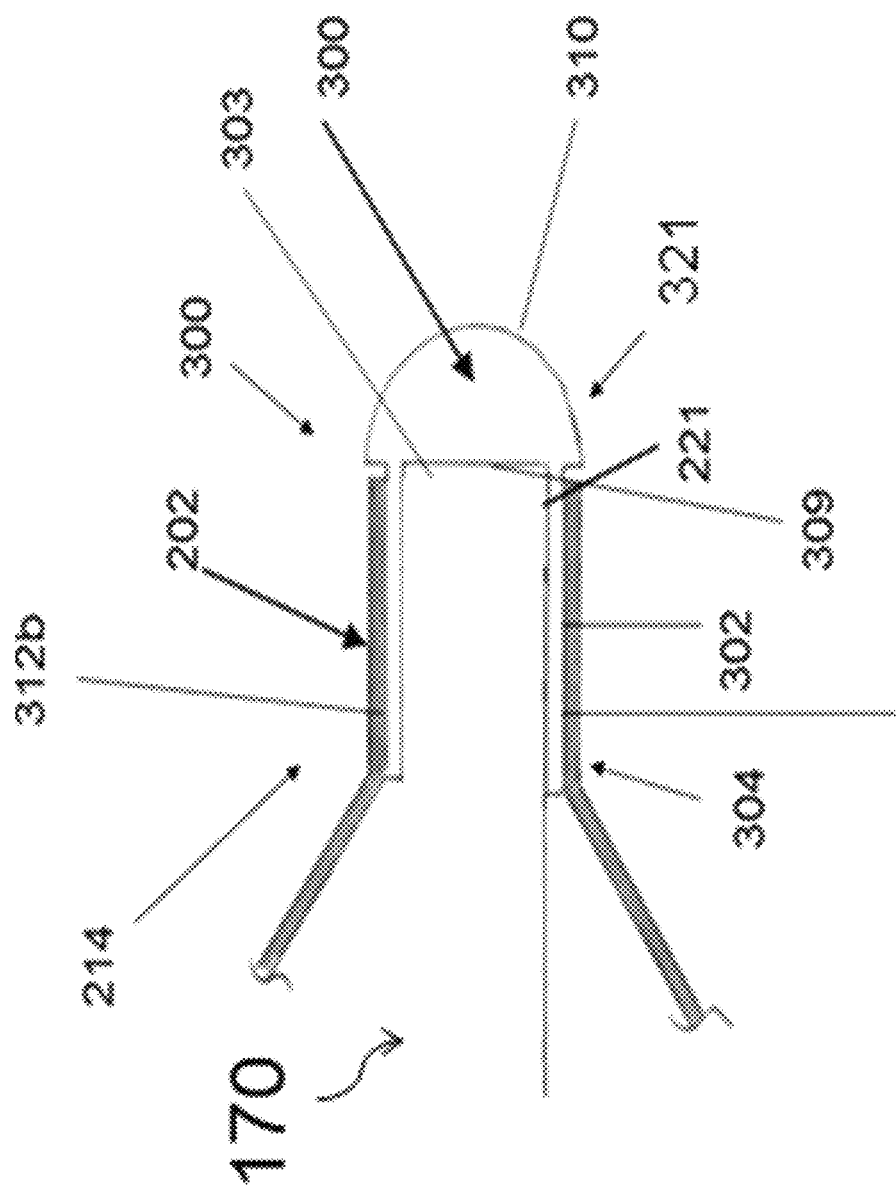
Figure 31C:
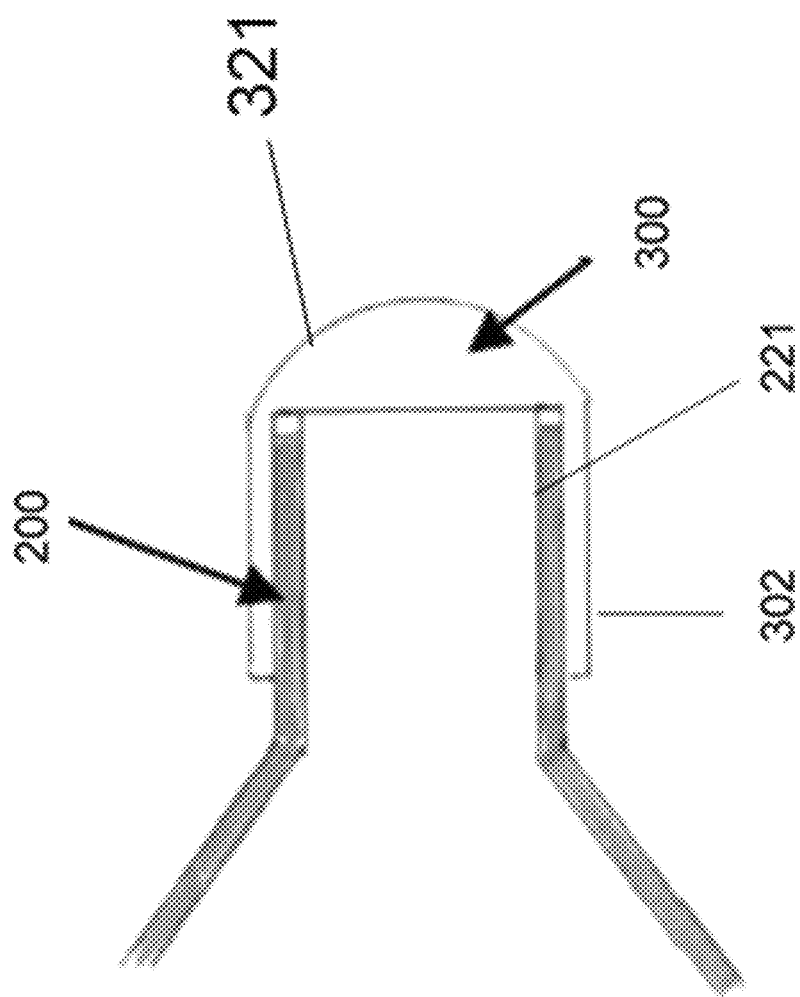

FIG. 31A, FIG. 31B and FIG. 31C show views of a distal end of a device having a removable cap for repairing a weakened or fractured bone of the present disclosure.

It is contemplated the removable cap may be used after the light sensitive liquid has been cured, wherein the hardened expandable member is formed into a formed photodynamic implant. For example, it is possible the formed photodynamic implant may have a removable cap that seals the lumen from fluids and/or other tissue from entering, thus keeping the lumen clean, as well as the light intensity in the future is not diminished. It is possible the central lumen may include a receptacle for at least one rod that may be used to fill the lumen, such that screws on the end of the implant may be designed and/or intended to keep the lumen clean and optically transparent. Further, lumen can be accessed in the future by a removal of the cap, and the rod or the cap may have a valve or access point to allow a minimally invasive means to post operatively introduce the light source. Further still, the cap may have a valve and/or access port that can be accessed in a minimally invasive fashion. It is possible that a small percutaneous needle may be used, where the fiber is introduced through the cap, and/or the fiber may lead in to it. The cap and implant end can be designed to guide and steer the fiber into the lumen. It is possible that there may be a conical end that acts as a recipient. Further, the cap can be of a radiopaque material that it can be located by x-ray.

FIG. 31A is a view of an embodiment of a distal end 114 of the flexible delivery catheter 101. The distal end 114 includes the expandable member 170 releasably mounted on the flexible delivery catheter 101. The expandable member 170 has a wall 202 with an outer surface 205 and an inner surface 230. The inner surface 230 defines an inner cavity 235. In some embodiments, the delivery catheter 101 may include multiple inner lumens or voids. For example, as shown in FIG. 31A, the delivery catheter 101 may include an outer tube 209 and a central tube 220 concentrically disposed within the delivery catheter 101. An inner void 210 may be formed between the outer tube 209 and the central tube 220. The inner void 210 may be utilized for passing a light-sensitive liquid into the inner cavity 235 of the expandable member 170. In some embodiments, the central tube 220 includes an inner lumen 211 for passing a light-conducting fiber (which is not illustrated in FIG. 2) into the expandable member 170 to cure the light sensitive liquid inside the inner cavity 235 of the expandable member, as described in detail below. It should be noted that while the delivery catheter 101 is described as having the central lumen 220 concentric with the outer tube 209, the central lumen 220 may be off-set relative to the outer tube 209.

The expandable member 170 includes a proximal area 212 and a distal area 214. The proximal area 212 of the expandable member 170 is releasably connected to the delivery catheter 101. The distal area 214 may be connected to the delivery catheter 101 in a variety of ways.

In reference to FIG. 31B, in some embodiments, the distal area 214 of the expandable member 170 may be connected to a distal cap 300. The distal cap 300 terminates and seals off the area 214 (or lumen) of the expandable member 170 to prevent the flow of a light-sensitive liquid outside the balloon and the ingress of bodily fluids inside the balloon. One potential benefit of utilizing the distal cap 300 is case of manufacture and more consistent tip quality when compared to traditional melt forming of expandable member 170 directly to the delivery catheter. An additional benefit of the use of the distal cap 300 may also include the ability to reflect back or scatter light radiating from the end of the conducting fiber to improve the light-sensitive liquid cure times or depth of cure. The reflected light from the distal cap 300 may increase the energy that is directed towards the light-sensitive liquid in the expandable member 170 and thus may increase the photo-initiation rate (and thus polymerization rate) of the light-sensitive liquid.

In some embodiments, the distal cap 300 may be formed, molded or machined from an implant grade polymer (e.g., PET), or another biocompatible material. The distal cap 300 may also be made from a filled material. For example, the PET polymer may be blended with a radiopaque material (e.g., barium sulfate, tungsten, tantalum, etc.) such that the distal cap 300 may be viewed with the assistance of fluoroscopic imaging. In some embodiments, the distal cap 300 may also be covered with a reflective material such as a gold film (or other metallic highly polished implant grade film) to enable the distal cap 300 to reflect light radiating from the end of the light pipe back into the balloon. This reflected light can help to reduce the cure time of the light sensitive liquid contained within the expandable member 170 to due to the increase in light energy directed at the light sensitive liquid. In some embodiments, the distal cap 300 may also be fabricated from a crystalline material (such as crystalline PET) to block the transmission of light through the end of the device 100 and to reflect and/or scatter the light back to the light sensitive liquid in the expandable member 170.

As illustrated in FIG. 31B, a distal cap 300 includes a body 302 having a proximal end 304 and a distal end 321. The body 302 defines an inner compartment 303 wherein at least one manifold (not shown) may optionally be positioned. The distal cap 300 may stabilize the at least one manifold and may minimize movement of the at least one manifold during the operation. It is possible the at least one manifold may be secured inside the compartment 303 by press fitting the at least one manifold into the compartment 303; applying permanent adhesive on the surfaces between the at least one manifold and the compartment 303; melt bonding the two surfaces together or other techniques.

FIG. 31B and FIG. 31C show the distal end 321 of the body 302 may be either open or closed. In some embodiments, the distal cap 300 closes the distal tip 321 of the body 302 to close the distal tip 321. The distal cap 300 includes an inner surface 309, which faces the body 302, and an outer surface 310, which faces away from the body 302. In some embodiments, the outer surface 310 of the distal cap 300 may be rounded or smooth to provide the device 100 with an atraumatic distal point. In some embodiments, the distal cap 300 may have a semi-circular shape with a flat inner surface and a curved outer surface.

In reference to FIG. 31B, in some embodiments, the material forming the expandable member 170 may be attached to the outer surface of the body 302. In some embodiments, the outer surface of the body 302 includes recessed attachment sections 312a, 312b to which the material of the expandable member 170 can be attached. In some embodiments, the outer surface of the body 302 may be recessed by a depth approximately equal to the thickness of the expandable member material. In this manner, when the expandable member material is attached to the body 302, the outside of the expandable member material is substantially aligned with the outer surface 310 of the distal cap 300. The material of the expandable member 170 can be attached to the body 302 by a variety of methods, including, without limitation, adhesives such as cyano-acrylates or epoxies, crimping metallic rings over the expandable potion, melt bonding the expandable member to the body 302 with the use of heat (e.g., RF generated), ultrasonically welding the expandable member to the body 302, or another method or combination of methods.

In reference to FIG. 31C, in some embodiments, the material of the expandable member 170 may be attached to the inner surface of the body 302 of the distal cap 300.

Optic Fibers

The light conducting fibers or optical fibers may include a single optical fiber or a plurality of light conducting fibers 140, wherein the optical fibers may be positioned side-by-side or in parallel in the expandable member 170 (see FIG. 1B and FIG. 1C). In some embodiments, a plurality of light conducting fibers 140 can be positioned serially with ends of adjacent light conducting fibers 140 aligned or abutting on another in an end to end fashion (see FIG. 1B and FIG. 1C). For example, one light conducting fiber may be positioned in the distal portion of the expandable member and another light conducting fiber may be positioned in the proximal portion of the expandable member 170. In some embodiments, a plurality of light conducting fibers can be positioned in a combination of parallel and serial positions, such as partially overlapping or any other suitable configuration. In some embodiments, a plurality of light conducting fibers can be attached to a single light source with a splitter, or can be attached to a plurality of light sources.

The most basic function of a fiber is to guide light, i.e., to keep light concentrated over longer propagation distances despite the natural tendency of light beams to diverge, and possibly even under conditions of strong bending. In the simple case of a step-index fiber, this guidance is achieved by creating a region with increased refractive index around the fiber axis, called the fiber core, which is surrounded by the cladding. The cladding may be protected with a polymer coating. Light is kept in the "core" of the light-conducting fiber by total internal reflection. Cladding keeps light traveling down the length of the fiber to a destination. In some instances, it is desirable to conduct electromagnetic waves along a single guide and extract light along a given length of the guide's distal end rather than only at the guide's terminating face.

In some embodiments, an optical fiber of the present disclosure is manufactured from a Lumenyte STA-FLEX® "SEL" END LIGHT OPTICAL FIBER, available from Lumenyte International Corporation of Foothill Ranch, CA, can be employed. These optical fibers may each consist of a light transmitting solid large core, a Teflon® clad and a black bondable outer jacket. The optical fiber may transmit light from a light source to the distal tip for use as a point source. The optical fiber may have a wide 80 degree acceptance angle and 80 degree beam spread, allowing the light to be viewed from more oblique angles. The light transmitting core may be solid, may have no light diminishing packing fraction losses and may be easily spliced. The jacket may be bondable. Custom jackets may be available for more flexibility and color options. The optical fiber can each have a transmission loss (attenuation) of less than approximately 1.5% per foot, a bend radius (minimum) of approximately 6 times the fiber's diameter, temperature stability of up to approximately 90° C. (194° F.), spectral transmission range of approximately 350-800 nm, an acceptance angle of approximately 80°, a refractive index core of approximately 1.48 or greater, cladding of approximately 1.34 or less and a numerical aperture of approximately 0.63. The length of the optical fiber can be approximately 100 continuous feet. Splicing may be achieved in the field using a splice kit, such as the Lumenyte Splice Kit, and carefully following the instructions. Factory splicing may be an option. An optic cutter, such as Lumenyte's Optic Cutter, may be advised for straight, clean, 90° fiber cuts. These fibers may be installed by removing approximately 4 inches (10 cm) of the outer jacket (not the fluoropolymer cladding) before inserting fiber into the light source. An end of the fiber may be near, but not touching the illuminator (light source) glass to assist in achieving maximum brightness.

In some embodiments, an optical fiber of the present disclosure is manufactured from a ESKA™ High-performance Plastic Optical Fiber: SK-10 and SK-60 and/or ESKA™ Plastic Fiber Optic & Cable Wiring, manufactured by Mitsubishi Rayon Co., Ltd., which are all available from Mitsubishi International Corporation of New York, NY. These optical fibers may each consist of a light transmitting PMMA (polymethylmethacrylate) core and a fluorinated polymer as the cladding. It should be appreciated that the above-described characteristics and properties of the optical fibers are exemplary and not all embodiments of the present disclosure are intended to be limited in these respects.

In some embodiments, optical elements may be oriented in alignment with the notches, cuts or openings in the nonlinear light-emitting portion of an optical fiber of the present disclosure to adjust the light output. Such optical elements may include lenses, prisms, filters, splitters, diffusers and/or holographic films. The light source, and more specifically, the optical fibers may have some or all of the properties and features listed in U.S. Pat. No. 6,289,150, which is hereby incorporated by reference in its entirety, as not all embodiments of the present disclosure are intended to be limited in these respects.

One or more optical elements, such as diffusers, polarizers, magnifying lenses, prisms, holograms or any other element capable of modifying the direction, quantity or quality of the illumination, individually or in combination can also be added and aligned with the core-clad, notches and channel, track or holder and/or reflector.

Further, the implant may be designed to amplify light to the surrounding areas using one of reflective prisms within, Fresnel lens, Magnification lens on the surface, shapes to the external form of the implant that are designed to magnify/amplify the light transmission.

The efficiency of plastic optical fiber is well known, with the losses of light transmitted down the fiber almost nil. However, in the example of the fiber with the circumferential radial cuts on the fiber, there is still a significant amount of light that is transmitted down the fiber and exits out the distal tip. This light is lost to the system, as it is end fire (a flashlight) versus the side fire (radial system described herein). To maximize the efficiency of the system, a reflective fitting/surface can be placed on the distal end of the fiber to reflect the "end fire" energy back up and out of the side cuts of the fiber. The use of the reflective end cap results in approximately 7% increased power/efficiency of the system. The reflective material on the distal end of the fiber can vary, and can be in the form of a mirror, white or light colored pigment, or other reflective surfaces. The loss in the system is decrease as the light emitted from the distal end of the fiber is reflected back into the fiber.

The surface of the reflector can be mirrored, or it can be an optical white reflective surface. For example, labsphere's 6080 White Reflectance Coating is a diffuse white coating "paint" for reflectance applications covering the UV-VIS-NIR wavelength region. This coating is intended for customers with small-scale applications, those that require a touchup to their original application, or those who wish to prototype components using a high-reflectance white coating. This non-luminescent coating yields reflectance values of 95 to 98% over the wavelength region from 300 to 1200 nm.

The 6080 is ideal for use in integrating spheres, reflectance spectrophotometers, sphere photometers, lamp housings, display backlight reflectors, optical components and other applications that call for diffuse illumination or reflectance. This coating also allows Labsphere Spectraflect® and Duraflect® coated integrating sphere systems to be touched up in-between system recalibrations and re-coatings.

The 6080 coating is created in Labsphere's dedicated coating laboratory using the highest ISO-9001:2000 procedures and requires no additional dilution or mixing. The coating is packaged in airtight, containers and is shipped with surface preparation and application instructions.

Exemplary properties and performance of the system is reflected in the tables below. Reflectance is the percentage of light that is bounced back from the mirror. Spectral range relates to the ability to handle wavelengths/ranges of NM frequencies. Thermal stability relates to maximum temperature the system can handle. Laser damage relates to the amount of power the system can handle.

| | |
|---|---|
| Reflectance: | 95-98% (see chart below) |
| Effective Spectral Range: | 300 to 1200 nm |
| Thermal Stability: | to 80° C. |
| Laser Damage Threshold: | 0.9 J cm$^{-2}$ |

| (nm) | % |
|---|---|
| 400 | 0.970 |
| 500 | 0.975 |

Figure 32:
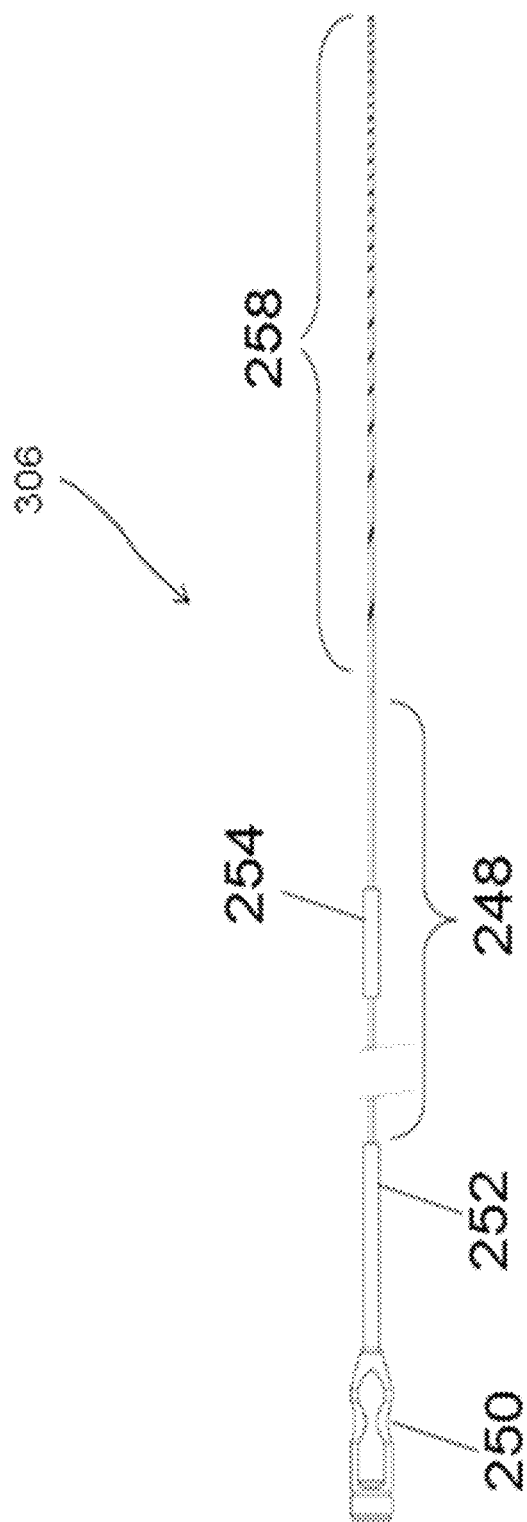
FIG. 32 shows an embodiment of an optical fiber of the present disclosure fabricated from a flexible light transmitting material that can be inserted into at least one channel, according to embodiments of the disclosure.

Customized Cuts Along Optical Fiber to Align with Channel Configurations to Maximize Light Amplification FIG. 32 shows an embodiment of an optical fiber 306 of the present disclosure fabricated from a flexible light transmitting material that can be inserted into at least one channel. The optical fiber 306 includes a hub 250 at a proximal end for attaching to a light source (either directly or indirectly, for example, through the use of an attachment system, see FIG. 1). The optical fiber 306 includes a linear elongated portion 248 for guiding light towards a nonlinear light-emitting portion, generally referred to as 258, which emits light from the outside of the fiber along its length. The nonlinear light-emitting portion 258 can be any length suitable for a given application. The distal tip of the optical fiber 306 may also emit light creating a small spotlight effect. In some embodiments, the optical fiber 306 also includes a flexible strain relief 252 just to the right of the hub 250 and a depth stop 254. In some embodiments, the strain relief 252 prevents snapping of the optical fiber 306 at the hub 250 junction. In some embodiments, the strain relief 252 and the depth stop 254 are made from a flexible material. In some embodiments, the strain relief 252 and the depth stop 254 are made from Santoprene™, a thermoplastic rubber.

FIG. 32 shows the optical fiber 306 in an elongated stretched condition and being in a "temporary" shape. In the temporary shape, the nonlinear light-emitting portion 258 is stretched and assumes a linear conformation in which the nonlinear light-emitting portion 258 of the optical fiber 306 can be advanced through the inner lumen of the elongated shaft of the balloon catheter 110.

Measurement has shown that a portion of light still emits from the distal tip irrespective of the effect of the cladding being removed over a length of the fiber. The shorter the active length (i.e., the more percentage of light is tip emitted), and the longer the active length less light is emitted. The ratios are approximately in the range of 5% to 20% of light delivered in a non-productive direction. In some embodiments, a plane or reflective tip on the end of the fiber can be used to resolve the loss and improve the efficiency. These mirrors can be either front face or rear faced mirrors and can be a concave mirror. The result is that the light that is emanating out of the tip is reflected back into the fiber and increasing the efficiency of the system.

As illustrated in FIG. 32, for example, according to some embodiments, a helical design may be provided that includes cuts at a most proximal portion of the light-emitting portion that are spread farther apart than cuts at a most distal portion of the light-emitting portion. Typically, when an optical fiber is attached to a light source that is "on", the cuts at the proximal portion of the light-emitting portion will emit light that looks brighter than the cuts at the distal portion of the light-emitting portion when in at least one channel.

The optical fiber may include a non-shape memory optical fiber or a shape memory optical fiber depending on the application relating to one or more channels or not relating to one or more channels located within or on the outer surface (i.e. within ridges) of the expandable member. For example, it may be desirable to provide shape memory to the light-emitting portion of an optical fiber of the present disclosure so as to conform to a shape of at least one channel. In some embodiments, the shape memory can be imparted to the light-emitting portion using conventional techniques known in the art. By way of a non-limiting example, a distal length of an optical fiber of the present disclosure may first be heat treated to provide stress relief, that is, to remove any shape memory from the optical fiber induced into the optical fiber during the manufacturing process. Heat treatment can also be used to induce a pre-set into the optical fiber. The distal length of the stress-relieved optical fiber may then be wound around a circular mandrel to provide the distal length with a desired shape. Next, the mandrel with the coiled optical fiber can be subjected to heat treatment to induce the desired shape and then quenched to set the desired shape into the optical fiber. In an embodiment, the optical fiber may be heat treated using a water bath.

Figure 33:
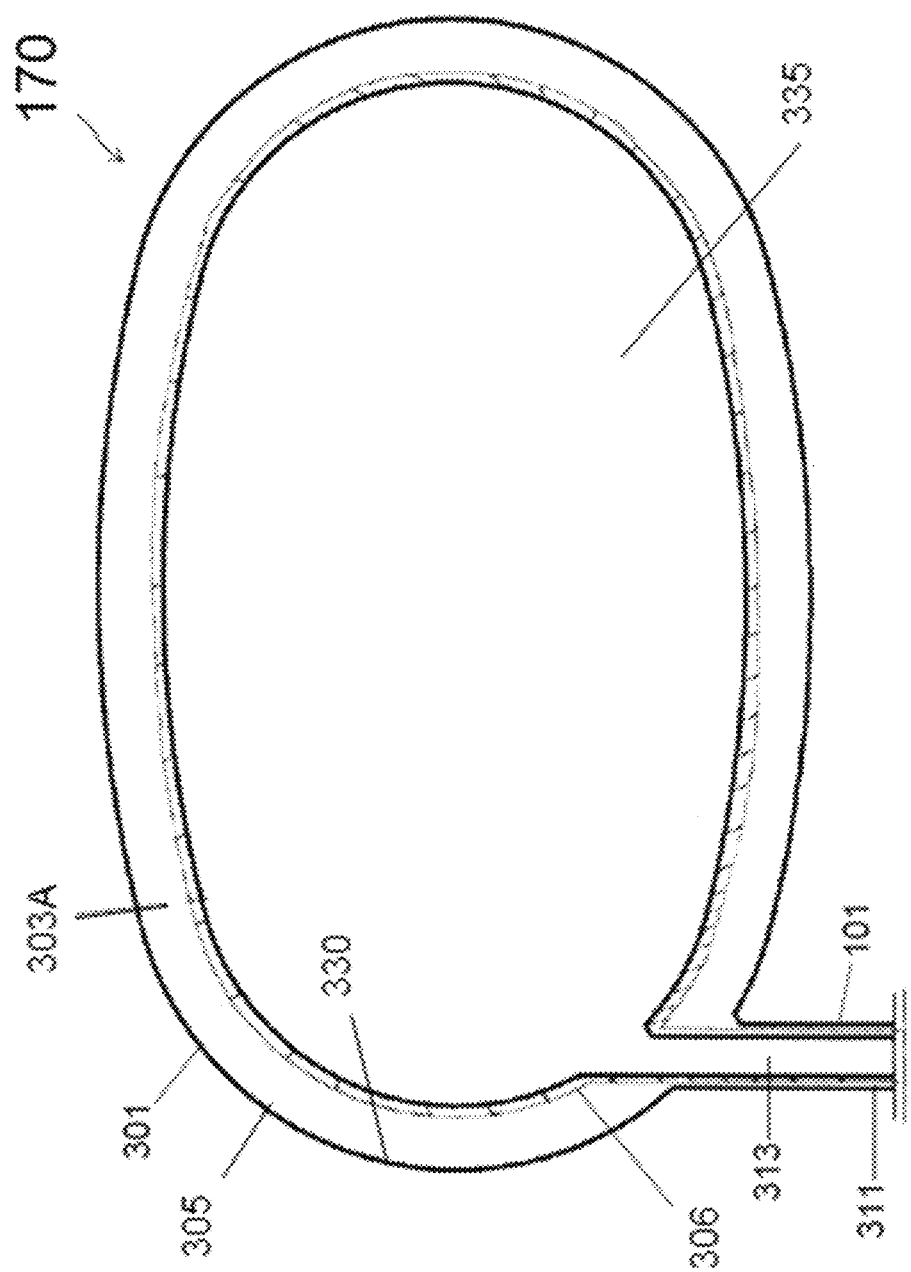
FIG. 33 shows a view of another embodiment of a distal end of a balloon catheter of the present disclosure, which is similar to FIG. 26, wherein the optical fiber has a pre-defined shape specific to the shape of the channel.

FIG. 33 shows a view of another embodiment of a distal end of a balloon catheter of the present disclosure, which is similar to FIG. 26, wherein the optical fiber 306 has a pre-defined shape specific to the shape of the channel 303A. Wherein the optical fiber 306 can be incorporated within the elongated shaft of the balloon catheter and encircle the inner surface 330 of the expandable balloon 303A within channel 303A.

The nonlinear light-emitting portion can be any given length suitable for a given application. For example, a nonlinear light-emitting portion of an optical fiber of the present disclosure can have a length ranging from about 60 mm to about 300 mm, 60 mm to about 400 mm, 60 mm to about 500 mm or 60 mm to about 600 mm. It is contemplated the optical fiber may be shaped to incorporate a single loop to extend an entire length of the channel 303A or only partially extend the entire length of the channel 303A.

It is possible illuminators may be made in the optical fiber core alone before the cladding is added and/or the illuminators may be made in the cladding and the core after it has been surrounded by the cladding. In some embodiments, when the cladding is heated to tightly shrink around the core, the cladding may affect the uniformity of the illuminators in the core by either entering the notch or closing the cut thereby reducing the potential light deflecting properties of the illuminator.

The illuminators may be positioned to direct light across the greater diameter of an elliptical optical fiber core out and out through a region opposite from each of the respective illuminators. This may be accomplished by angling the notches and/or cuts to direct light from the light source through the optic core. The illuminators allow better control of escaping light by making the notches, which are positioned on one side of the optic to direct the light rather than allowing the cuts to reflect/refract light in various directions which reduces the contribution of light to a desired focusing effect.

In an embodiment, the total light output from a nonlinear light-emitting portion of the present disclosure having a length of about 100 mm is the same as a nonlinear light-emitting portion of the present disclosure having a length of about 300 mm. In an embodiment, the total light output required for the nonlinear light-emitting portion of an optical fiber of the present disclosure is about 10 $\mu W/cm^2$, 20 $\mu W/cm^2$, 30 $W/cm^2$, 40 $\mu W/cm^2$, 50 $\mu W/cm^2$ or 60 $\mu W/cm^2$.

In some embodiments, the optical fiber may include an optical fiber core surrounded by cladding material and one or more illuminators. The illuminators may be of uniform size and shape positioned in a predetermined, spaced-apart relation, linearly, along a side of the optical fiber core. The optical fiber core may be received in a track and/or holder and/or reflector comprising a channel constructed with a reflective interior surface centered about the illuminators. The holder and/or reflector may be positioned adjacent to or in contact with the plurality of illuminators.

Irrigation

In some embodiments, the system can include mechanism for providing irrigation to the treatment site. In some embodiments, hydrogen peroxide can be used in conjunction with the light so that enhanced kill is performed. The concentration of the H2O2 may vary, and in some embodiments can be of a 3-9% concentration. The system can include the ability to provide irrigation to the canal of H2O2 during the illumination of light. The system can also include the ability to provide irrigation to the canal after the illumination of light to the cells so that the H2O2 is able to permeate the cell in their weakened state. In some embodiments, the balloon has a ridge on it at the lower point so that the H2O2 that is infused is held in a surrounding column of fluid around the balloon and that the fluid doesn't fall below the illumination point. The lower aspect of the balloon can include an aspiration port where the top if the balloon has an irrigation/infusion port. The combination of the two allows for the continual drip of fluids during the illumination procedure to ensure that the fibers and the light emitted do not become occluded by blood or other intramedullary materials. The fluid, such as H2O2, can be delivered near or adjacent to the blue light so that the two functions are combined and enhanced.

Figure 34C:
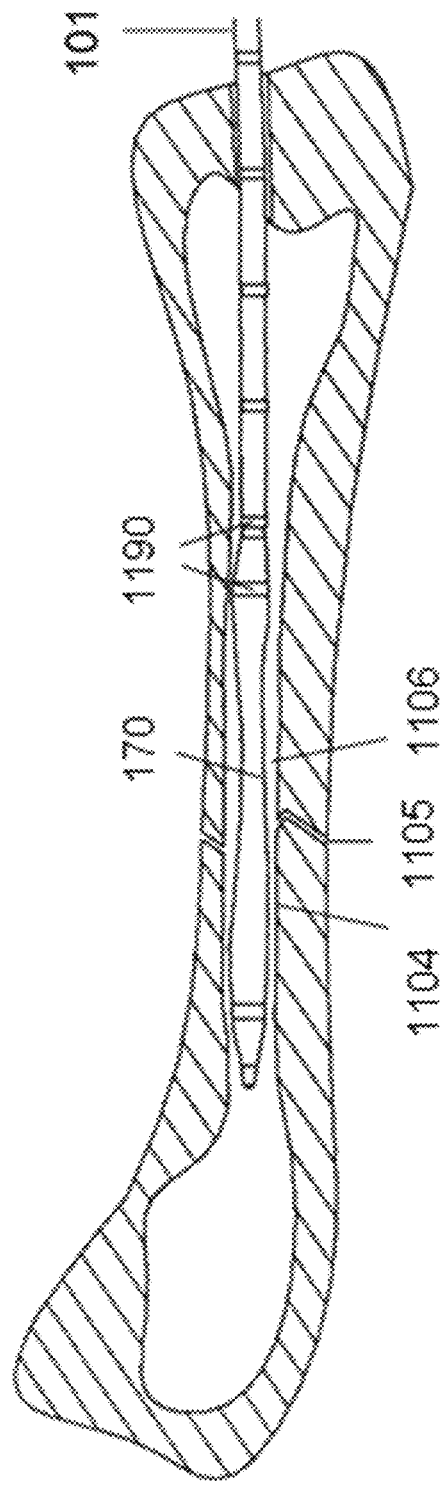

Methods of Delivering Light to Cavities of the Bone to Provide an Anti-Microbial Effect FIG. 34A, FIG. 34B, FIG. 34C, FIG. 34D and FIG. 34E provide embodiment methods for delivering light and/or implanting an intramedullary implant of the present disclosure within the intramedullary space of a weakened or fractured bone. A minimally invasive incision (not shown) may be made through the skin of the patient's body to expose a fractured bone 1102. The incision may be made at the proximal end or the distal end of the fractured bone 1102 to expose the bone surface. Once the bone 1102 is exposed, it may be necessary to retract some muscles and tissues that may be in view of the bone 1102. As shown in FIG. 34A, an access hole 1110 may be formed in the bone by drilling or other methods known in the art. In some embodiments, the access hole 1110 has a diameter of about 4 mm to about 7 mm. In some embodiments, the access hole 1110 has a diameter of about 9 mm.

The access hole 1110 extends through a hard compact (cortical) outer layer 1120 of the bone into the relatively porous inner or cancellous tissue 1125. For bones with marrow, the medullary material should be cleared from the medullary cavity prior to insertion of the presently disclosed device. Marrow is found mainly in the flat bones such as hip bone, breastbone, skull, ribs, vertebrae and shoulder blades, and in the cancellous material at the proximal ends of the long bones like the femur and humerus. Once the medullary cavity is reached, the medullary material including air, blood, fluids, fat, marrow, tissue and bone debris should be cleared or loosened to form a void. The void is defined as a hollowed out space, wherein a first position defines the most distal edge of the void with relation to the penetration point on the bone, and a second position defines the most proximal edge of the void with relation to the penetration site on the bone. The bone may be hollowed out sufficiently to have the medullary material of the medullary cavity up to the cortical bone removed. There are many methods for removing the medullary material that are known in the art and within the spirit and scope on the presently disclosed embodiments. Methods include those described in U.S. Pat. No. 4,294,251 entitled "Method of Suction Lavage," U.S. Pat. No. 5,554,111 entitled "Bone Cleaning and Drying system," U.S. Pat. No. 5,707,974 entitled "Apparatus for Preparing the Medullary Cavity," U.S. Pat. No. 6,478,751 entitled "Bone Marrow Aspiration Needle," and U.S. Pat. No. 6,958,252 entitled "Apparatus for Extracting Bone Marrow."

A guidewire (not shown) may be introduced into the bone 1102 via the access hole 1110 and placed between bone fragments 1104 and 1106 of the bone 1102 to cross the location of a fracture 1105. The guidewire may be delivered into the lumen of the bone 1102 and may cross the location of the break 905 so that the guidewire spans multiple sections of bone fragments. As shown in FIG. 34B, the expandable member 170 of the delivery catheter 101 for repairing a fractured bone, which is constructed and arranged to accommodate the guidewire, is delivered over the guidewire to the site of the fracture 1105 and spans the bone fragments 1104 and 1106 of the bone 1102. In some embodiments, the guidewire can be used to delivery additional instruments down the canal.

In some embodiments, it is contemplated that at least one optical fiber or other light source may be introduced into the bone for a period of time prior to placing the expandable member 170 within the cavity of the bone to provide for an anti-microbial effect. That is, in some embodiments, the bone 1102, the cavity 1110, and/or the surrounding tissue can be pre-illuminated to substantially sterilize the repair site prior to introduction of the expandable member. In some embodiments, because the pre-illumination light source does not need to pass through the balloon catheter 110, the pre-illumination light source can be a larger, higher-powered light source than the in-process light source for greater initial anti-microbial effect.

In some embodiments, the guidewire can be placed by use of a split sheath and dilator (not shown). In some embodiments, the split sheath and dilator can include an outer tube-shaped sheath and an inner dilator extending coaxially through the sheath. In some embodiments, the inner dilator can include a passageway sized and shaped for passing the guidewire therethrough. In some embodiments, the guidewire, the sheath, and/or the dilator can include at least one optical fiber or other light source for illuminating the repair site. In some embodiments, the sheath, the dilator, and/or the guidewire can thereby be used to pre-illuminate the repair site, illuminate the repair site during installation of the expandable member 170, and/or to illuminate the repair site during curing and hardening of the expandable member 170. Thus, by providing light source integrated within the sheath, dilator, and/or guidewire, a duration of the illumination of the repair site can be increased, thereby improving the anti-microbial effect.

Once the expandable member 170 is in place, the guidewire may be removed. The location of the expandable member 170 may be determined using at least one radiopaque marker 1190 which is detectable from the outside or the inside of the bone 1102. Once the expandable member 170 is in the correct position within the fractured bone 1102, a delivery system which contains optical fiber(s) passes light from a light source through the first port 162, through the inner lumen of the elongated shaft of the balloon catheter 110, through the distal end 104 of the balloon catheter 110, through the inner lumen of the expandable member and into the cavity of the bone. It is contemplated the optical fiber(s) may pass through a channel located within the expandable member. It is also possible the optical fiber(s) may pass through a manifold located in the inner lumen of the expandable member and then into a channel located within the expandable member. It is possible for the optical fiber(s) to enter a channel located within a ridge positioned on an outer surface of the expandable member.

It is possible for radiopaque markers and guides to provide alignment towards steering the user towards a correct position. Further, the end of the implant may have a longer inner tube and light guide receptacle that is longer than the implant and extends several inches beyond. Further still, this end could be left attached to the implant and buried subcutaneously and sealed, so that when and, if needed, the end was exposed via a small incision, the rolled tube exposed and the light fiber introduced would all make for the delivery to be easier.

As the fibers are radiolucent, it would be difficult to know the placement of the fibers or to visualize the fibers, so the radiopaque markers on the distal tip of the fiber and/or the proximal end of the fiber, can be used to ensure that the fibers are placed appropriately within the canal.

Once the optical fiber(s) is positioned within the cavity of the bone, the optical fiber(s) is capable of providing for an anti-microbial effect, either prior to, during the delivery of the light-sensitive liquid, or after the light-sensitive liquid has been cured and hardened. It is contemplated the optical fiber(s) may provide for an antimicrobial effect while a fluid, such as water, air, or a light-sensitive liquid is infused through the inner void 210 in the delivery catheter 101 and enters the inner cavity 295 of the expandable member 170.

In some embodiments, after the expandable member 170 is in the correct position within the fractured bone 1102, a delivery system which contains a light-sensitive liquid is attached to the port 195. The light-sensitive liquid is then infused through the inner void 210 in the delivery catheter 101 and enters the inner cavity 295 of the expandable member 170. This addition of the light-sensitive liquid within the expandable member 170 causes the expandable member 170 to expand, as shown in FIG. 34C. As the expandable member 170 is expanded, the fracture 1105 is reduced. Unlike traditional implants, such as rods, that span the fracture site, the expandable member 170 of the present disclosure does more than provide longitudinal strength to both sides of the fractured bone. In some embodiments, the expandable member 170 having the design can be a spacer for reducing the fracture and for holding the fractured and compressed bones apart at the point of the collapsed fracture.

Figure 34D:
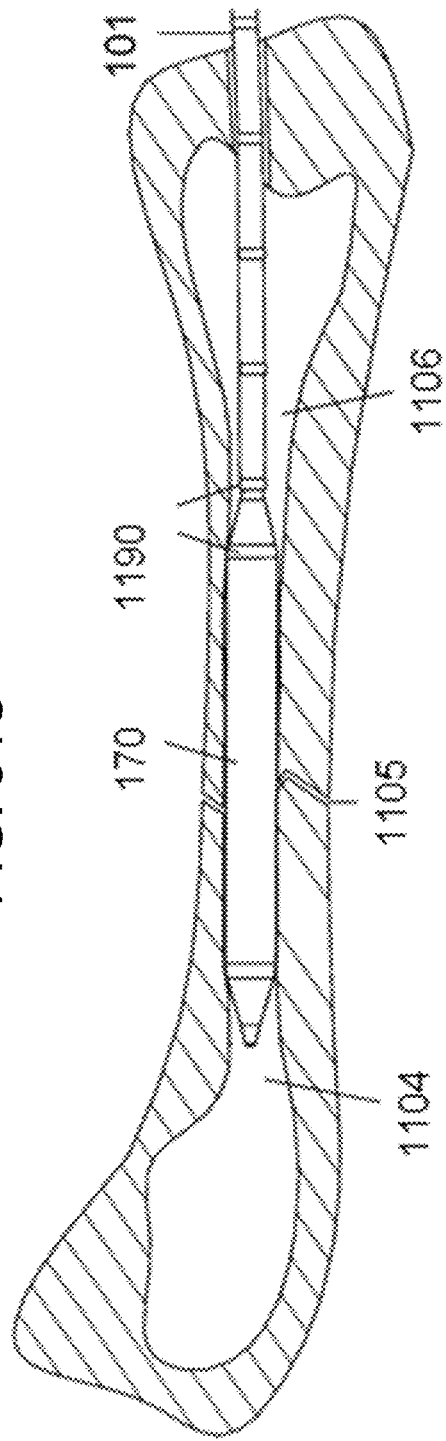

Once orientation of the bone fragments 1104 and 1106 are confirmed to be in a desired position, the light-sensitive liquid may be hardened within the expandable member 170, as shown in FIG. 34D, such as by illumination with a visible emitting light source. In some embodiments, during the curing step, a syringe housing a cooling media may be attached to the proximal end of the delivery catheter and continuously delivered to the expandable member 170. The cooling media can be collected by connecting tubing to the distal end of the inner lumen and collecting the cooling media via the second distal access hole. After the light-sensitive liquid has been hardened, the light source may be removed from the device. Alternatively, the light source may remain in the expandable member 170 to provide increased rigidity.

In some embodiments, subsequent illumination of the bone 1102 and surrounding tissue of the repair site can be performed after the expandable member 170 has been hardened. In some embodiments, where the light source has been removed from the expandable member 170, such subsequent illumination can be performed by reintroducing the light source into the hardened expandable member 170 and activating the light source. In some embodiments, where the light source has been removed from the expandable member 170, such subsequent illumination can be performed by positioning a light source adjacent to the hardened expandable member 170 and directing illumination into the expandable member 170 for distribution throughout the repair site. In some embodiments, where the light source remains in the expandable member 170 (e.g., to provide rigidity as discussed above), the light source can be reactivated to illuminate the repair site. In some embodiments, reactivation of the remaining light source can include reconnecting the light source to an external power or light generating device. In some embodiments, the remaining light source can include a power source (e.g., batteries) for remote activation as needed. In some embodiments, the remaining light source can include inductive circuitry for example, for inductively activating the light source and/or for inductively charging batteries of the light source.

Figure 34E:
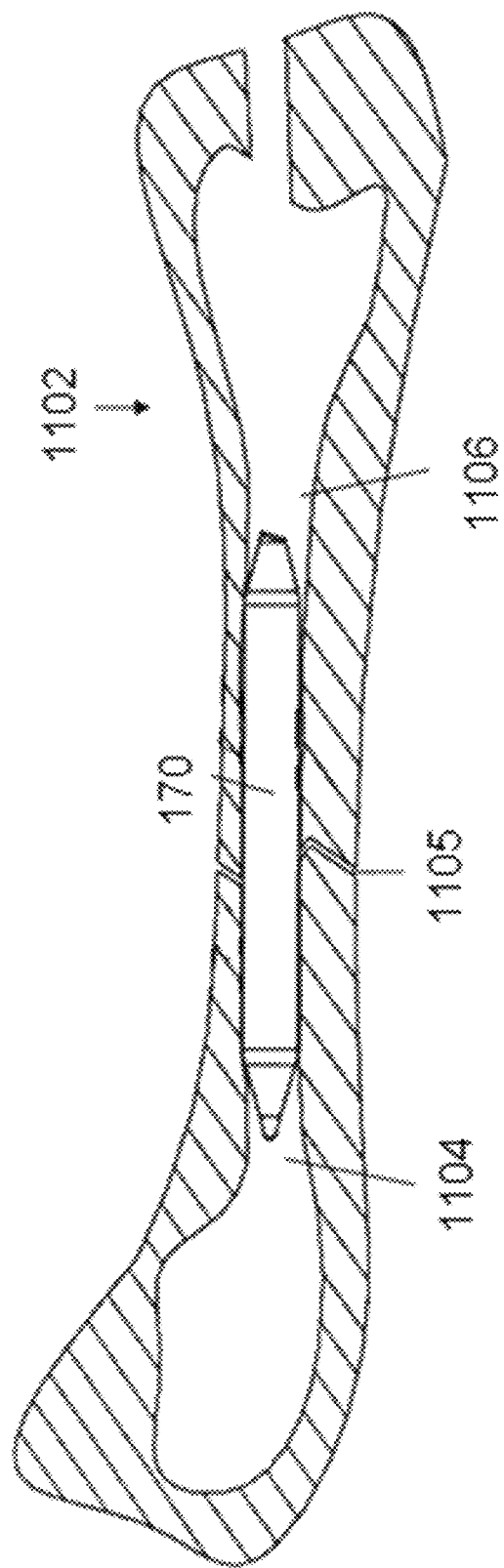

FIG. 34E shows at least one embodiment of a bone fixation device in a cavity of a bone after being separated from an introducer. For example, the expandable member 170 once hardened, may be released from the delivery catheter 101 to form a photodynamic bone fixation device inside the intramedullary cavity of the bone 1102. It is contemplated that optical fiber(s) may be passed in an inner lumen of the photodynamic bone fixation device, and optionally pass through a manifold located within the inner lumen and into a channel located in the photodynamic bone fixation device. Further, it is possible optical fiber(s) may be passed in a channel located within a ridge positioned on an outer surface of the photodynamic bone fixation device. Once the optical fiber(s) are positioned with the cavity of the bone, the optical fiber(s) may provide for an anti-microbial effect.

Applications/Uses for ABLP

While the use of ABLP can be used to address the use of the technology in medical indications, the efficiency of the system allows use in non-traditional applications.

In some embodiments, the system can be used to resolve antimicrobial load in high contact areas (e.g., escalator hand holds, elevators, other high touch contact areas) through the illumination of the blue light to the surface area.

In some embodiments, light sources can be used with personal water bottles where potable water may not be available. For example, fibers and light sources can be embedded in water bottles to kill bacteria.

In some embodiments, light sources can be embedded in cooking preparation tables to ensure that bacterial isn't capable of growth.

In some embodiments, light sources can be used to cover harvested food crops that may be susceptible to bacteria, such as *E coli* breakouts (e.g., lettuce).

While orthopedics is described in detail above, the use of the light source can be applicable to other surgical and medical procedures including but not limited to those medical uses described below.

Dermatology—Blue light has been shown to be effective in the treatment of acne. Acne vulgaris is a chronic inflammatory disorder of the pilosebaceous unit affecting more than 85% of adolescents and often persisting into later adulthood. Conventional therapy with antibiotics and retinoids yields mixed results and can be complicated by antibiotic resistance and adverse treatment profiles. Therefore, newer therapeutic modalities such as light-based therapy have been developed to address the need for acne treatment. A variety of narrowband light sources, intense pulsed light (IPL), lasers, and photodynamic therapy (PDT) have been studied. Treatment with these light sources may offer improvements in inflammatory acne and acne scarring, with more limited benefit for noninflammatory (comedonal) acne.

Mechanism of action of light-based therapies-Previous clinical observations and studies have shown that patients experience acne improvement after exposure to natural sunlight but the specific mechanism had not been elucidated. More recently, it has been postulated that light-based therapies work to decrease *Propionibacterium acnes* level and reduce pilosebaceous unit size and function. Specifically, light is absorbed by porphyrins produced naturally within sebaceous follicles by *P. acnes*. Porphyrins (coproporphyrin III and protoporphyrin IX) absorb light wavelengths between 400 and 700 nm with 415 nm wavelength within the blue light spectrum being most effectively absorbed. Light absorption leads to photo-excitation of porphyrins and subsequent release of singlet oxygen and reactive free radicals that exert bactericidal effects on *P. acnes*. Longer wavelengths, such as red light, activate porphyrins less effectively but penetrate deeper into the skin where it may directly target sebaceous glands and exert anti-inflammatory properties by influencing cytokine release from macrophages. Blue light has also been shown to exert anti-inflammatory effects in keratinocytes.

The use of light and laser in the treatment of acne is increasing as these modalities are safe, effective, and associated with no or minimal complications when used appropriately. These light and laser sources are also being used in combination with pharmacological and/or physical measures to synergize their effects and optimize the therapeutic outcome.

Blue light acne treatment is administered via a blue light delivery system, such as in a mask to reduce distance between the treatment site and the light. The procedure simply involves a patient sitting in front of a blue light lamp for about 15 minutes.

Figure 35:
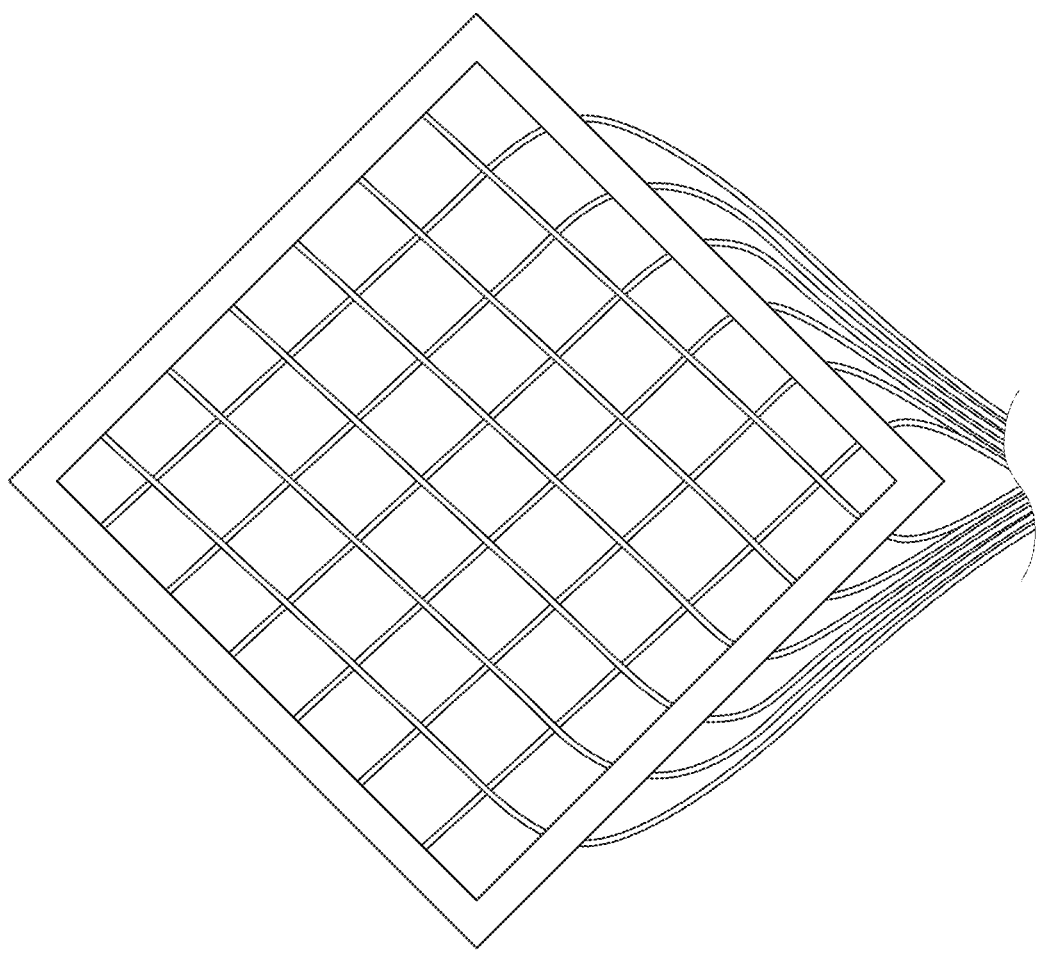
FIG. 35 is an exemplary embodiment of one or more light fibers that are woven into a contact form.
Figure 36B:
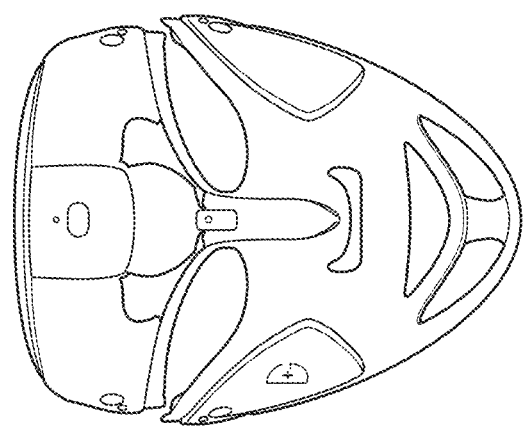
FIG. 36A and FIG. 36B illustrate exemplary devices for providing light therapy for treatment of the skin.
Figure 36A:
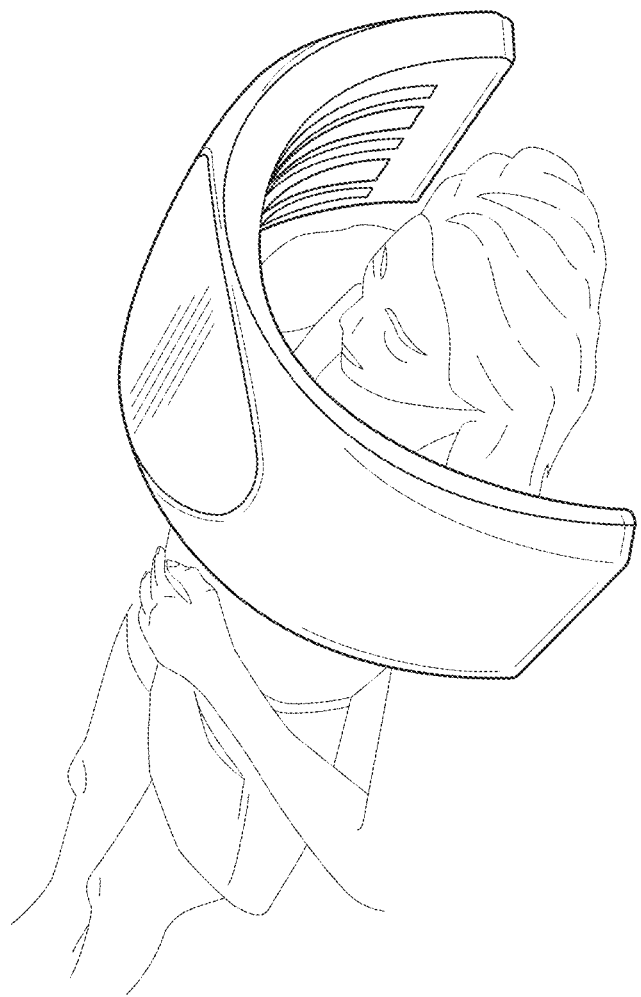

In some embodiments, light fibers are woven into a fiber/mask or other contact form such that the patient applies the shape to the affected area, as shown in FIG. 35 and FIG. 36A and FIG. 36B. The intimate contact can ensure even power distribution. In some embodiments, the light fibers can be applied to a clear fluid mask where the light fibers are encased in a form fitting mask. The light can be transmitted through the mask material to the affected skin.

ENT Applications—Blue light can also be applied in the ear, nose and throat (ENT). For example, chronic rhinosinusitis (CRS) is a common chronic condition that can benefit from antimicrobial photodynamic therapy (aPDT), a noninvasive nonantibiotic broad spectrum antimicrobial treatment. aPDT can be used to treat CRS polymicrobial antibiotic resistant *Pseudomonas aeruginosa* and MRSA biofilms in a maxillary sinus cavity model.

Bandages—Light fibers can be woven into a material that is used for a wound bandage. For example, the bandage can be a matrix of fibers with linear fibers in a single direction, a cross hatch "checkerboard" of fibers, or a spongy mass of fiber where the light source is attached to a coiled/ball/mass of light fibers. The bandage can include one or more ports to energize the fibers in the bandage, or can include a battery.

Direct effects of light on pain and inflammatory mediators such as histamine, serotonin, bradykinin, and prostaglandins have been documented. Further, light treatments can promote epithelial migration and proliferation, endothelial migration and organization for angiogenesis, inflammatory infiltration, macrophage phagocytoses, immune surveillance, fibroblast matrix synthesis, and wound contraction, among other things. For example, light treatments can be used to promote epithelial cell functions, especially their basal colony-forming units (stem/progenitor cells) that not only can aid re-epithelialization but also promote regeneration of skin appendages such as glands and hair follicles.

Chronic wounds—Chronic wounds are defined as wounds that do not heal for at least 180 days (3 months) and do not proceed through the normal reparative process. These wounds usually present with lack of tissue integrity and volume, pain, and persistent inflammation and are often infected. The initiating injury in these wounds can vary from physical (pressure, burns, or radiation), chemical, electrical, or immunologic injuries that all result in persistent tissue damage). These wounds can be illuminated either via a traditional bandage with light fibers embedded. For example, the light fiber illumination system is battery operated system, allowing for patient mobility and the ability for the patient to maintain their activities of daily living without encumberage to plug in power units.

The fibers can also have a physical benefit to the bandage as the absorbent materials of a bandage can be mounted above the fibers. The fiber diameter can act as a spacer with the wet fluids of the wound being drawn up and away from the wound site while the surface illumination provides a treatment modality for these issues. The smooth surface of the fiber can also preclude ingrowth and incorporation into the tissue healing matrix.

Many chronic wounds are "wet" which has been shown to assist in healing, prevent skin breakdown. However the "wet" nature off the wound also allows for a rich environment for infection. The application of the blue light can assist in the healing while preventing the potential for infection/bacterial growth. The blue light applied to the wet wound area can help to reduce the potential for a pooled area of bacteria.

Venous Ulcers, Pressure Ulcers, and Diabetic Foot Ulcers—Diabetic foot ulcers, being notoriously difficult to cure, are one of the most common health problems in diabetic patients. There are several surgical and medical options already introduced for treatment of diabetic foot ulcers. Blue light can be used as a treatment option for open wounds.

Bone—As mentioned above, ABLP can be used in a variety of procedures. In some embodiments, ABLP can be used in treatment of bone, either inside or outside the bone. The treatment of infections may not be limited to the interior of the bone, and there may be cases where the external portion of the bone is infected. The application of the light to treat the infections needs to be in close proximity to the afflicted area, hence methods and means to deliver light must be adjusted to the specific indications.

Osteomyelitis is inflammation of the bone caused by an infecting organism. Although bone is normally resistant to bacterial colonization, it can get infected in multiple ways. The infecting organism may reach bone through blood or events such as trauma, surgery, the presence of foreign bodies, or the placement of prostheses that disrupt bony integrity and predispose to the onset of bone infection. When prosthetic joints are associated with infection, microorganisms typically grow in biofilm, which protects bacteria from antimicrobial treatment and the host immune response.

Infectious periostitis is the term used for infection that invades the periosteum only and does not involve the cortex and bone marrow. With infectious (or suppurative) periostitis the changes are subtle and may be identified by a periosteal reaction. As the infection penetrates into the cortex but does not invade medullary bone, the term infectious osteitis is used. Once the infection involves both cortex and bone marrow, the more accurate term is osteomyelitis.

The term septic arthritis is used to describe infection of a joint. Joint infection, such as *Staphylococcus aureus*, erodes cartilage and decreases joint mobility.

Osteomyelitis secondary to contiguous soft tissue or by direct extension depends on the mechanism of transmission. For example, a puncture wound is most commonly affected by *Staphylococcus* or *Pseudomonas*, whereas an animal bite from a dog or a cat can cause an infection from *Pasteurella multocida*. *Pseudomonas* is also seen in nosocomial infections.

Fungal osteomyelitis may mimic bacterial or tuberculosis infection of bone both clinically and radiographically.

As the bone is encased and surrounded in tissue, muscle, etc., a means of delivery of the light fiber to these areas may include the use of a long thin hollow cannula with a sharpened tip, that allows the light fiber to be inserted. The cannula is delivered within the specific location of the infection, and the cannula withdrawn, leaving the fiber in place.

In some embodiments, the system can be used with minimally invasive soft tissue delivery. Within the capsule of the bone (e.g., joint), the fiber can be delivered into tissues surrounding/adjacent/into joints. The fiber can be loaded into a large bore hollow needle (such as biopsy needle diameter, or other thin walled metal/plastic cannula that can be used to deliver the fiber). The cannula can be positioned in the tissue and then withdrawn while the fiber is held in position (the cannable pulled back over the fiber), The fiber can be illuminated in places where it could not be typically delivered without large invasive/exposing surgery.

In some embodiments, ABLP can be used prior to the application of a bone plate, or after the application of a bone plate to treat an infected bone plate. The fiber may similarly require placement in contact with, in proximity to external fracture stabilization plates, e.g., femur, tibia, fibula, ulna, radius, and distal radius plates.

The light fiber can be placed in close proximity to these external plates, held in position by suture that is affixed to the plate and surrounding the fiber and ensuring a position close to the plate and close to the infection. In some cases, where the plate is not held in tight apposition to the bone (e.g., a locking plate vs a compression plate), the light fiber may be able to be positioned under the plate to illuminate the space between the plate and the periosteal surface.

In some embodiments, ABLP can be used in a trauma situation, for example, in the treatment of an open wound or a broken bone. For example, in trauma indications, the patient/afflicted area/open wound/compound breaks where the bone is exposed to external pathogens can be wrapped/encased in a wrap/bandage/protective dressing on top of the wound to prevent the growth/transmission of bacteria.

External fixatures, such as ones made of metal or polymer frames, can be attached to the bone or can be percutaneously penetrating the skin and driven into the bone as a means to provide stability to the bone while healing. For example, a "shanz screw" can be used and is driven into the bone and resides/exits the skin to provide attachment to one or more cross fixation bars This screw that exits the skin can be a location point for infection to migrate from skin to bone. A light and/or light fiber can be attached to the external part of the screw to illuminate the screw and/or tissue interface to prevent bacterial growth.

In some embodiments, the light source can be mounted at both ends of the fiber, for example in those indications where long lengths of fiber may be needed or the fiber is very thin (e.g., the bandage concept—the steel wool/fluffy mass of fibers) multiple light sources can be added to the fiber. This confirmation of light sources can be used with any of the embodiments disclosed herein.

In some embodiments, ABLP can be used in orthopedic applications, including but not limited to the knee, ankle, shoulder, elbow, wrist and foot.—joints (infections in synovial fluid of a joint)

Ear Infections—In some embodiments, a probe can be attached to a light source, and the probe with one or more optical fibers can be delivered to the ear canal. For example, the probe can be delivered to the middle ear, just behind the eardrum. The light can be directed to the infected ear, emitting light from the device into the ear canal, exposing the canal to sufficient light to reduce or eliminate the infection.

Gynecology/Urology—In some embodiments, ABLP can be used in gynecological applications. For example, a vaginal speculum or other vaginal dilator of clear, translucent materials can have one or more light fibers/light delivery embedded therein and can be used towards the treatment of gonorrhoeae or other gynecological issues.

The system can also be used in urology applications, such as in the urinary track or inside a catheter. For example, catheter-associated urinary tract infections are the most common hospital-acquired infection, for which *Escherichia coli* is the leading cause. The use of blue light from 405 to 470 for inactivation of *E. coli* attached to the silicone matrix of a urinary catheter. The use of a dual lumen catheter—where the light fiber is placed within a small 1.7 mm lumen that has a clear pathway to allow light to be delivered within the main lumen of the catheter (for urinary fluids). The use of a multi lumen catheter, where the light fibers are placed within small 1.7 mm lumen that has a clear pathway, allows light to be delivered within the main lumen of the catheter (i.e., for urinary fluids). Note that the two or more fibers may be more effective as only the interior portion of the light fiber is delivering light to the internal lumen of the catheter.

In some embodiments, a catheter based delivery system can be placed and left in position while a urinary catheter is in place and then removed. When the urinary catheter needs to be removed/replaced with a new one, the component for light delivery can be left in place. In some embodiment, urinary catheters for men may have one fiber placed within the catheter and one fiber that is placed around the catheter at the point of entry to the urethra to preclude bacteria transmission on the surface of the catheter from entering the body. This can form a layered stacked system having a fiber within the lumen of the catheter. When the catheter is placed within the urethra, there is a secondary light source/fiber to kill the potential bugs that would be entering the space urethra-catheter junction. This allows for light coming from within and light emitting at the junction point.

Respiratory Applications—In some embodiments, ABLP can be used in respiratory applications, for example, relating to the trachea or a ventilator. For example, critically ill patients can contract ventilator-associated pneumonia. This nosocomial infection increases morbidity and likely mortality as well as the cost of health care. Xray or MRI can be taken to discern the location of a pneumonia, and the light fiber can be delivered via a brocoscope or other device to the affected area, where the diseased tissue illuminated. Similarly a fiber residing in an endotracheal tube or other ventilator tubing can be used to mitigate any buildup of bacteria.

It should be noted that light can be delivered to any to internal tissue or orifice (i.e., percutaneous delivery). In some embodiments, a user can take an image, including Xray and MRI, to discern the location of the light delivery mechanism and the tissue and/or bone to be treated. the fiber shall have a radiopaque marker/markers on it so as to provide visualization to the user in defining the position/location of the fiber. The use of ancillary instrumentation towards delivery and guidance may be used, both for placement and for subsequent direction and/or adjustment of the fiber, such as components that allow for a steerable distal end.

Examples

The following paragraphs provide experiments regarding the present disclosure relating to killing of orthopedic relevant pathogens using blue light.

Overview

Figure 37:
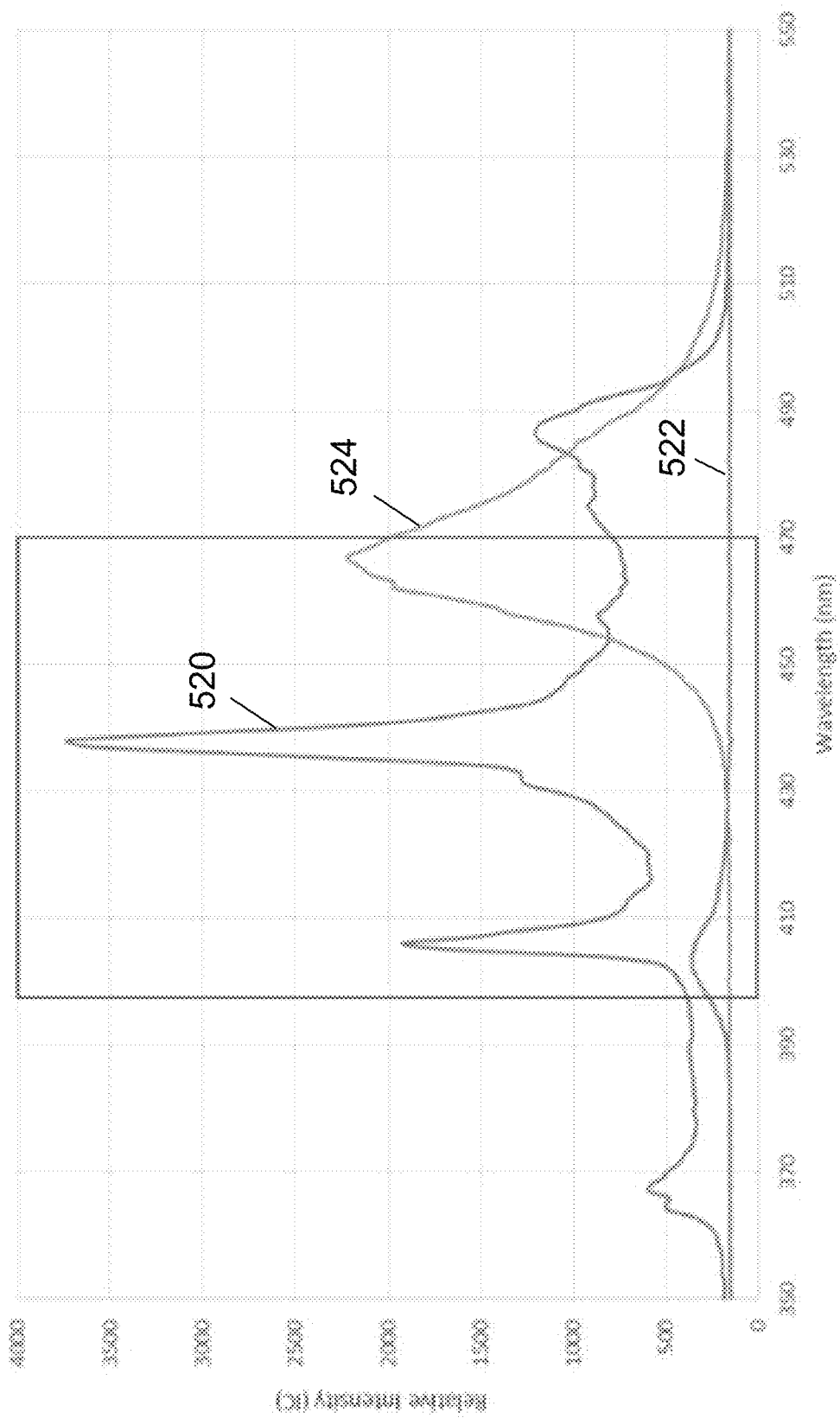
FIG. 37 illustrates the results of an experiment that shows wavelengths of light that are shown to be antimicrobial against orthopaedic relevant bacteria.

It is believed that blue light with wavelengths outside of the UV spectrum can have antimicrobial properties for both Gram-negative and Gram-positive bacteria. Currently, a clinical trial using blue light for photodynamic bone stabilization has begun, in accordance with aspects of the present disclosure. The question of whether the blue light used for photodynamic bone stabilization could kill orthopaedic relevant bacteria was asked because one of the major outputs from the optical fiber at spectrum of visible blue or violet light wavelengths (see FIG. 37) has been shown to eradicate methicillin-resistant. FIG. 37 illustrates an exemplary graph showing the output (line 520), positive control (405 nm—line 522), positive control (470 nm—line 524). The box area highlights the wavelengths of light (405 nm to 470 nm) that has shown to be antimicrobial against orthopaedic relevant bacteria. The blue light has a major peak in the region of 405 nm. While experimental results focused on wavelength of 405 nm, even better results are obtained by using multiple frequencies of blue light or a spectrum of visible blue or violet light wavelengths. For example, 4 of 5 frequencies can be pushed down the same fiber by individual LEDs (each individually controlled). It will be understood that any number of light frequencies can be used, including 10, 20, 100 or more. These various frequencies can be used associated with different bacteria, including but not limited to MRSA, *Staphylococcus, Streptococcus, Enteroccocous, Psuedomonas,* and *Candida*.

TABLE 1

| Microbe of Interest | Wavelength | Radiant exposure | Inactivation efficacy | |
|---|---|---|---|---|
| MRSA | 415 | 168 | 4.82-log10 | CFU |
| MRSA | 412 | 28.5 | 72% | |
| MRSA | 450 | 28.5 | 81% | |
| MRSA | 405 | 121 | 91.20% | |
| MRSA | 465 | 112.5 | >2-log10 | CFU |
| MSSA Staphylococcus | 400 | 50-108 | >5-Log10 | CFU |
| Staphylococcus | 405 | 133 | 5.20-6.27 log10 | CFU |
| Staphylococcus | 405 | 118-214 | >4-log10 | CFU |
| Streptococcus | 405 | 133 | 5.20-6.27 log10 | CFU |
| Streptococcus | 405 | 137-260 | 3.2-4.3log10 | CFU |
| Enteroccocous (including VRE) | 405 | 118-2214 | >4-log10 | CFU |
| Enteroccocous (including VRE) | 400 | 50-108 | >5-log10 | CFU |
| Pseudomonas | 400 | 50-180 | >5-Log10 | CFU |
| Pseudomonas | 415 | 110 | 7.64-log10 | CFU |
| Pseudomonas | 470 | 480 | 92.40% | |

TABLE 1-continued

| Microbe of Interest | Wavelength | Radiant exposure | Inactivation efficacy |
|---|---|---|---|
| Pseudomonas | 405 | 133 | 5.20-6.27 log10 CFU |
| Pseudomonas | 405 | 118-2214 | >4-log10 CFU |
| Pseudomonas | 470 | 80-180 | 47% to 2.87-log10 CFU |
| Candida | 405 | 288-576 | 5-log10 CFU |
| Candida | 415 | 70 | 5.42-log10 CFU |
| Candida | 405 | 332 | 4.52-log10 CFU | to be bactericidal may be determined by an equation E=Pt, where E is in $J/cm^2$, P is in $mW/cm^2$ and t is time in seconds. It was determined from previous studies that a dose of 36 $J/cm^2$ is toxic to bacteria but not harmful to mammalian cells.

Figure 38A:
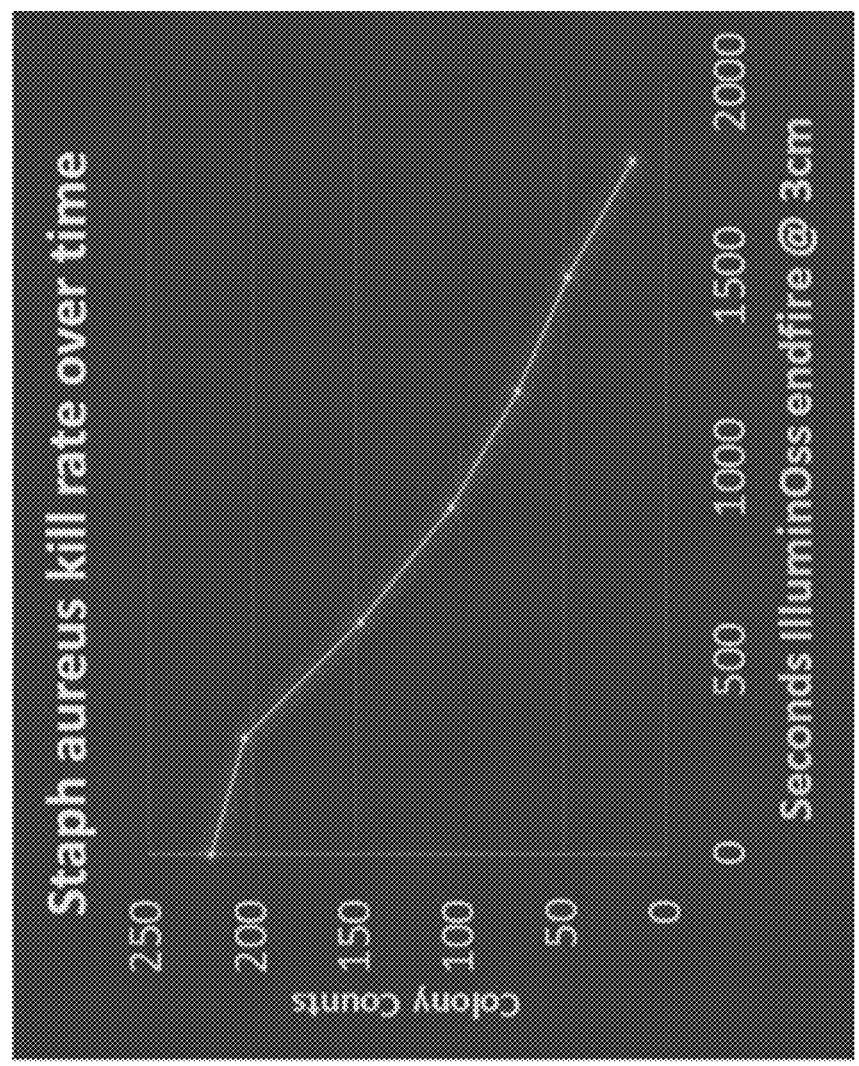
FIG. 38A and FIG. 38B illustrate the results of an experiment that demonstrates a time-dependent killing of MSSA with the light at energy levels that are not toxic to mammalian cells.
Figure 38B:
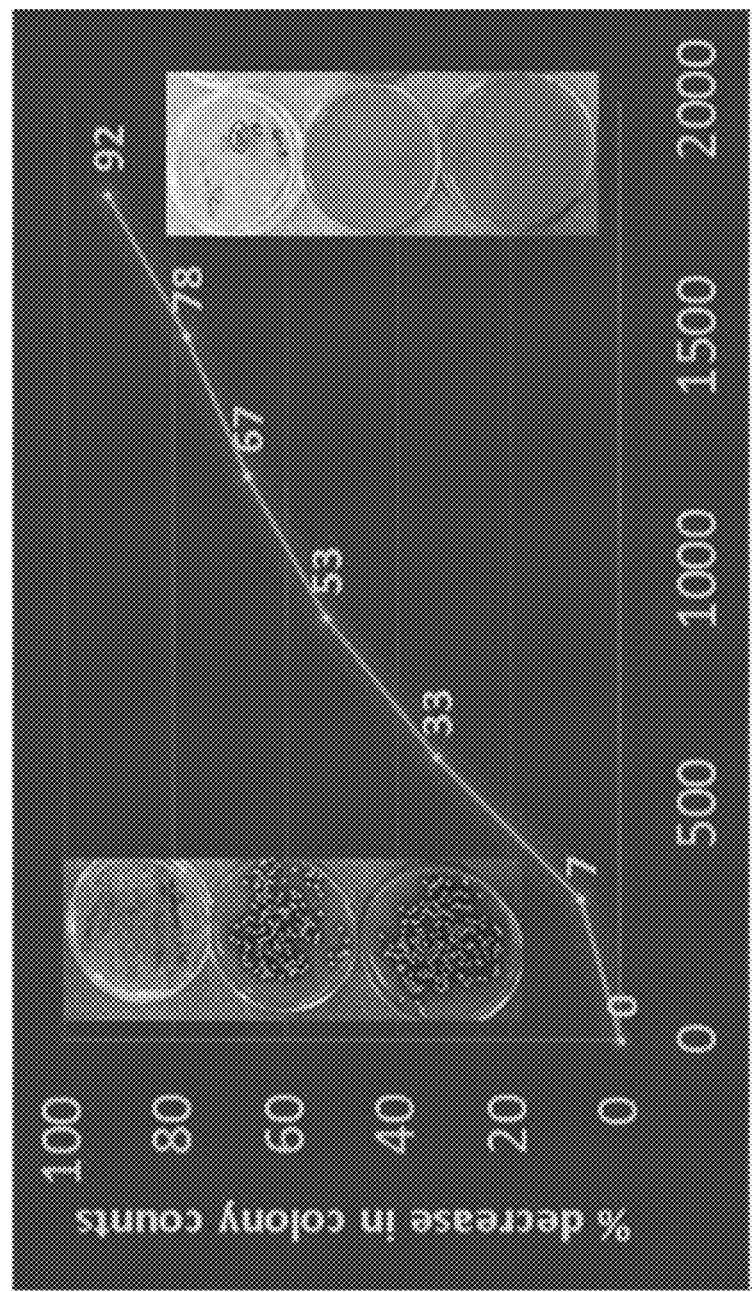

Initial suspension culture experiments were conducted demonstrating a time-dependent killing of MSSA with the light at energy levels that are not toxic to mammalian cells (see FIG. 38A and FIG. 38B). Further testing will allow for further characterization of this effect on patient isolated from

TABLE 2

Summary of blue light inactivation of bacteria in vitro

| Light source | Radiant exposure | Bacterial species/strains | Inactivation efficacy |
|---|---|---|---|
| 407-420 non metal halide lamp | 324 $J/cm^2$ at lamp aperture, lamp-target distance: 25 cm. | P. acnes | 15.7% reduction in CFU immediately after irradiation, 24.4% reduction 60 min after irradiation. |
| 407-420 nm intense light lamp | 75-225 $J/cm^2$ | P. acnes | 2 $log_{10}$ at 75 $J/cm^2$, 4 $log_{10}$ at 150 $J/cm^2$, and 5 $log_{10}$ at 225 $J/cm^2$. |
| 405-nm diode laser | 20 $J/cm^2$ | H. pylori | >99.9% |
| 405 nm light-emitting device | 15 $J/cm^2$ at lamp aperture | P. gingivalis | >75% |
| 380-520 hm broadband light | 4.1-42 $J/cm^2$ | P. gingivalis, P. indermedis, P. nigrescens, P. melaninogenica, and S. constellatus | P. intermedis and P. nigrescens > 5 $log_{10}$ at 4.2 $J/cm^2$; P. melaninogenica > 5 $log_{10}$ at 21 $J/cm^2$; P. gingivalis 1.83 $log_{10}$ at 42 $J/cm^2$. |
| 400-500 mm light lamps used for dental restoration | Irradiance between 260 and 1300 $mW/cm^2$ for up to 3 min | P. gingivalis, P. nucleatum, S. mutans, E. faecalis | For minimal inhibitory dose for P. gingivalis and F. nucleatum was 16-62 $J/cm^2$, for S. mutans and E. faecalis was 159-212 $J/cm^2$. |
| 405-nm superluminous diode light | 50.4-55.2 $J/cm^2$ at lamp aperture, lamp-target distance: 1-2 mm | MRSA USA 300, MRSA IS-853 | 92.1% for USA 300; 93.5 for IS-853 |
| 420-nm superluminous diode light | 55 $J/cm^2$ at lamp aperture; lamp-target distance: 1-2 mm | MRSA USA 300, MRSA IS-853 | 90.4% for both strains |
| 405 and 470 nm light | 15 $J/cm^2$ | S. aureus, P. aeruginosa | S. aureus 90% at 405 nm, 62% at 470 nm, P. aeruginosa 95.1% at 405 nm, 96.5% at 470 nm. |
| 405 nm light | 23.5 $J/cm^2$ | S. aureus | 2.4-$log_{10}$ |
| 405-cm LED | 36-216 $J/cm^2$ for gram-positive; 108-180 $J/cm^2$ for gram-negative. | S. aureus, S. epidermidis, S. pyogenes, E. faescalis, C. perfringens, A. baumannii, P. aeruginosa, E. coli, P. vulgaris, and K. pneumoniae | 2.6-5.0 $log_{10}$ for gram positive; 1.1-1.7 $log_{10}$ for gram negative. |
| 415 and 485 nm LED | 60-120 $J/cm^2$ | S. aureus, E. coli 51 | S. aureus 90% at 415 nm; 50% at 455 nm, E. coli 100% at 415 nm; 98-99% at 455 nm. |

Null Hypothesis

Blue light is not capable of bactericidal activity against orthopaedic relevant bacteria because it does not have enough energy to be bacterial.

Objective

Using suspension cultures, we will test the following: (1) Does light kill MSSA and MRSA in a time dependent manner? (2) Does light kill patient isolated bacterial from orthopaedic infections? and (3) Does the implant have bactericidal activity during the time required for intra-operative polymerization (about 15 minutes)?

Significance

It is possible blue light may indicate that broad-spectrum antimicrobial effects that can be generated for both Gram-negative and Gram-positive bacteria. The antimicrobial effect may be due to bacteria intracellular porphyrins and the production of cytotoxic reactive oxygen molecules. Light in the visible spectrum may have the most effective wavelength for antimicrobial effects with the region of about 402-420 nm, which appear to be most promising. It is encouraging that one of the major peaks for emission is in this blue light region (see FIG. 37). However, the blue light inactivation of bacteria may be dependent on dose. The dose of light needed orthopaedic infections and to test the potential bactericidal effect during a 15 minute implant curing process.

Research Design and Method

Suspension cultures have been used to determine the effect of blue light on bacterial inactivation. This method is used to study the effect of blue light on MSSA ATCC 29213. The bacterial strain was diluted in 0.9% NSS until reaching an optical density of 0.5 McFarland units ($1.5 \times 10^8$ CFU/ml). Initial experiments were completed to determine the correct serial dilution in NSS to obtain about 200 colonies per 100 ul inoculum onto 100 mm blood agar plates (see FIG. 38A and FIG. 38B for colony counts). After final dilutions to a concentration that is relevant to cause orthopaedic related infections (around $10^5$), 3 ml of bacterial suspension was used for the light dosing experiments. A "end fire" fiber optic cable and R&D light box were included and then the intensity of light emitted from the end of the fiber optic cable to be 17.4 $mW/cm^2$ in the wavelengths from about 395-415 nm was calculated. This "end fire" cable was used for the dosing experiments.

From a distance of 2 cm above the suspension culture surface the "end fire" light was delivered to the culture. 100 ul samples were taken after vortexing at 0, 5, 10, 15, 20, 25 and 30 minutes of continuous light treatment with duplicate experiments performed. The 100 ul bacterial suspension samples were streaked onto 100 mm blood agar plates and immediately placed into an incubator for 24 hrs at 37° C. at 5.5% $CO_2$. After 24 hrs the plates had colonies counted and data presented as % kill over time. Several controls were used including a 30 minute control of bacterial suspension in the 0.9% NSS with plating and colony counts that were not different from the 0 minute control indicating no effect of diluent over time. Additionally, since light generates heat the bacterial suspension cultures had direct temperature measurements. This did show that the suspensions increased from room temperature to 26.2° C. during the 30 minute treatment time indicating that the decrease in colony counts were not due to temperature effects. Initial experiments were done in a hospital microbiological laboratory.

It is noted the implant takes 15 minute for the polymerization step. It is therefore encouraging that the data in FIG. 38A and FIG. 38B indicate a bactericidal effect within this timeframe. The experiment showed to kill orthopaedic relevant bacteria.

Figure 39A:
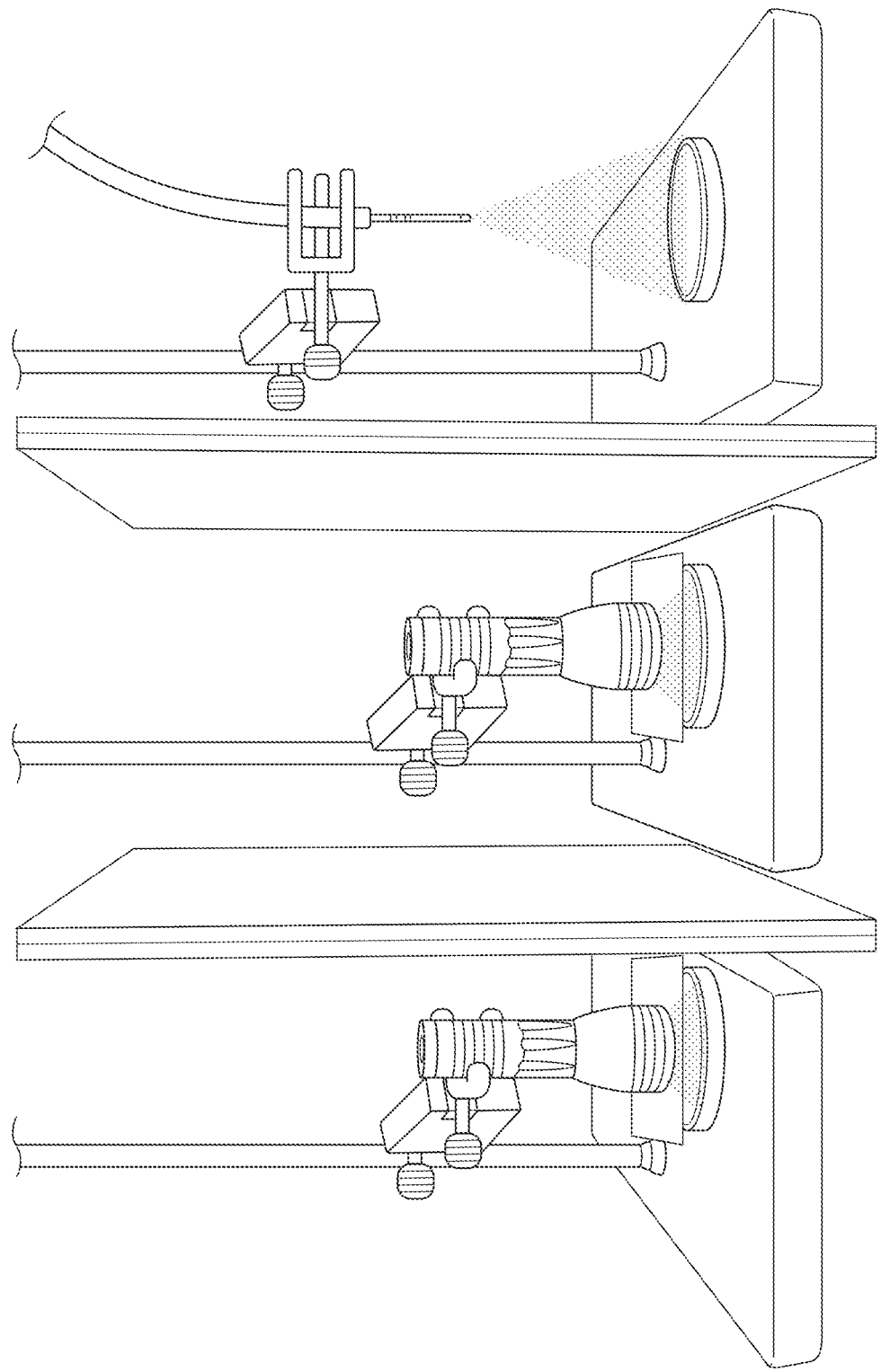
Figure 39D:
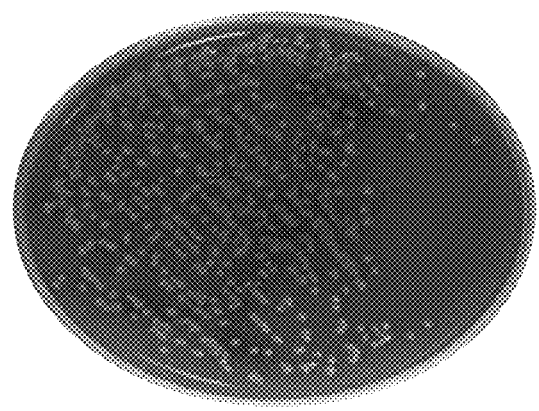
Figure 39C:
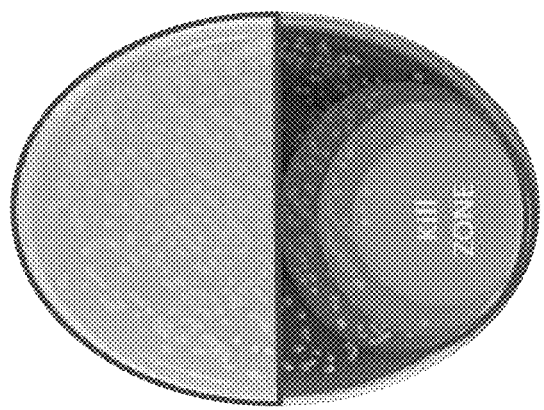
Figure 39B:
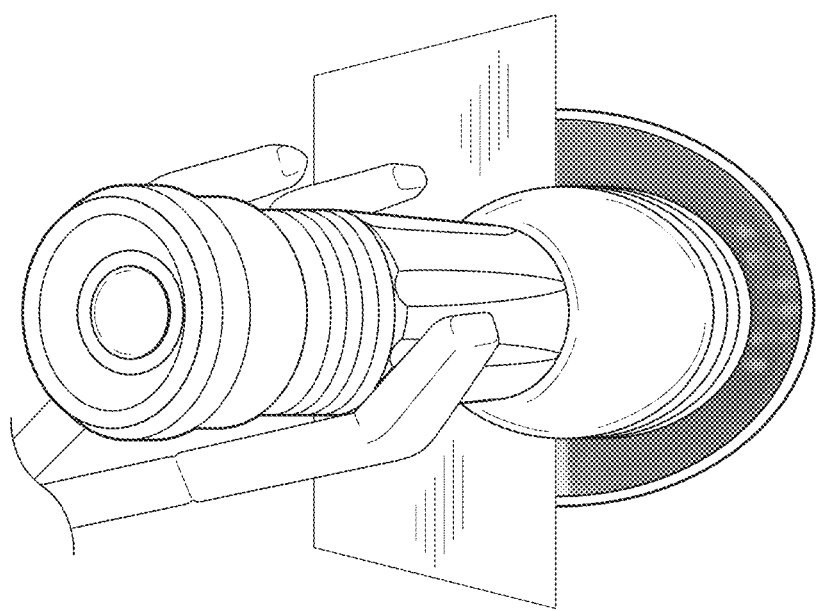
Figure 39E:
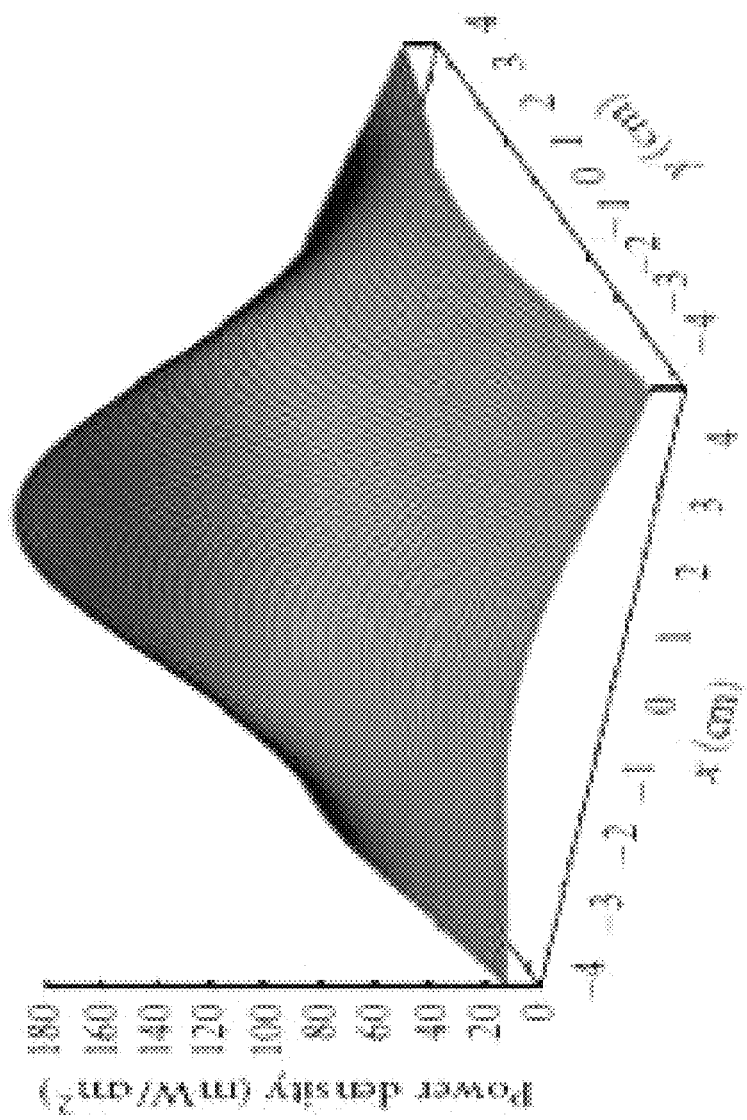
Figure 39F:
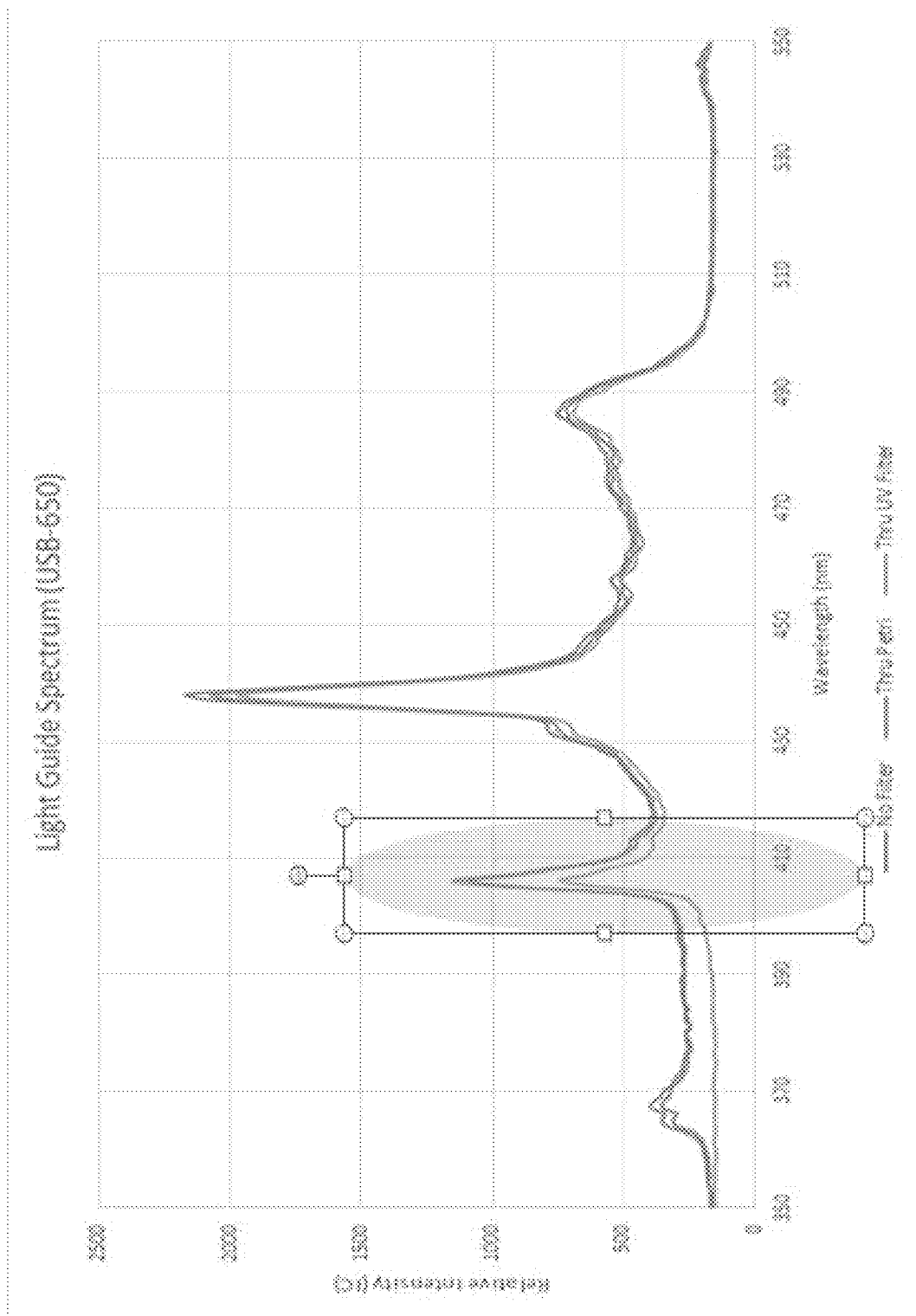

FIG. 39A, FIG. 39B, FIG. 39C, and FIG. 39D show the initial experimental set up. FIG. 39E indicates heat generation issues with change to optical fiber (POF). FIG. 39F indicates the identified wavelength via experimentation is about 405 nm. FIG. 39G indicates through results of experimentation that blue light works to have an anti-microbial effect on bones.

Figure 40B:
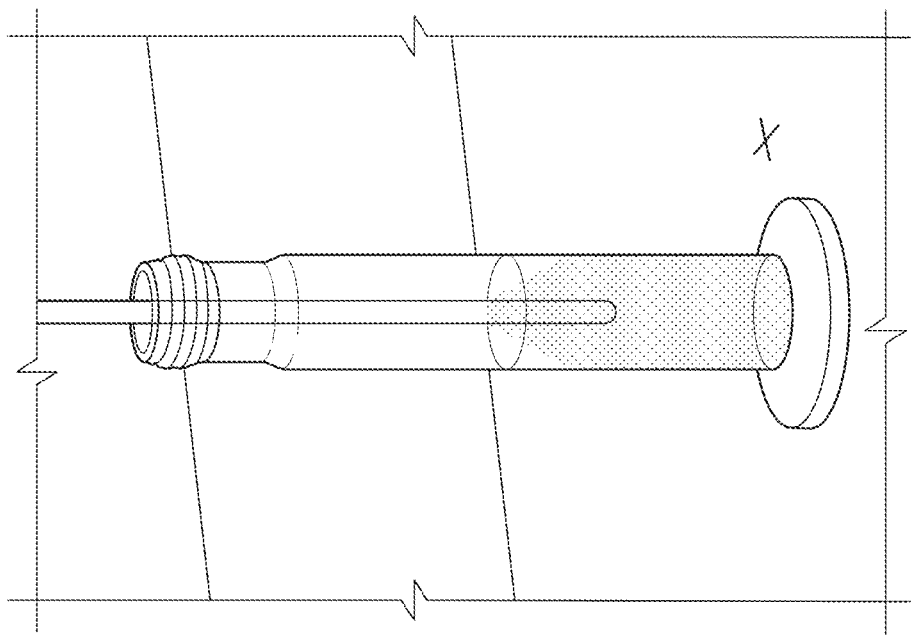
FIG. 40A, FIG. 40B, FIG. 40C, FIG. 40D, FIG. 40E, FIG. 40F, FIG. 40G, FIG. 40H, FIG. 40I, FIG. 40J, FIG. 40K, FIG. 40L, FIG. 40M, FIG. 40N, FIG. 40O, and FIG. 40P show the optical fiber (POF) experimental set up.
Figure 40A:
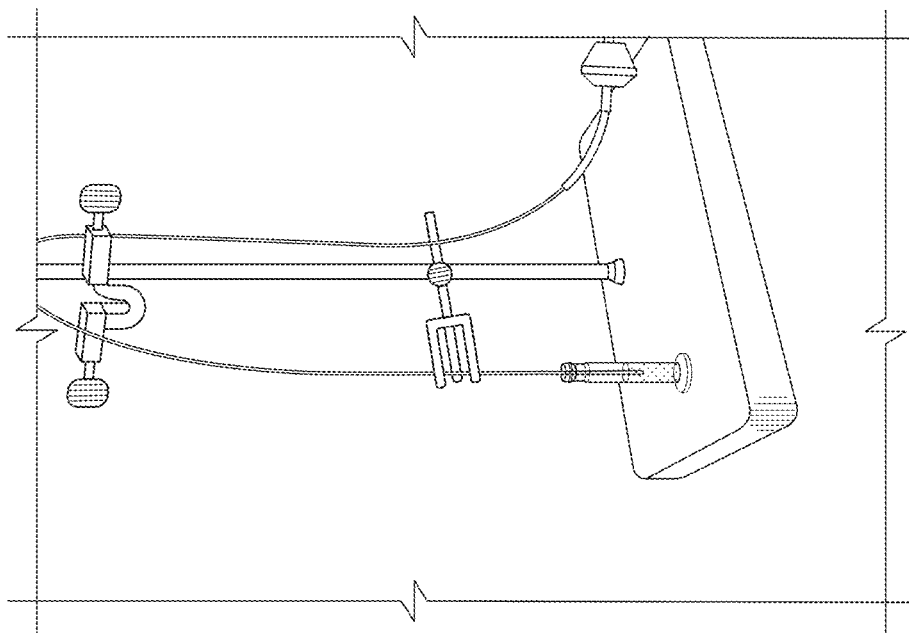
Figure 40C:
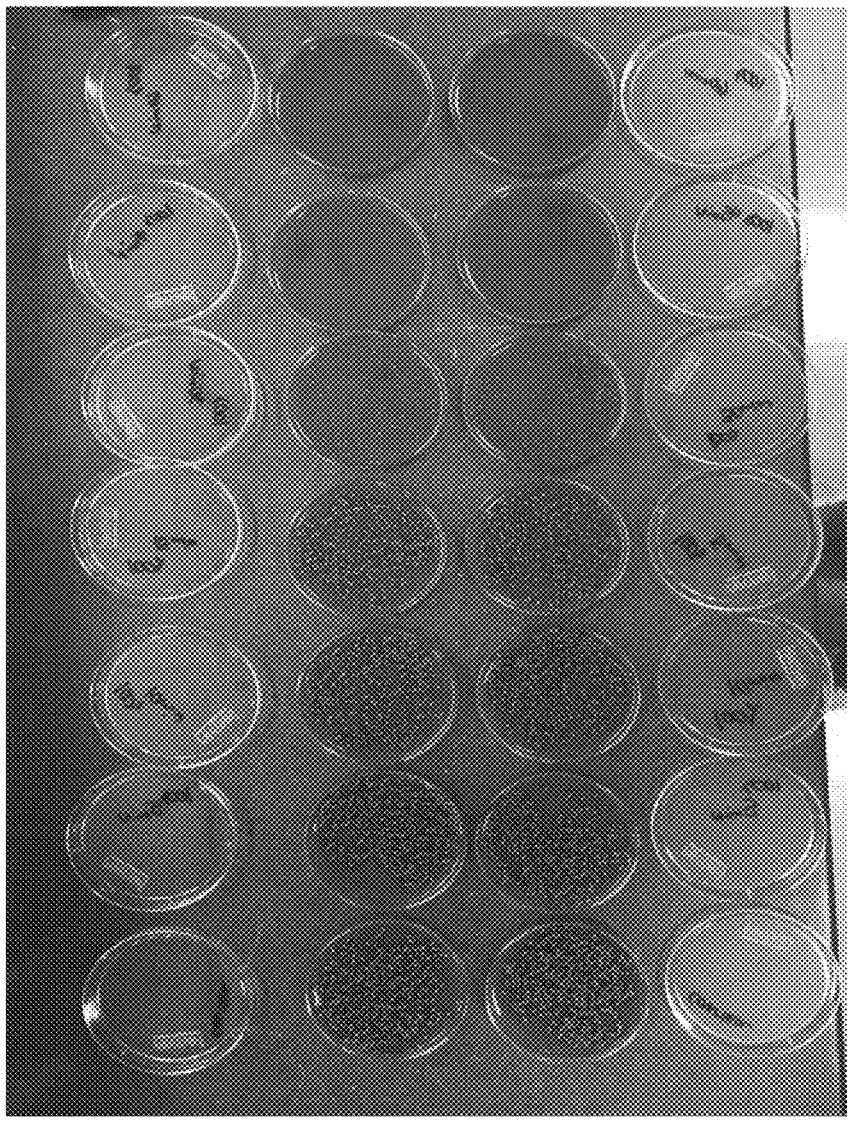
Figure 40D:
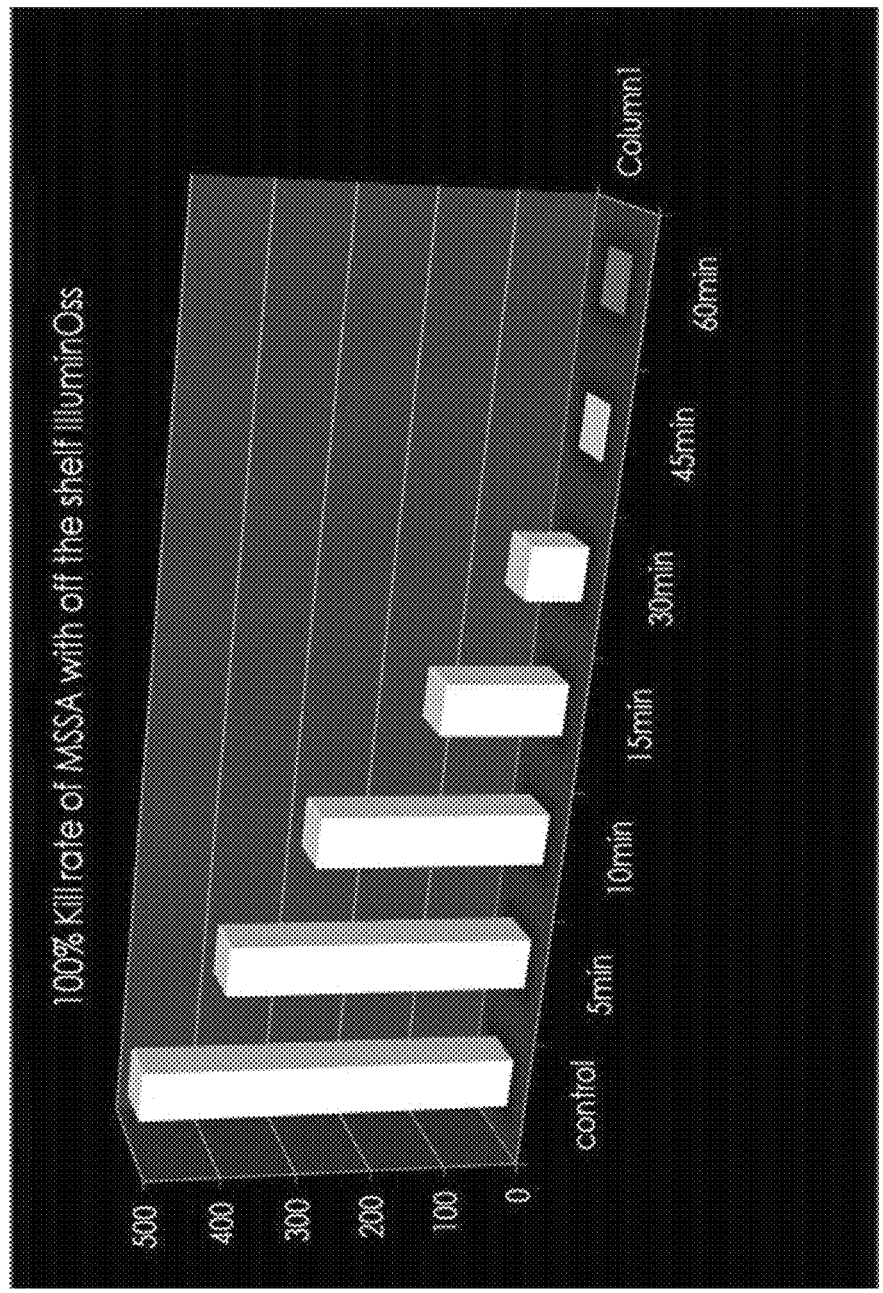

FIG. 40A, FIG. 40B, FIG. 40C, FIG. 40D, FIG. 40E, FIG. 40F, FIG. 40G, FIG. 40H, FIG. 40I, FIG. 40J, FIG. 40K, FIG. 40L, FIG. 40M, FIG. 40N, FIG. 40O, and FIG. 40P show the optical fiber (POF) experimental set up. FIG. 40A and FIG. 40B indicate MRSSA, ATCC29213, dilution in NSS, 3 cm distance from optical fiber (POF), 5, 10, 15, 30, 45 and 60 minute time. Plating over time of 100 ul, blood agar. FIG. 40C shows patient isolated cultures treated with blue light. FIG. 140D shows a graph resulting in a 100 percent kill rate of MSSA with a device.

Figure 40F:
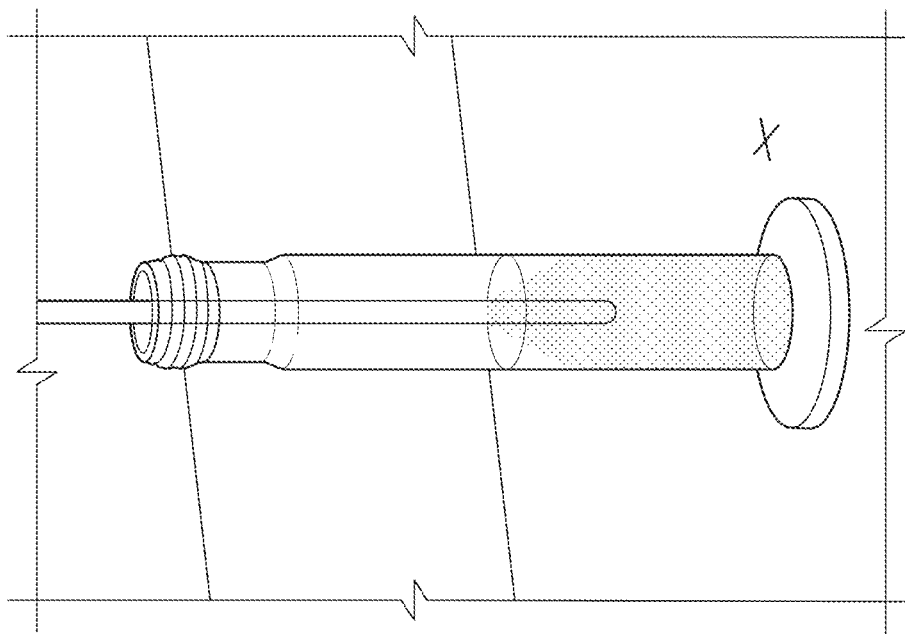
Figure 40E:
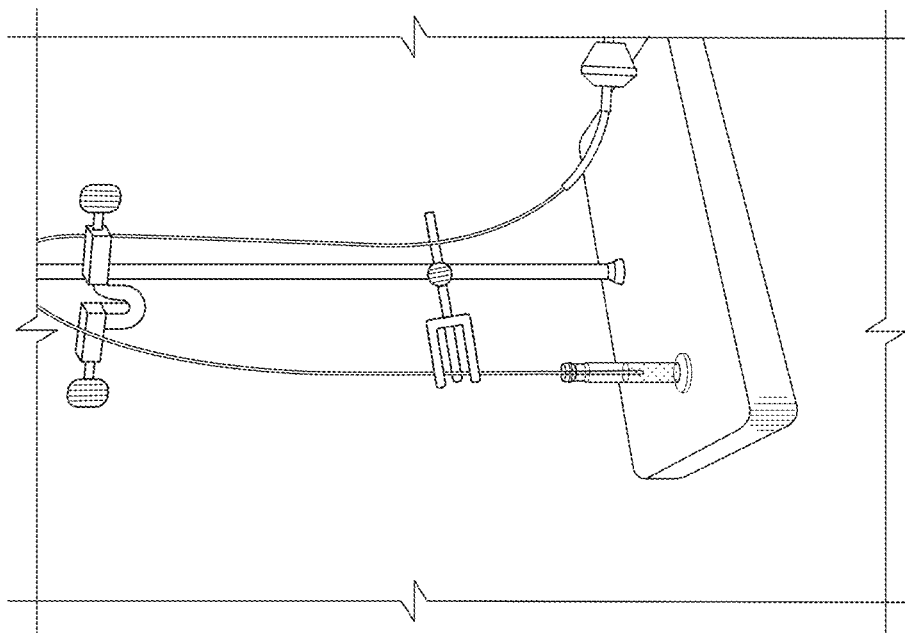
Figure 40G:
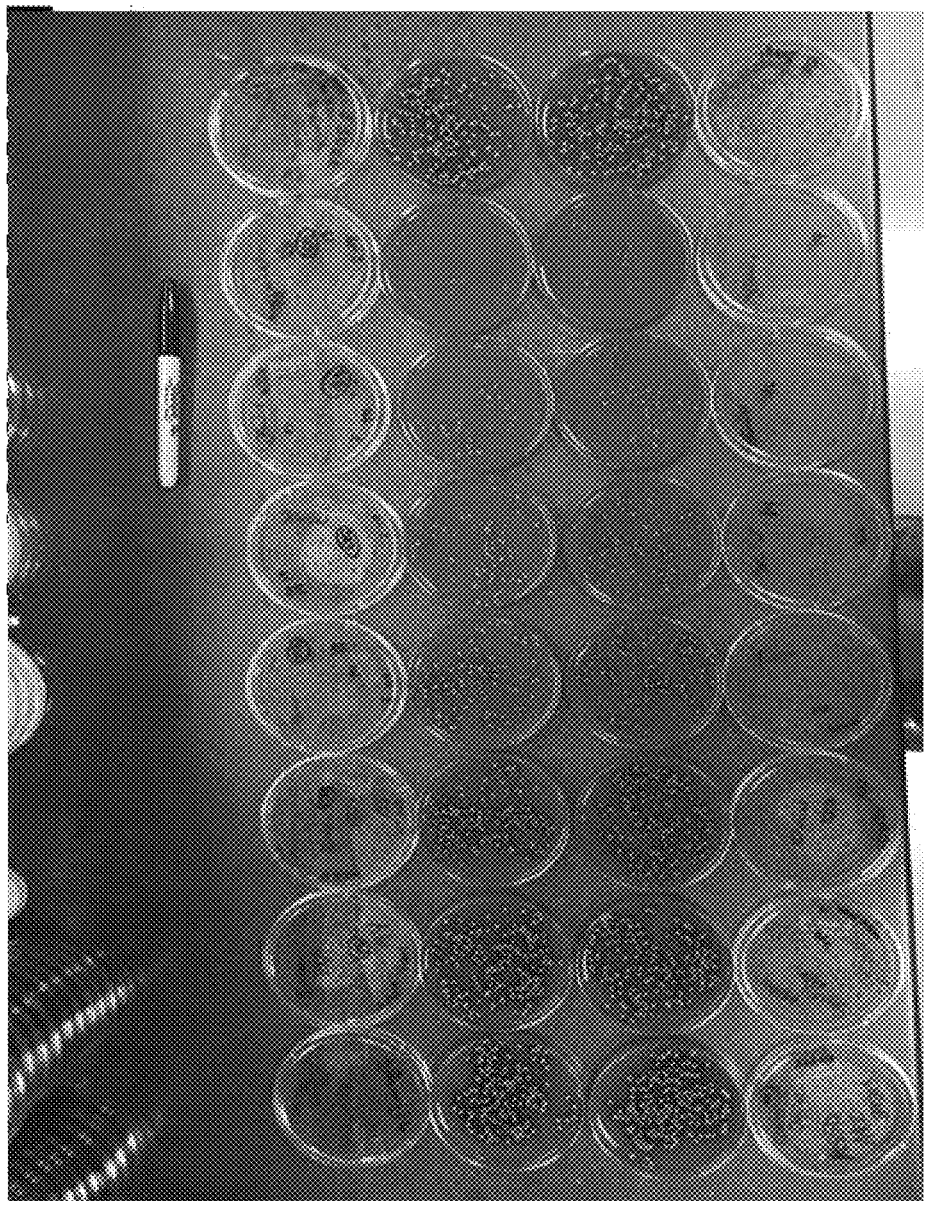
Figure 40I:
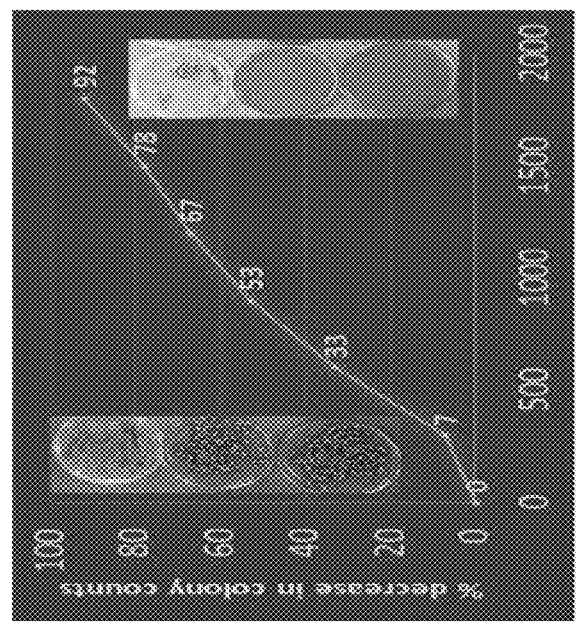
Figure 40H:
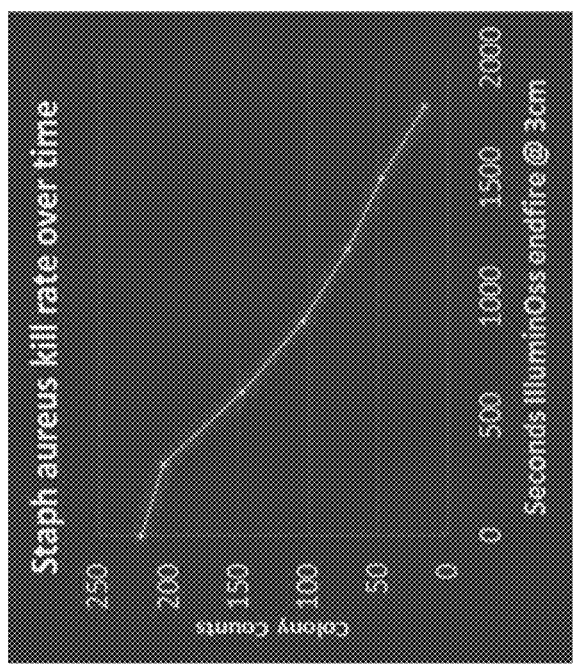
Figure 40J:
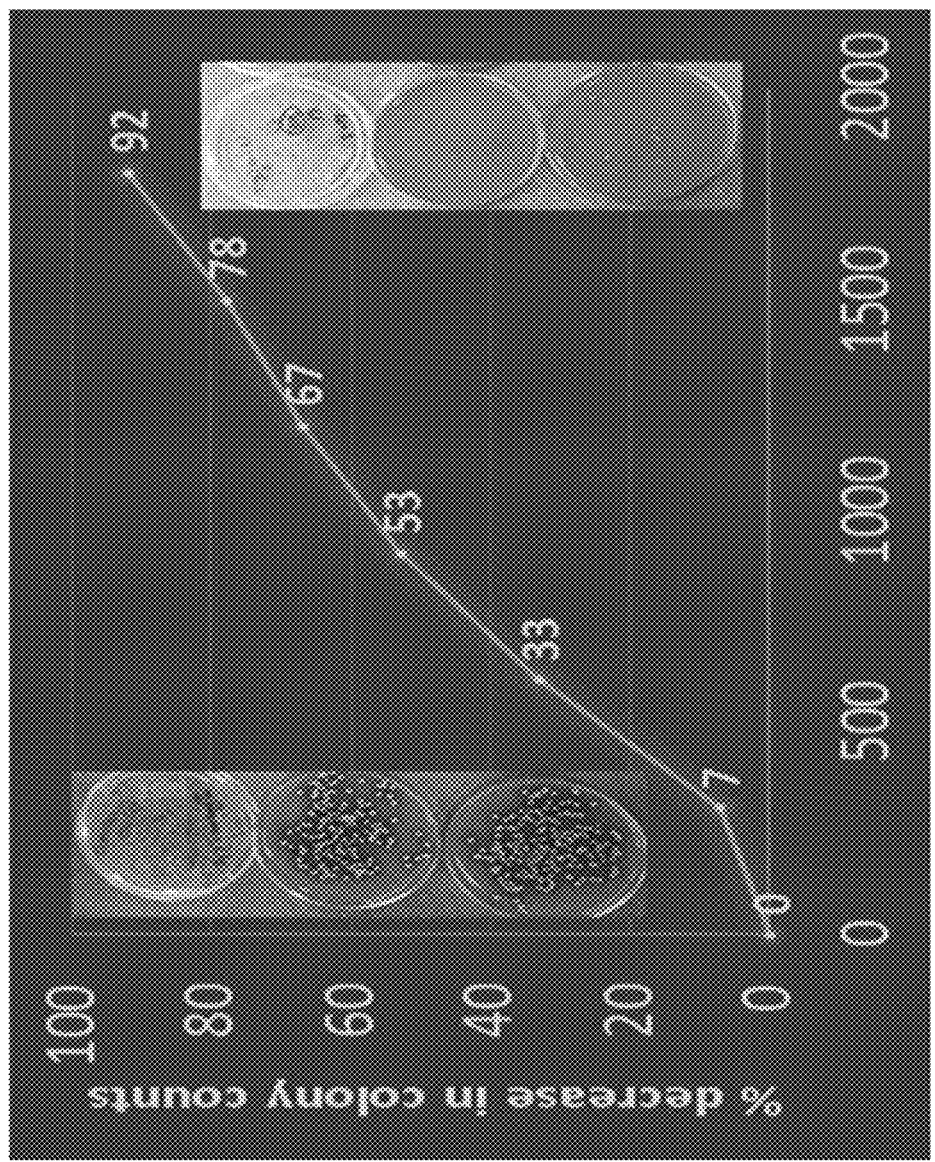

FIG. 40E and FIG. 40F indicate MRSSA, ATCC29213, dilution in NSS, 2 cm distance from the optical fiber (POF), 5, 10, 15, 20, 25 and 30 minute time. Plating over time of 100 ul, blood agar and additional control. FIG. 40G shows patient isolated cultures treated with blue light. FIG. 40H shows a graph resulting in a staph *aureus* kill rate over time. FIG. 40I and FIG. 40J show the percent decrease in colony counts versus time.

Figure 40K:
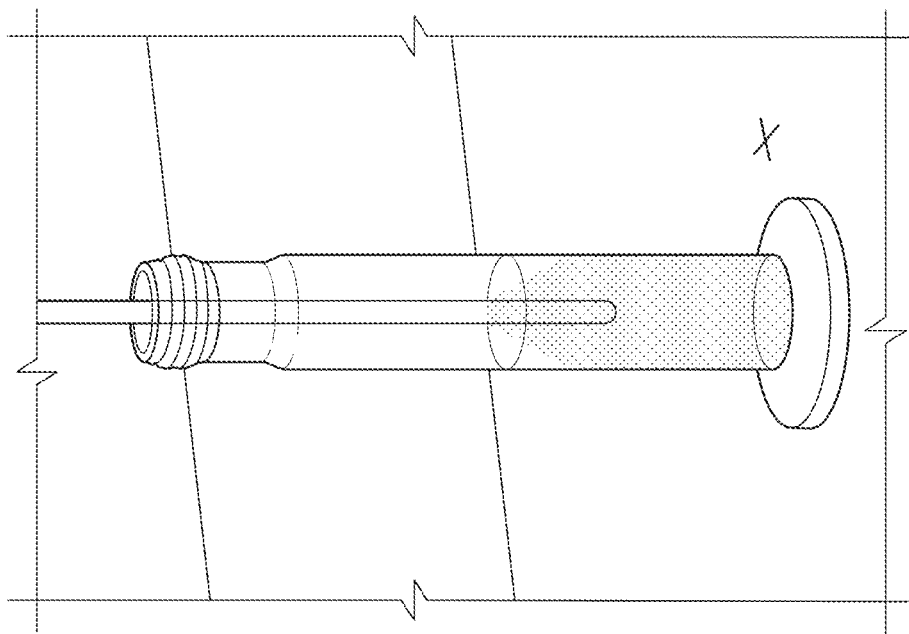
Figure 40L:
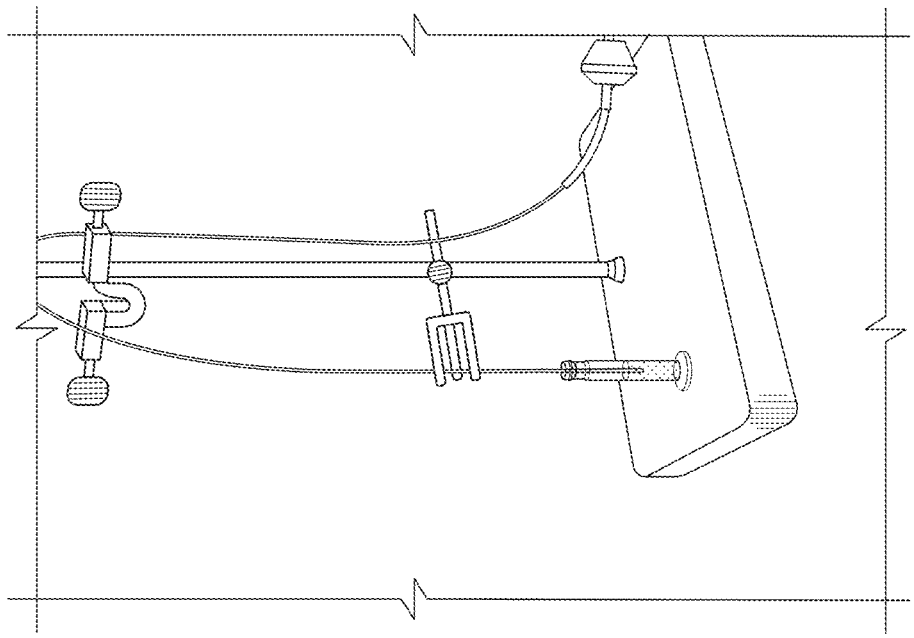
Figure 40M:
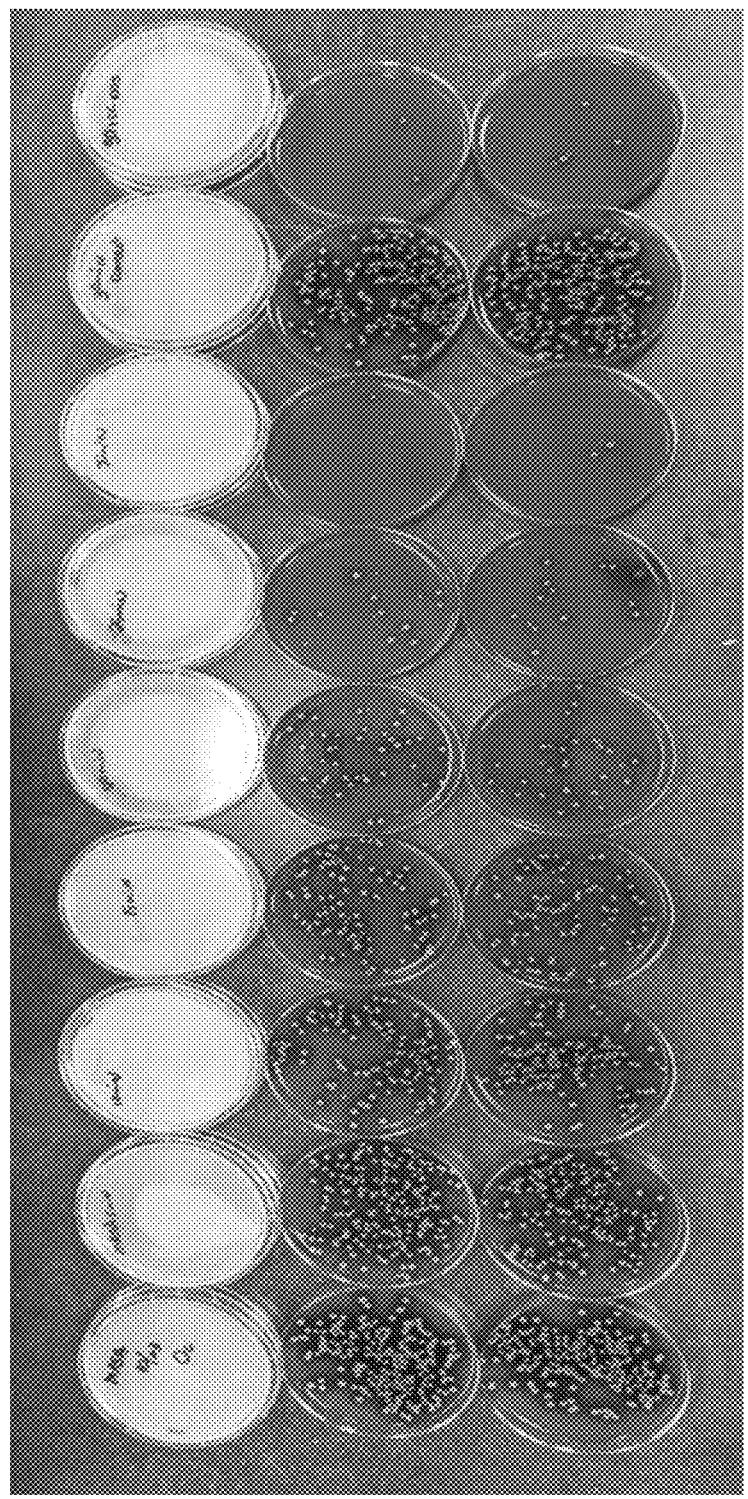
Figure 40O:
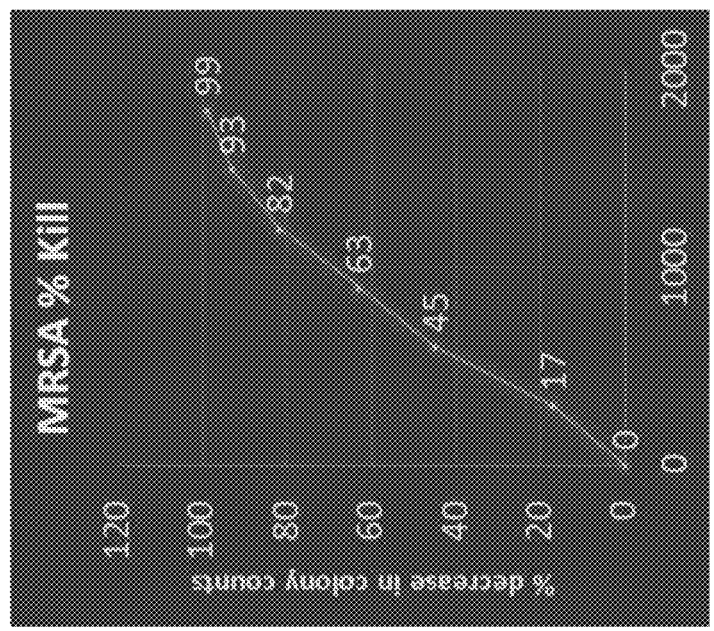
Figure 40N:
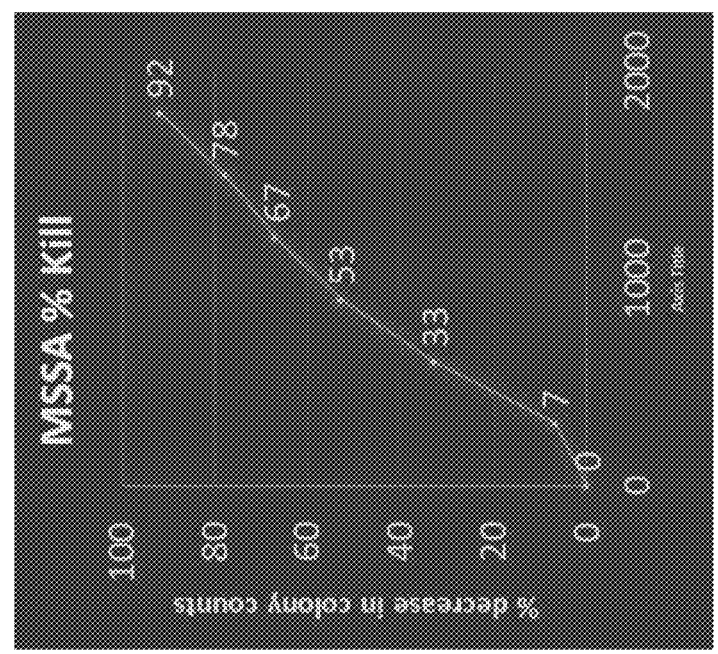
Figure 40P:
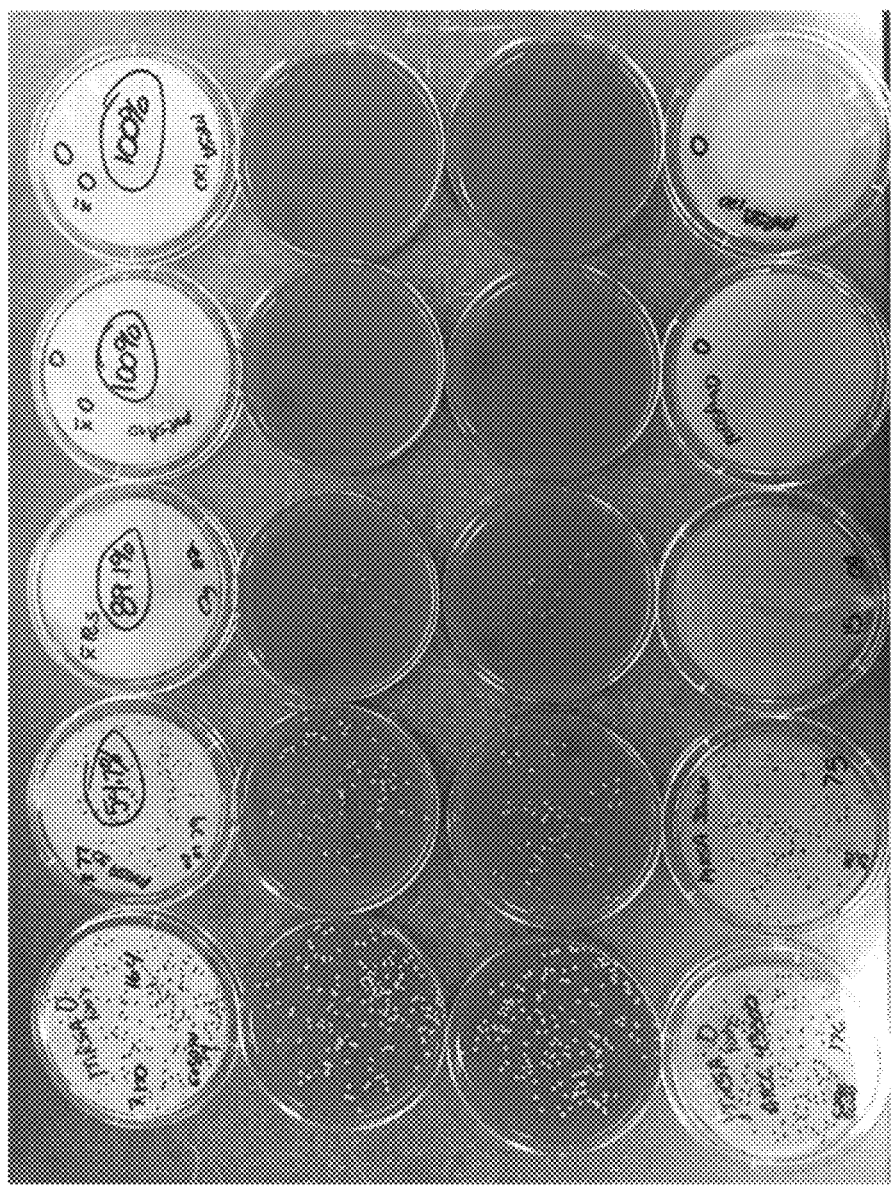

FIG. 40K and FIG. 40L indicate the Oct. 23, 2015 trial that included: Patient isolate MRSA, dilution in NSS, 2 cm distance from the optical fiber (POF), 5, 10, 15, 20, 25 and 30 minute time. Plating over time of 100 ul, blood agar and additional control. FIG. 40M shows patient isolated cultures treated with blue light. FIG. 40N and FIG. 40O indicate the optical fiber (POF) kills MSSA and MRSA. The POF experiment provided light delivered by the optical fiber (POF) that is bactericidal at clinically relevant times to clinically relevant bacteria. It is noted that completed experiments were in the "right" energy delivery in $J/cm^2$ at 405 nm. Finally, wound healing is NOT affected by blue light— (HINS light 5 $mW/cm^2$ for 1 hour no effect on fibroblast function). FIG. 40P shows patient isolated cultures treated with blue light.

Figure 41A:
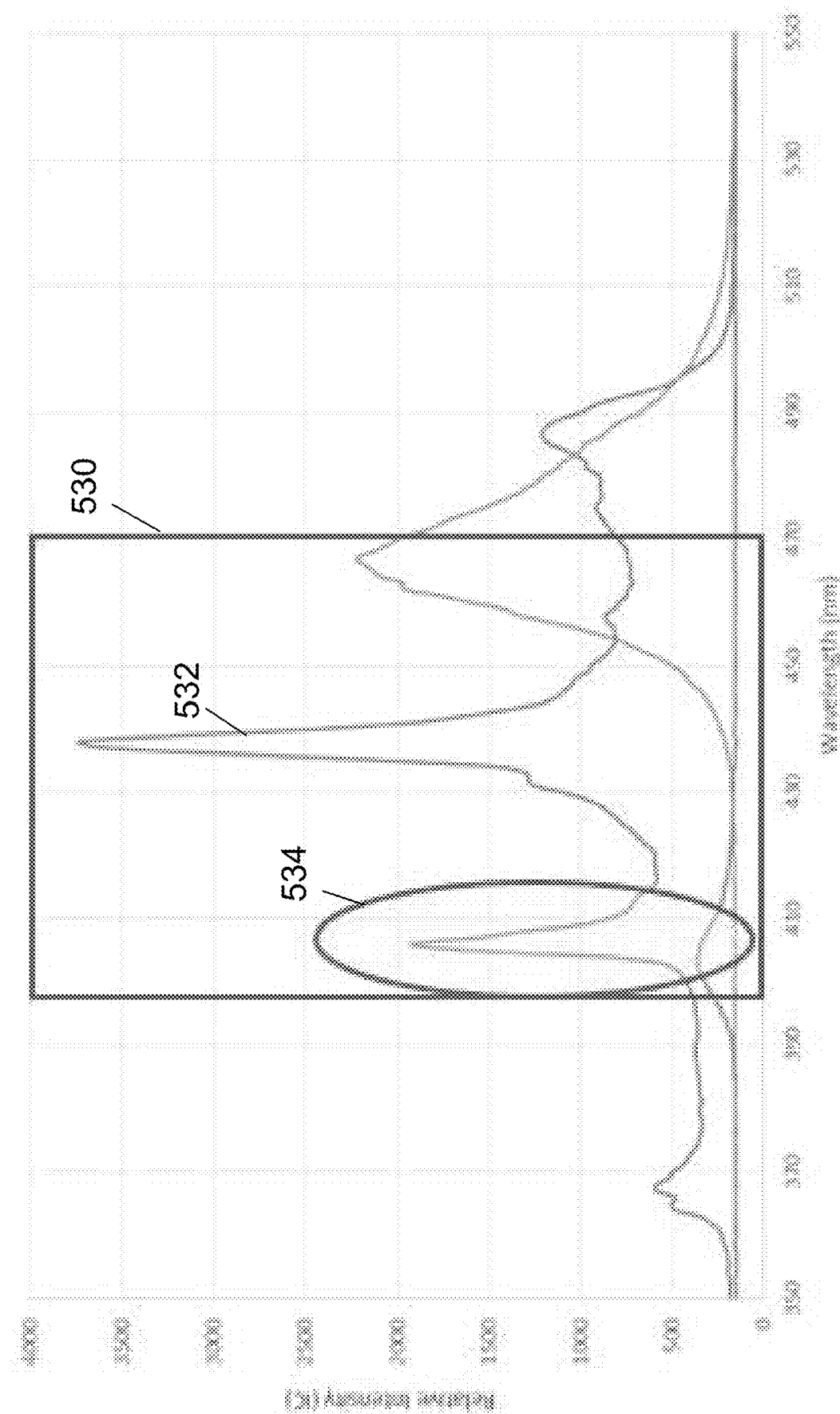
FIG. 41A is an exemplary graph that shows the spectral output from the fiber optic cable used in the device.
Figure 41C:
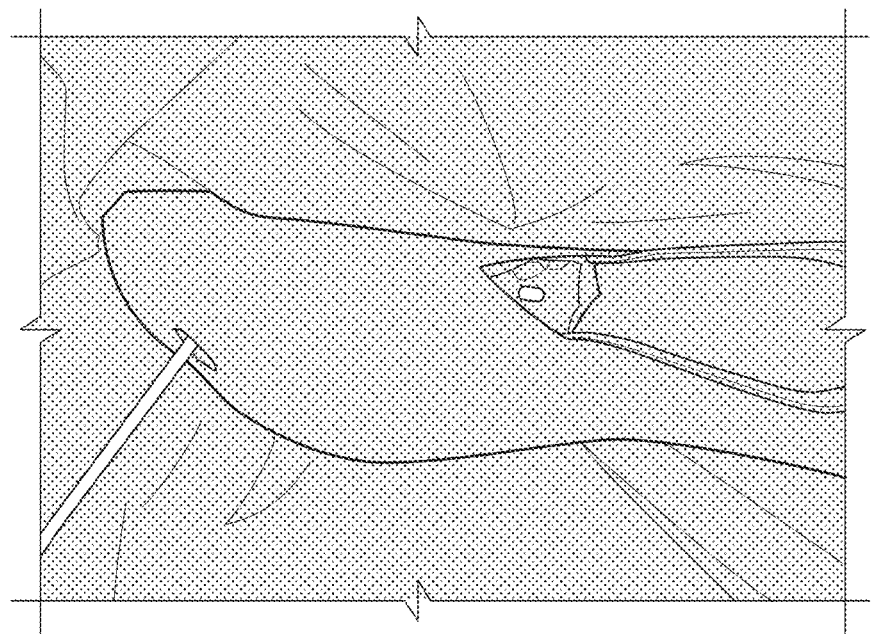
FIG. 41B and FIG. 41C show the blue light output from the site of humeral biopsy.
Figure 41B:
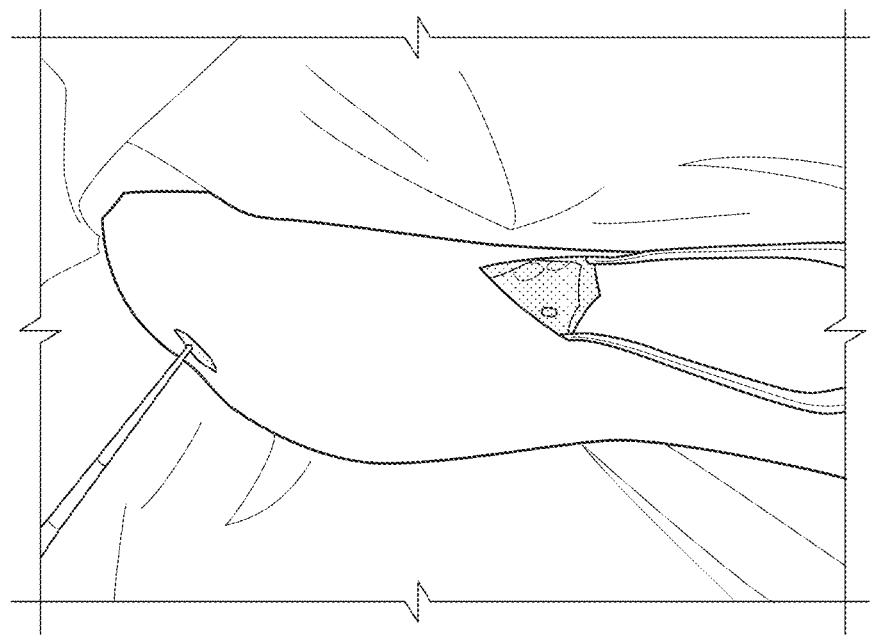

Referring to FIG. 41A, FIG. 41B and FIG. 41C show an intraoperative stabilization of a humerus fracture showing the blue light output. FIG. 41A is an exemplary graph that shows the spectral output from the fiberoptic cable used in the device. FIG. 41B and FIG. 41C show the blue light output from the site of humeral biopsy.

According to aspects of the disclosure, the use of blue light may kill MRSA, such that the blue light can provide sterilization of orthopaedically relevant pathogenic bacteria, among other things. For example, blue light, with wavelengths outside of the UV spectrum, can have antimicrobial properties for both Gram-negative and Gram-positive bacteria (using blue light for photodynamic bone stabilization. It is possible, by non-limiting example this antimicrobial effect can be due to bacteria intracellular porphyrins and the production of cytotoxic reactive oxygen molecules, among other things. Referring to FIG. 41A, the box area 530 highlights the wavelengths of light (405-470 nm) in accordance with aspects of the disclosure. In particular, the wavelengths of light (405-470 nm) show it is possible for antimicrobial effects against orthopaedic relevant bacteria. Further, one of the blue light outputs from the optical fiber at 405 nm (see FIG. 41A, peak of line 532 in oval 534), show that this wavelength can eradicate methicillin-resistant *S. aureus* (MRSA), *S. aureus* and *P. aeruginosa* in a time and dose dependent manner due to the production of cytotoxic reactive oxygen molecules. Further, according to aspects of the disclosure, it is determined that the full spectrum light output during the 400 second implant curing process is capable of bactericidal activity to orthopaedically relevant pathogens.

Figure 42A:
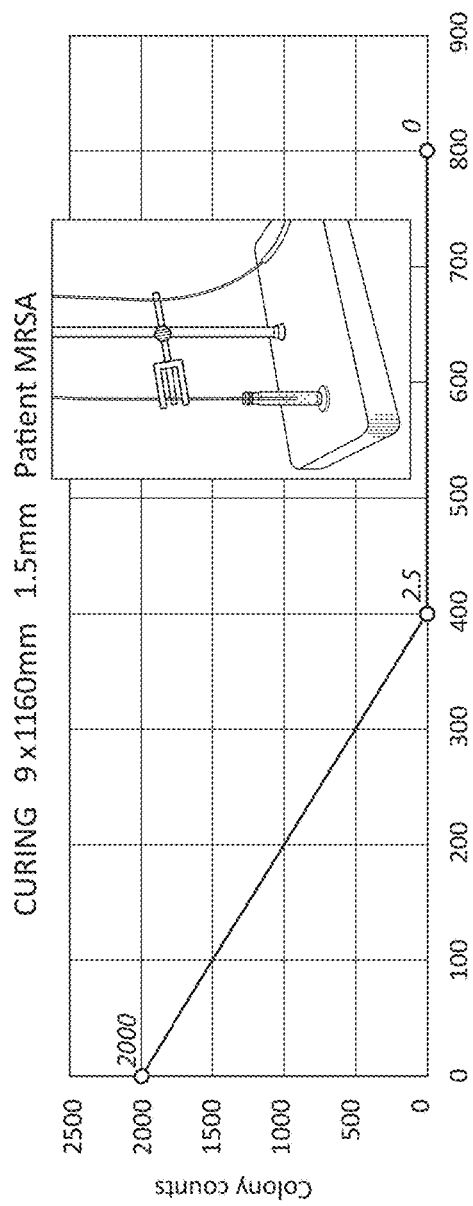
FIG. 42A shows an exemplary graph of the number of the patient isolated MRSA culture counts versus time in seconds curing with the blue light.
Figure 42B:
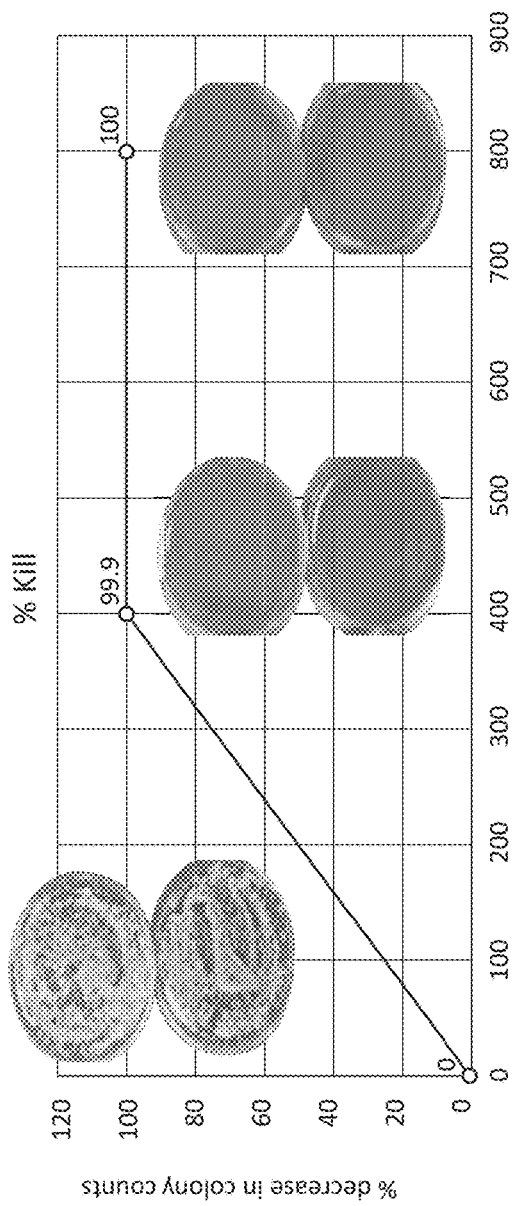
FIG. 42B shows the percent decrease in colony counts versus time in seconds curing with the blue light.

FIG. 42A and FIG. 42B show patient isolated MRSA suspension cultures treated with blue light from an implant 9×160 mm with curing occurring at 400 seconds. FIG. 42A shows a graph of the number of the patient isolated MRSA culture counts versus time in seconds curing with the blue light. FIG. 42B shows the percent decrease in colony counts versus time in seconds curing with the blue light. FIG. 42A and FIG. 42B illustrates that 99.9% of bacteria is killed during the 400 seconds curing of the implant. Wherein the additional time point at 800 seconds shows 100% inactivation of MRSA.

FIG. 42A shows time dependent inactivation of MRSA (samples taken at every 400 seconds) seen after plating 100 ul onto 100 mm blood agar plates and incubating for 24 hrs at 37° C. at 5.5% $CO_2$. FIG. 42B shows 99.9% of bacteria killed during the 400 seconds curing of the implant. An additional time point at 800 seconds is shown with 100% inactivation of MRSA. It is noted that temperature measurements were never above 26.2° C. indicating no bacterial inactivation due to heat.

According to methods of the disclosure, blue light inactivation of bacteria can be dependent on amount or dose of light as described by the equation:

Energy (J/cm2)=Intensity (W/cm2)×time (seconds)

Wherein, it is noted that a dose of 36 J/cm2 is toxic to bacteria but not harmful to mammalian cells. It is possible to use suspension cultures to determine the effect of blue light on bacterial inactivation, wherein this method was used to study the effect of blue light on control bacteria, i.e. MSSA (ATCC 29213) and MRSA (ATCC 43300). Further, according to aspects of the disclosure the bacterial strain was diluted in 0.9% NSS until reaching an optical density of approximately 0.5 McFarland units (1.5×10⁸ CFU/ml). Initial experiments were completed to determine a correct serial dilution in NSS to obtain about 200 colonies per 100 ul inoculum onto 100 mm blood agar plates. After final dilutions to a concentration that is relevant to cause orthopaedic related infections (around 105), 3 ml of bacterial suspension was used for the light dosing experiments. A time-depending bacterial killing was noted in these control experiments (data not shown). These suspension culture experiments were repeated in duplicate for patient isolated MRSA and data shown in FIG. 42A and FIG. 42B. FIG. 42B shows that a 99.9% killing of MRSA was obtained in 400 seconds used for curing at energy levels that are not toxic to mammalian cells.

According to aspects of methods and embodiments of the disclosure, MRSA is 99.9% inactivated during the 400 seconds cure for the disclosed implant. It is noted that the aspects of the disclosure of bactericidal activity associated with an Orthopaedic Implant that is not due to the intrinsic material properties of the implant. According to aspects of the disclosure, it is contemplated that the effectiveness of implant on bacterial pathogens most commonly causing Orthopedically relevant infections can be a way to minimize or manage surgical site infections. It is possible aspects of the disclosure can be used for decontamination of wounds, implants, infected bone and environmental and biologically contaminated surfaces, among other things.

Light fiber matters, such as plastic fiber optics, are incredibly efficient in the transmission of light with minimal light loss. However, the opposite is the case with any form of diffusing/diffusion light fiber. The intensity of the light will decrease over length of the fiber dependent upon the amount of light being diffused (length and or area).

When illuminating a material for an antimicrobial effect, the intensity is affected by distance to the subject (inverse square law) with the power decreasing with distance.

Hence a process of even diffusion of the light in the cladding over the length of the fiber will result in stronger intensity at the initiation end of the fiber and an ever decreasing amount as distance is increased from the initiation source. This reduction in optical power and intensity negates it's use in the curing of photodynamic implants as the intensity at the distal end has weakened significantly (or the increased power to achieve curing at the distal end of the fiber has been increased so significantly that there is an overpowering of the fiber at the proximal end). To correct this, a variable helix of a cut in the cladding, spiraling down the fiber, with the spiral getting tighter and tighter as the light is bleeding out allows for even light dispersion over the length of the fiber.

In some embodiments, the light dispersion system can be in the form of a high efficiency glass coupling system where the light dispersion element is coupled directly to an external mounted LED, laser, or other high power light source. In this case the fiber is directly abutting the light source.

In some embodiments, the power density available to be delivered to a treatment site is such that the light fiber does not require contact with the media it is killing. For example, the power can be sufficient that it has the ability to provide light to the circumferential area of the fiber (speaks to the efficiency of the system) as the inverse square law deals with the intensity of the light as the distance from the fiber increases.

In some embodiments, fibers may be introduced into the anatomy as a stand-alone device (e.g., through an incision), or they may be introduced into the body via a trocar with the fiber contained within. In some embodiments, fibers may be introduced within a needle (cannula) delivered via catheter through normal body orifices, or into the orifice without a catheter (e.g., ear, urinary). In some embodiments, fibers can be delivered via a channel in a scope.

The light fiber can be constructed by either the removal of cladding to achieve the correct light emission program, or using an optically clear and transmissive material that may have a cladding applied to it to achieve the correct emission profile.

Fibers may be small thin (e.g., 0.5 mm, 1.0 mm, 1.5 mm) which are flexible, permitting easy access to small voids, canals, etc., but the fiber may also be larger dependent upon the anatomical location specified. For example, a nasal fiber may be 3 mm, and a fiber for vaginal delivery may be 10 mm.

The light emission fiber may be extruded or cast. In some embodiment, a cast fiber optic may provide the means to achieve an optical taper (e.g., wider at the light entry side), tapered to the effective dimension of the required fiber.

In some embodiments, the transmission of light via fiber needs to closely approximate the size of the LED to the fiber (e.g., a 1 mm LED needs a fiber that closely approximates that dimension), otherwise there are power losses due to the mismatch in size. In some embodiments, a drawn or tapered fiber permits larger LED sources, or multiple LED sources, to be integrated into the fiber.

All patents, patent applications, and published references cited herein are hereby incorporated by reference in their entirety. It will be appreciated that several of the above-disclosed and other features and functions, or alternatives thereof, may be desirably combined into many other different systems or applications.

What is claimed is:

1. A system for providing treatment to tissue, comprising:
a delivery catheter having an elongated shaft and an inner lumen therethrough; and
one or more optical fibers sized to pass through the inner lumen of the delivery catheter and being configured to deliver light energy to provide an antimicrobial effect to the tissue, the one or more optical fibers being configured to disperse the light energy such that intensity of the light energy is distributed evenly over a length of the one or more optical fibers in both longitudinal and circumferential directions;
wherein the one or more optical fibers include a cladding covering an outer surface thereof, and wherein at least a portion of the cladding of the one or more optical fibers is removed from an outer surface of the one or more optical fibers to achieve the even dispersion of the light energy,
wherein the at least a portion of the cladding is removed to form a helical spiral along the length of the one or more optical fibers, wherein the helical spiral becoming increasingly tight as the helical spiral moves from a proximal end of the one or more optical fibers to a distal end of the one or more optical fibers to achieve an even light distribution over the length of the one or more optical fibers,
wherein the antimicrobial effect of the light energy is configured to kill bacteria to treat bone infections.

2. The system of claim 1, wherein the one or more optical fibers include a cladding covering an outer surface thereof, and wherein at least a portion of the cladding of the one or more optical fibers is removed from an outer surface of the one or more optical fibers to achieve the even dispersion of the light energy.

3. The system of claim 2, wherein the at least a portion of the cladding is removed to form a helical spiral along the length of the one or more optical fibers.

4. The system of claim 3, wherein the helical spiral allows for dispersion of light energy around 360 degrees of the one or more optical fibers.

5. The system of claim 1, wherein the one or more optical fibers includes a diffusive membrane disposed on an outer surface thereof, the diffusive membrane configured to be applied to the outer surface of the one or more optical fibers to achieve the even light distribution over the length of the one or more optical fibers.

6. The system of claim 1, wherein the light energy has illumination wavelengths from about 400 nm to about 475 nm.

7. The system of claim 1, wherein the light energy has illumination wavelengths from about 380 nm to about 500 nm.

8. The system of claim 1, wherein the light energy has illumination wavelengths from about 405 nm to about 470 nm.

9. A system for providing treatment to tissue, comprising:
a light source configured to provide light energy at a plurality of frequencies;
a delivery catheter having an elongated shaft and an inner lumen therethrough; and
one or more optical fibers sized to pass through the inner lumen of the delivery catheter and being configured to deliver the light energy from the light source to provide an antimicrobial effect to the tissue, the one or more optical fibers being configured to disperse the light energy such that intensity of the light energy is distributed evenly over a length of the one or more optical fibers in both longitudinal and circumferential directions;
wherein the one or more optical fibers include a cladding covering an outer surface thereof, and wherein at least a portion of the cladding of the one or more optical fibers is removed from an outer surface of the one or more optical fibers to achieve the even dispersion of the light energy,
wherein the at least a portion of the cladding is removed to form a helical spiral along the length of the one or more optical fibers, wherein a depth of the removal of the cladding increases as the helical spiral moves from a proximal end of the one or more optical fibers to a distal end of the one or more optical fibers to achieve an even light distribution over the length of the one or more optical fibers, and
wherein the antimicrobial effect of the light energy is configured to reduce an amount of one or more pathogens in a bone.

10. The system of claim 9, wherein the plurality of frequencies of the light energy are selected based on the antimicrobial effect on specific microbial targets for each of the plurality of frequencies of light energy.

11. The system of claim 10, wherein a subset of the plurality of frequencies of light energy can be used based on the specific microbial targets.

12. The system of claim 9, wherein the light energy has illumination wavelengths from about 400 nm to about 475 nm.

13. The system of claim 9, wherein the light source is in the form of a chain of a plurality of LEDs such that the chain of the plurality of LEDs can produce even light dispersion over a length of the chain.

14. A system for providing treatment to tissue, comprising:
a light source configured to provide light energy having a selected power associated therewith;
a delivery catheter having an elongated shaft and an inner lumen therethrough; and
one or more optical fibers configured to include a cladding covering an outer surface thereof and sized to pass through the inner lumen of the delivery catheter and being configured to deliver the light energy from the light source to provide an antimicrobial effect to the tissue, the one or more optical fibers being configured to disperse the light energy such that intensity of the light energy is distributed evenly over a length of the one or more optical fibers with an even power distribution over the length of the one or more optical fibers based on the selected power,
wherein a portion of the cladding is removed in a helical spiral that is configured to become increasingly tight as the helical spiral moves from a proximal end of the one or more optical fibers to a distal end of the one or more optical fibers to achieve an even light distribution over the length of the one or more optical fibers.

15. The system of claim 14, wherein the light energy is evenly dispersed over the length of the one or more optical fibers in both longitudinal and circumferential directions.

16. The system of claim 14, wherein the light source comprises a plurality of frequencies of the light energy.

17. A system for providing treatment to tissue, comprising:
a delivery catheter having an elongated shaft and an inner lumen therethrough; and
one or more optical fibers sized to pass through the inner lumen of the delivery catheter and being configured to deliver light energy to provide an antimicrobial effect to the tissue, the one or more optical fibers being configured to disperse the light energy such that intensity of the light energy is distributed evenly over a length of the one or more optical fibers in both longitudinal and circumferential directions;
wherein the one or more optical fibers include a cladding covering an outer surface thereof, and wherein at least a portion of the cladding of the one or more optical fibers is removed from an outer surface of the one or more optical fibers to form a helical spiral along the length of the one or more optical fibers, wherein a depth of the removal of the cladding increases as the helical spiral moves from a proximal end of the one or more optical fibers to a distal end of the one or more optical fibers to achieve the even dispersion of the light energy,
wherein the antimicrobial effect of the light energy is configured to kill bacteria to treat bone infections.

* * * * *